US012564568B2

(12) United States Patent
Laperle et al.

(10) Patent No.: US 12,564,568 B2
(45) Date of Patent: Mar. 3, 2026

(54) PKC PATHWAY IN PARKINSON'S DISEASE

(71) Applicant: CEDARS-SINAI MEDICAL CENTER, Los Angeles, CA (US)

(72) Inventors: Alexander Laperle, North Hollywood, CA (US); Samuel Sances, Santa Monica, CA (US); Nur Yucer, Los Angeles, CA (US); Clive N. Svendsen, Pacific Palisades, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 1178 days.

(21) Appl. No.: 17/043,344

(22) PCT Filed: Apr. 5, 2019

(86) PCT No.: PCT/US2019/026193
§ 371 (c)(1),
(2) Date: Sep. 29, 2020

(87) PCT Pub. No.: WO2019/212690
PCT Pub. Date: Nov. 7, 2019

(65) Prior Publication Data
US 2021/0023039 A1    Jan. 28, 2021

Related U.S. Application Data

(60) Provisional application No. 62/816,795, filed on Mar. 11, 2019, provisional application No. 62/755,365, (Continued)

(51) Int. Cl.
*A61K 31/22* (2006.01)
*A61K 35/545* (2015.01)
(Continued)

(52) U.S. Cl.
CPC ............ *A61K 31/22* (2013.01); *A61K 35/545* (2013.01); *A61P 25/16* (2018.01); *C12N 5/0696* (2013.01);
(Continued)

(58) Field of Classification Search
CPC ..... A61K 31/22; A61P 25/16; C07C 2603/86; C07C 69/533; G01N 33/5008; G01N 33/6896
See application file for complete search history.

(56) References Cited

U.S. PATENT DOCUMENTS 6,300,080 B1    10/2001 Brenner et al.
7,989,197 B2    8/2011 Yoo et al.
(Continued)

FOREIGN PATENT DOCUMENTS

AU    2015204375 A1    8/2015
AU    2016341880 A1    5/2018
(Continued)

OTHER PUBLICATIONS

Recchia et al., α-Synuclein and Parkinson's disease, The FASEB Journal, vol. 18, 617-626, Apr. 2004 (Year: 2004).*
(Continued)

*Primary Examiner* — Sarah Pihonak
*Assistant Examiner* — Padmaja S Rao
(74) *Attorney, Agent, or Firm* — NIXON PEABODY LLP

(57) ABSTRACT

Induced Pluripotent Stem Cell (iPSC) technology enables the generation and study of living brain tissue relevant to Parkinson's disease (PD) ex vivo. Utilizing cell lines from PD patients presents a powerful discovery system that links cellular phenotypes observed in vitro with real clinical data. Differentiating patient derived iPSCs towards a dopaminergic (DA) neural fate revealed that these cells exhibit molecular and functional properties of DA neurons in vitro that are
(Continued)

observed to significantly degenerate in the substantia nigra of PD patients. Clinical symptoms that drive the generation of other relevant cell types may also yield novel PD specific phenotypes in vitro that have the potential to lead to new therapeutic avenues for patients with PD. Due to their early onset and nonfamilial origin, differentiated nervous tissue from these patients offer a key opportunity to discover neuron subtype specific pathological mechanisms and importantly interrogate the contribution of their genetic background in susceptibility to PD.

21 Claims, 45 Drawing Sheets

Related U.S. Application Data filed on Nov. 2, 2018, provisional application No. 62/664,942, filed on May 1, 2018, provisional application No. 62/664,827, filed on Apr. 30, 2018, provisional application No. 62/664,888, filed on Apr. 30, 2018.

(51) Int. Cl.

| | |
|---|---|
| *A61P 25/16* | (2006.01) |
| *C12N 5/074* | (2010.01) |
| *C12N 5/10* | (2006.01) |
| *C12N 15/11* | (2006.01) |
| *G01N 33/50* | (2006.01) |
| *G01N 33/68* | (2006.01) |

(52) U.S. Cl.
CPC ............. *C12N 5/10* (2013.01); *C12N 15/111* (2013.01); *G01N 33/5008* (2013.01); *G01N 33/6896* (2013.01); *G01N 2333/4704* (2013.01)

(56) References Cited

U.S. PATENT DOCUMENTS

| | | | |
|---|---|---|---|
| 8,647,861 | B2 | 2/2014 | Ingber et al. |
| 9,790,470 | B2 | 10/2017 | Vallier et al. |
| 10,174,289 | B2 | 1/2019 | Wells et al. |
| 11,326,149 | B2 | 5/2022 | Kerns et al. |
| 2004/0247571 | A1 | 12/2004 | Meijer et al. |
| 2007/0077649 | A1 | 4/2007 | Sammak et al. |
| 2007/0128722 | A1 | 6/2007 | Lin |
| 2007/0281353 | A1 | 12/2007 | Vacanti et al. |
| 2008/0044847 | A1 | 2/2008 | Shusta et al. |
| 2008/0132445 | A1 | 6/2008 | Ormandy et al. |
| 2008/0305086 | A1 | 12/2008 | Poole |
| 2009/0075374 | A1 | 3/2009 | Palecek et al. |
| 2009/0123383 | A1 | 5/2009 | Frangioni |
| 2009/0214649 | A1 | 8/2009 | Gazit et al. |
| 2009/0258337 | A1 | 10/2009 | Yagi |
| 2009/0317852 | A1 | 12/2009 | Parker et al. |
| 2009/0324559 | A1 | 12/2009 | Sakurada et al. |
| 2010/0136690 | A1 | 6/2010 | Sundstorm et al. |
| 2011/0064700 | A1 | 3/2011 | Cardozo et al. |
| 2011/0097796 | A1 | 4/2011 | Loa |
| 2011/0111499 | A1 | 5/2011 | Torihashi |
| 2011/0245307 | A1 | 10/2011 | Alkon |
| 2011/0250585 | A1 | 10/2011 | Ingber et al. |
| 2012/0094381 | A1 | 4/2012 | Chambers et al. |
| 2012/0107934 | A1 | 5/2012 | Poole |
| 2012/0128655 | A1 | 5/2012 | Kim et al. |
| 2012/0171354 | A1 | 7/2012 | O'Neill et al. |
| 2012/0196312 | A1 | 8/2012 | Sato et al. |
| 2012/0211373 | A1 | 8/2012 | El-Sayed et al. |
| 2013/0137130 | A1 | 5/2013 | Wells et al. |
| 2013/0224857 | A1 | 8/2013 | Blak et al. |
| 2013/0280802 | A1 | 10/2013 | Schulz et al. |
| 2013/0288969 | A1 | 10/2013 | Scadden |
| 2014/0038279 | A1 | 2/2014 | Ingber et al. |
| 2014/0065660 | A1 | 3/2014 | Kim et al. |
| 2014/0093905 | A1 | 4/2014 | Ingber et al. |
| 2014/0134732 | A1 | 5/2014 | Ashton |
| 2014/0142370 | A1 | 5/2014 | Wong et al. |
| 2014/0171380 | A1 | 6/2014 | Kim et al. |
| 2014/0199700 | A1 | 7/2014 | Kume et al. |
| 2014/0248621 | A1 | 9/2014 | Collins |
| 2014/0288093 | A1 | 9/2014 | Krainc et al. |
| 2014/0315990 | A1 | 10/2014 | Alkon et al. |
| 2014/0329321 | A1 | 11/2014 | Rajesh et al. |
| 2014/0342445 | A1 | 11/2014 | Ingber et al. |
| 2015/0017674 | A1 | 1/2015 | Christensen et al. |
| 2015/0023928 | A1 | 1/2015 | Hassiotou |
| 2015/0037320 | A1 | 2/2015 | McGrath et al. |
| 2015/0071874 | A1* | 3/2015 | Han .................... A61K 31/23 514/249 |
| 2015/0151011 | A1 | 6/2015 | Jang et al. |
| 2015/0218522 | A1 | 8/2015 | Peterson et al. |
| 2015/0232810 | A1 | 8/2015 | Luo et al. |
| 2015/0252328 | A1 | 9/2015 | Woodruff et al. |
| 2015/0258124 | A1 | 9/2015 | Katajisto et al. |
| 2015/0265652 | A1 | 9/2015 | George et al. |
| 2015/0329828 | A1 | 11/2015 | Rezania |
| 2016/0145642 | A1 | 5/2016 | Cui et al. |
| 2016/0152950 | A1 | 6/2016 | Zhang et al. |
| 2016/0340633 | A1 | 11/2016 | Davis et al. |
| 2017/0107498 | A1 | 4/2017 | Sareen et al. |
| 2017/0226478 | A1 | 8/2017 | Kerns et al. |
| 2017/0240866 | A1 | 8/2017 | Wells et al. |
| 2017/0253856 | A1 | 9/2017 | Douvaras et al. |
| 2017/0283772 | A1 | 10/2017 | Qian et al. |
| 2017/0292116 | A1 | 10/2017 | Erlls et al. |
| 2017/0313976 | A1 | 11/2017 | Kuwahara et al. |
| 2018/0021383 | A1 | 1/2018 | George et al. |
| 2018/0057788 | A1 | 3/2018 | Kerns et al. |
| 2018/0237741 | A1 | 8/2018 | Gazit et al. |
| 2018/0298331 | A1 | 10/2018 | Kerns et al. |
| 2018/0298332 | A1 | 10/2018 | Kerns et al. |
| 2018/0305651 | A1 | 10/2018 | Kerns et al. |
| 2018/0305668 | A1 | 10/2018 | Gazit et al. |
| 2019/0009270 | A1 | 1/2019 | Gazit et al. |
| 2019/0018000 | A1 | 1/2019 | Gazit et al. |
| 2019/0031992 | A1 | 1/2019 | Kerns et al. |
| 2019/0153395 | A1 | 5/2019 | Barrett et al. |
| 2019/0194606 | A1 | 6/2019 | Vatine et al. |
| 2019/0359924 | A1 | 11/2019 | Kerns et al. |
| 2020/0002671 | A1 | 1/2020 | Qu et al. |
| 2020/0032215 | A1 | 1/2020 | Svendsen et al. |
| 2020/0071673 | A1 | 3/2020 | Sareen et al. |
| 2020/0157508 | A1 | 5/2020 | Barrett et al. |
| 2021/0000880 | A1 | 1/2021 | Svendsen et al. |
| 2021/0023039 | A1 | 1/2021 | Laperle et al. |
| 2021/0024886 | A1 | 1/2021 | Laperle et al. |
| 2021/0033628 | A1 | 2/2021 | Laperle et al. |
| 2021/0130774 | A1 | 5/2021 | Sances et al. |
| 2023/0159896 | A1 | 5/2023 | Sharma et al. |
| 2023/0333092 | A1 | 10/2023 | Sances et al. |
| 2024/0067933 | A1 | 2/2024 | Laperle et al. |
| 2024/0076629 | A1 | 3/2024 | Laperle et al. |
| 2025/0057887 | A1 | 2/2025 | Svendsen et al. |

FOREIGN PATENT DOCUMENTS

| | | | |
|---|---|---|---|
| AU | 2017213795 | A1 | 8/2018 |
| AU | 2017214468 | A1 | 9/2018 |
| AU | 2017319168 | A1 | 3/2019 |
| AU | 2017321489 | A1 | 3/2019 |
| AU | 2018235950 | A1 | 10/2019 |
| AU | 2018236273 | A1 | 10/2019 |
| AU | 2018270270 | A1 | 12/2019 |
| AU | 2017319168 | B2 | 4/2021 |
| AU | 2016341880 | B2 | 5/2021 |
| CA | 3002399 | A1 | 4/2017 |
| CA | 3013337 | A1 | 8/2017 |
| CA | 3013357 | A1 | 8/2017 |
| CA | 3034614 | A1 | 3/2018 |
| CA | 3035058 | A1 | 3/2018 |

(56) References Cited

FOREIGN PATENT DOCUMENTS

| CA | 3055992 A1 | 9/2018 |
| CA | 3056089 A1 | 9/2018 |
| CA | 3064086 A1 | 11/2018 |
| CN | 109642212 A | 4/2019 |
| EP | 3008168 A1 | 4/2016 |
| EP | 3031908 A1 | 6/2016 |
| EP | 3365424 A0 | 8/2018 |
| EP | 3411470 A2 | 12/2018 |
| EP | 3411472 A1 | 12/2018 |
| EP | 3503901 A1 | 7/2019 |
| EP | 3504319 A1 | 7/2019 |
| EP | 3625331 A1 | 3/2020 |
| EP | 3768823 | 1/2021 |
| EP | 3775161 | 2/2021 |
| EP | 3787613 | 3/2021 |
| EP | 3787649 A1 | 3/2021 |
| EP | 4217114 A1 | 8/2023 |
| GB | 2561312 A | 10/2018 |
| GB | 2562406 A | 11/2018 |
| GB | 2564582 A | 1/2019 |
| GB | 2568446 A | 5/2019 |
| GB | 2569058 A | 6/2019 |
| GB | 2574988 A | 12/2019 |
| GB | 2575574 A | 1/2020 |
| GB | 2561312 B | 3/2021 |
| GB | 2564582 B | 9/2021 |
| HK | 1260726 B2 | 7/2021 |
| JP | 2003-511346 | 9/2000 |
| JP | 2013-537553 A | 10/2013 |
| JP | 2014-171434 | 9/2014 |
| JP | 2014-171434 A | 9/2014 |
| JP | 2014-528247 A | 10/2014 |
| JP | 2015-504427 A | 2/2015 |
| JP | 2015-504676 A | 2/2015 |
| JP | 2015504676 | 2/2015 |
| JP | 2018533940 A | 11/2018 |
| JP | 2019506861 A | 3/2019 |
| JP | 2021-520784 A | 8/2021 |
| JP | 2021-523700 A | 9/2021 |
| JP | 2021-523888 A | 9/2021 |
| KR | 20180069882 A | 6/2018 |
| SG | 11201803143Y A | 5/2018 |
| SG | 11201901621V A | 3/2019 |
| SG | 11201901628X A | 3/2019 |
| SG | 11201908358P A | 10/2019 |
| SG | 11201908359U A | 10/2019 |
| WO | 2000053218 | 9/2000 |
| WO | 2005021720 A2 | 3/2005 |
| WO | WO 2010009307 A2 | 1/2010 |
| WO | WO 2010/108005 A2 | 9/2010 |
| WO | 2011109440 A1 | 9/2011 |
| WO | 2012/100084 A1 | 7/2012 |
| WO | WO 2012/118799 A2 | 9/2012 |
| WO | 2013/056216 A1 | 4/2013 |
| WO | 2013/071282 A1 | 5/2013 |
| WO | WO 2013/065763 A1 | 5/2013 |
| WO | 2013/086486 A1 | 6/2013 |
| WO | 2013108926 A1 | 7/2013 |
| WO | WO2013106677 A1 | 7/2013 |
| WO | 2013/184193 A1 | 12/2013 |
| WO | WO 2014/172682 A1 | 10/2014 |
| WO | WO 2014/176606 A1 | 10/2014 |
| WO | WO 2014159356 A1 | 10/2014 |
| WO | WO 2015/052143 A1 | 4/2015 |
| WO | WO 2015/057261 A1 | 4/2015 |
| WO | WO 2015/126528 A1 | 8/2015 |
| WO | 2015143342 A1 | 9/2015 |
| WO | WO 2015/138032 A2 | 9/2015 |
| WO | WO 2015/138034 A2 | 9/2015 |
| WO | WO 2015/163823 A1 | 10/2015 |
| WO | WO 2015153451 A1 | 10/2015 |
| WO | WO 2015/181253 A1 | 12/2015 |
| WO | WO 2015/183920 A2 | 12/2015 |
| WO | WO 2015/188131 A1 | 12/2015 |
| WO | 2016063985 A1 | 4/2016 |
| WO | WO 2016061464 A1 | 4/2016 |
| WO | WO 2016/086040 A1 | 6/2016 |
| WO | WO 2016/093222 A | 6/2016 |
| WO | 2016/141137 A1 | 9/2016 |
| WO | 2016162747 A2 | 10/2016 |
| WO | 2016183252 A1 | 11/2016 |
| WO | WO 2017/035119 A1 | 3/2017 |
| WO | 2017070224 A1 | 4/2017 |
| WO | 2017075271 A1 | 5/2017 |
| WO | 2017078807 A1 | 5/2017 |
| WO | 2017/112455 A1 | 6/2017 |
| WO | WO 2017/123806 A1 | 7/2017 |
| WO | WO 2017/136462 A2 | 8/2017 |
| WO | WO 2017/136479 A1 | 8/2017 |
| WO | WO 2017/143049 A1 | 8/2017 |
| WO | WO 2017/200486 A1 | 11/2017 |
| WO | 2017/219000 A1 | 12/2017 |
| WO | 2018/035214 A1 | 2/2018 |
| WO | WO 2018/044885 A1 | 3/2018 |
| WO | WO 2018/044934 A1 | 3/2018 |
| WO | 2018106628 A1 | 6/2018 |
| WO | 2018/140647 A1 | 8/2018 |
| WO | 2018/176001 A1 | 9/2018 |
| WO | 2018175574 A1 | 9/2018 |
| WO | WO 2018/170139 A1 | 9/2018 |
| WO | WO 2018/170180 A1 | 9/2018 |
| WO | WO 2018/213773 A1 | 11/2018 |
| WO | 2019023793 A1 | 2/2019 |
| WO | 2019/122291 A2 | 6/2019 |
| WO | 2019169351 A1 | 9/2019 |
| WO | 2019178164 A1 | 9/2019 |
| WO | 2019178550 A1 | 9/2019 |
| WO | WO 2019/183597 A1 | 9/2019 |
| WO | 2019195798 A1 | 10/2019 |
| WO | 2019195800 A1 | 10/2019 |
| WO | 2019212690 A1 | 11/2019 |
| WO | 2019212691 A1 | 11/2019 |
| WO | 2021/081229 A1 | 4/2021 |
| WO | 2021/081237 A1 | 4/2021 |
| WO | 2021222724 A1 | 11/2021 |
| WO | 2022066723 A1 | 3/2022 |

OTHER PUBLICATIONS

Yuan et al., Overexpression of α-Synuclein Down-Regulates BDNF Expression, Cell and Molecular Neurobiology, vol. 30, 939-946, 2010 (Year: 2010).*

International Search Report and Written Opinion of PCT Application No. PCT/US2017/013250, Dated Mar. 31, 2017, 12 Pages.

International Search Report and Written Opinion of PCT Application No. PCT/US2016/057724, Dated Jan. 9, 2017, 17 Pages.

International Search Report and Written Opinion of PCT/US2017/016098, Dated Jun. 22, 2017, 14 Pages.

International Search Report and Written Opinion of PCT/US2017/016079, Dated Jul. 25, 2017, 26 Pages.

International Search Report and Written Opinion of PCT/US2017/049193, Dated Nov. 6, 2017, 9 Pages.

International Search Report and Written Opinion of PCT/US2017/049115, Dated Nov. 28, 2017, 11 Pages.

International Search Report and Written Opinion of PCT/US2018/022511, Dated Jul. 26, 2018, 11 Pages.

International Search Report and Written Opinion of PCT/US2018/033498, Dated Aug. 9, 2018, 9 Pages.

International Search Report and Written Opinion for PCT/US2018/022455 dated Aug. 23, 2018, 13 pages.

International Preliminary Report on Patentability for PCT/US2016/057724 dated Apr. 24, 2018, 15 pages.

International Preliminary Report on Patentability for PCT/US2017/013250 dated Jul. 17, 2018, 7 pages.

International Preliminary Report on Patentability for PCT/US2017/016098 dated Aug. 7, 2018, 10 pages.

International Preliminary Report on Patentability for PCT/US2017/016079 dated Aug. 7, 2018, 21 pages.

International Preliminary Report on Patentability for PCT/US2018/022511, dated Sep. 17, 2019, 8 pages.

(56)  References Cited

OTHER PUBLICATIONS

International Preliminary Report on Patentability for PCT/US2018/022455 dated Aug. 23, 2018, 9 pages.
International Preliminary Report on Patentability for PCT/US2018/033498 dated Nov. 19, 2019, 8 pages.
International Preliminary Report on Patentability for PCT/US2017/049193 dated Mar. 5, 2019, 8 pages.
International Preliminary Report on Patentability for PCT/US2017/049115 dated Mar. 5, 2019, 8 pages.
International Search Report and Written Opinion of PCT/US2019/023749, Dated Jun. 25, 2019, 12 Pages.
AU 2016341880 Examination Report dated Jan. 15, 2020, 5 pages.
AU 2017214468 Examination Report dated Dec. 10, 2019, 5 pages.
CA 3034614 Examination Report dated Jul. 5, 2019, 5 pages.
EP 16858141.1 Extended Search Report dated Mar. 15, 2019, 10 pages.
EP 17748100.9 European Partial Supplementary Search Report dated Sep. 18, 2019, 15 pages.
EP 17748100.9 European Extended Search Report dated Dec. 20, 2019, 12 pages.
EP 17748084.5 European Extended Search Report dated Sep. 10, 2019.
EP 17847396.3 European Extended Search Report dated, Jan. 28, 2020, 11 pages.
EP17847365.8 European Extended Search Report dated Jan. 21, 2020, 11 pages.
GB1811716.8 Examination Report dated Feb. 12, 2020, 6 pages.
GB 1903007.1 Search Report dated Apr. 1, 2019, 8 pages.
SG 11201803143Y Search Report dated Jul. 15, 2019, 3 pages.
Action Potential, Wikipedia, pp. 1-29 Downloaded on Apr. 28, 2019, https://en.wikipedia.org/wiki/Action_potential.
Adriani et al., Modeling the Blood-Brain Barrier in a 3D Triple Co-Culture Microfluidic System, 37th Annual International Conference of the IEEE Engineering in Medicine and Biology Society, IEEE, pp. 338-341.
Armstrong et al., Human Induced Pluripotent Stem Cell Lines Show Stress Defense Mechanisms and Mitochondrial Regulation Similar to Those of Human Embryonic Stem Cells, 2010, Stem Cells, vol. 28(4), pp. 661-673.
Barrett et al., Reliable Generation of Induced Pluripotent Stem Cells from Human Pymphoblastoid Cell Lines, 2014, Stem Cells Translational Medicine, vol. 3, pp. 1429-1434.
Ben-Zvi et al., Modeling Human Nutrition Using Human Embryonic Stem Cells, Cell, 2015, vol. 161(1), pp. 12-17.
Bhatia et al., Microfluidic Organs-on-Chips, Nature Biotechnology, 2014, vol. 32(8), pp. 760-772.
Booth, Ross Hunter, A Microfluidic in Vitro Model of the Blood-Brain Barrier, Dissertation, 2014, pp. 1-177.
Boyer et al., More than a Bystander: The Contributions of Intrinsic Skeletal Muscle Defects in Motor Neuron Diseases, 2013, Frontiers in Physiology, vol. 4, Article 356, pp. 1-12.
Brown et al., Recreating Blood-Brain Barrier Physiology and Structure on Chip: A Novel Neurovascular Microfluidic Bioreactor, 2015, Biomicrofluidics, vol. 9(5).
Cashman et al., Induced Pluripotent Stem Cells and Motor Neuron Disease: Toward an Era of Individualized Medicine, J. Neurosci, 2013, vol. 33, pp. 8587-8589.
Chal et al., Differentiation of Pluripotent Stem Cells to Muscle Fiber to Model Duchenne Muscular Dystrophy, 2015, Nature Biotechnology, vol. 33(9), pp. 962-969.
Chen et al., Surface Marker Epithelial Cell Adhesion Molecule and E-Cadherin Facilitate the Identification and Selection of Induced Pluripotent Stem Cells, 2011, Stem Cell Rev., vol. 7(3), pp. 722-735.
Date et al., Mini-Gut Organoids: Reconstruction of the Stem Cell Niche, Annu. Rev. Cell Dev. Biol., 2015, vol. 31, pp. 269-289.
Dhumpa et al., Temporal Gradients in Microfluidic Systems to Probe Cellular Dynamics: A Review, Anal. Chim. Acta, 2012, vol. 743, pp. 9-18.

Dimos et al., Induced Pluripotent Stem Cells Generated from Patients with ALS can be Differentiated into Motor Nuerons, Science, 2008, vol. 321, pp. 1218-1221.
Douville et al., Fabrication of Two-Layered Channel System with Embedded Electrodes to Measure Resistance Across Epithelial and Endothelial Barriers, 2010, Analytical Chemistry, vol. 82(6), pp. 2505-2511.
Ebert et al., EZ Spheres: A Stable and Expandable Culture System for the Generation of Pre-rosette Multipotent Stem Cells from Human ESCs and iPSCs., 2013, Stem Cell Research, vol. 10(3), pp. 417-427.
Esch et al., Organs-on-Chips at the Frontiers of Drig Discovery, Nature Reviews, 2015, vol. 14(4), pp. 248-269.
Evans et al., The Development of a Method for the Preparation of Rat Intestinal Epithelial Cell Primary Cultures, 1992, Journal of Cell Science, vol. 101, pp. 219-231.
Gao et al., Regulation of Cell Migration and Osteogenic Differentiation in Mesenchymal Stem Cells under Extremely Low Fluidic Shear Stress, Biomicrofluidics, 2014, vol. 8(5), Article No. 052008.
Gel, Wikipedia, pp. 1-29 Downloaded on Sep. 14, 2018, https://en.wikipedia.org/wiki/Gel.
Gracz et al., CD24 and CD44 Mark Human Intestinal Epithelial Cell Populations with Characteristics of Active and Facultative Stem Cells, 2013, Stem Cells, vol. 31(9), pp. 2024-2030.
Gross et al., Applications of Microfluidics for Neuronal Studies, 2007, Journal of the Neurological Sciences, vol. 252, pp. 135-143.
Hu et al. Neural differentiation of human induced pluripotent stem cells follows developmental principles but with variable potency, PNAS, 2010, vol. 107(9), pp. 4335-4340.
Hu et al., Derivation, Expansion and Motor Neuron Differentiation of Human-Induced Pluripotent Stem Cells with Non-Integrating Episomal Vectors and a Defined Xenogeneic-Free Culture System, Mol Neurobiol, 2016, vol. 53, pp. 1589-1600.
Hughes et al., Matrigel: A Complex Protein Mixture Required for Optimal Growth of Cell Culture, 2010, Proteomics, vol. 10, pp. 1886-1890.
Huh et al., From 3D Cell Culture to Organs-on-Chips, Trends in Cell Biology, 2011, vol. 21(2), pp. 745-754.
Huh et al., Microfabrication of Human Organs-on-Chips, Nature Protocols, 2013, vol. 8(11), pp. 2135-2157.
Hynds et al., Concise Review: The Relevance of Human Stem Cell-Derived Organoid Models for Epithelial Transitional Medicine, Stem Cells, 2013, vol. 1 31, pp. 417-422.
Jang et al., JAK-STAT Pathway and Myogenic Differentiation, JAKSTAT, 2013, vol. 2(2), pp. e23282-1 to e-23282-6.
Joo-Eun, L., Patient-Specific Induced Pluripotent Stem Cell Models of Variant Angina Derived from Peripheral Blood, The Department of Biomedical Sciences Seoul National University College of Medicine, Jul. 2017, pp. 1-75.
Kilic et al., Brain-on-a-Chip Model Enables Analysis of Human Neuronal Differentiation and Chemotaxis, 2016, Lab on a Chip, vol. 16(21), pp. 4152-4162.
Kim et al., Human Gut-on-a-Chip Inhabited by a Microbial Flora that Experiences Intestinal Peristalsis-Like Motions and Flow, Lab on a Chip, 2012, vol. 12(12). pp. 2165.
Kim et al., Gut-on-a-Chip Microenvironmental Induces Human Intestinal Cells to Undergo Villus Differentiation, Integrative Biology, 2013, vol. 5(9), p. 1130-1140.
Kim et al., Contributions of Microbiome and Mechanical Deformation to Intestinal Bacterial Overgrowth and Inflammation in a Human Gut-on-a-Chip, PNAS, 2015, vol. 113(1), pp. E7-E15.
Kirkby et al., A Role for Correlated Spontaneous Activity in the Assembly of Neural Circuits, 2013, Neuron, vol. 80(5), 27 Pages.
Lenner, J., Fat Cells More Easily Programmed into iPS Cells, 2009, pp. 1-2.
Lin et al., Neural Stem Cell Differentiation in a Cell-Collagen-Bioreactor Culture System, 2004, Developmental Brain Research, vol. 153, pp. 163-173.
Lippmann, et al., Human Blood-Brain Barrier Endothelial Cells Derived from Pluripotent Stem Cells, 2012, Nature Biotechnology, vol. 30(8), pp. 783-791.

(56) References Cited

OTHER PUBLICATIONS

Lippmann et al., A Retinoic Acid-Enhanced, Multicellular Human Blood-Brain Barrier Model Derived from Stem Cell Sources, Scientific Reports, vol. 4(1), 2014, pp. 1-10.

Lippmann et al., Chemically Defined Differentiation of Human Pluripotent Stem Cells to Hindbrain and Spinal Cord Neural Stem Cells with Defined Regional Identifies, 2015, Protocol Exchange.

Martin et al., Laparoscopic Colorectal Resection in the Obese Patient, 2011, Clinics in Colon and Rectal Surgery, vol. 24(4), pp. 263-273.

Massumi et al., Efficient Programming of Human Eye Conjunctiva-Derived Induced Pluripotent Stem (ECiPS) Cells into Definitive Endoderm-Like Cells, Experimental Cell Research, 2014, vol. 322, pp. 51-61.

Medical Dictionary—Myotube, Downloaded on Jul. 8, 2018, https://medical-dictionary.thefreedictionary.com/myotube, p. 1.

Murphy et al., Scaffolds for 3D in vitro Culture of Neural Lineage Cells, Acta Biomaterialia, 2017, vol. 54, pp. 1-20.

Nicoleau et al., Embryonic Stem Cells Neural Differentiation Qualifies the Role of Wnt/[beta]-Catenin Signals in Human Telecephalic Specification and Regionalization: Human ESC Telencephalic Differentiation, Stem Cells, 2013, vol. 31(9), pp. 1763-1774.

Niego et al., Improved Method for the Preparation of a Human Cell-based, Contact Model of the Blood-Brain Barrier, 2013, J. Vis. Exp., vol. 81(e50934), pp. 1-9.

Nostro et al., Efficient Generation of NKX6-1+ Pancreatic Progenitors from Multiple Human Pluripotent Stem Cell Lines, Stem Cell Reports, 2015 4(4), pp. 591-604.

Ochetta et al., High-Throughput Microfluidic Platform for 3D Cultures of Mesenchymal Stem Cells, Towards Engineering Developmental Processes, Scientific Reports, 2015, vol. 5, Article No. 10288, pp. 1-12.

Okita et al., A More Efficient Method to Generate Integration-Free Human iPS Cells, 2011, Nature Methods, vol. 8(5), pp. 409-412.

Ong et al., A Gel-Free 3D Microfluidic Cell Culture System, Biomaterials, 2008, vol. 29, pp. 3237-3244.

Park et al., Chip-Based Comparison of the Osteogenesis of Human Bone Marrow and Adipose Tissue-Derived Mesenchymal Stem Cells under Mechanical Stimulation, PLOS One, 2012, vol. 7(9), pp. 1-12.

Polini et al., Organs-on-a-Chip: A New Tool for Drug Discovery, Expert Opinion on Drug Discovery, 2014, vol. 9(4), pp. 335-352.

Prabhakarpandian et al., SyM-BBB: A Microfluidic Blood Brain Barrier Model, Lab on a Chip, 2013, vol. 13(6), p. 1093.

Qian et al., A Simple and Efficient System for Regulating Gene Expression in Human Pluripotent Stem Cells and Derivatives, Stem Cells, 2014, vol. 32(5), pp. 1230-1238.

Rajesh et al., Human Lymphoblastoid B-Cell Lines Reprogrammed to EBV-FREE Induced Pluripotent Stem Cells, 2011, Blood, vol. 118(7), pp. 1797-1800.

Rhee et al., Patterned Cell Culture Inside Microfluidic Devices, Lab Chip, 2005, vol. 5(1), pp. 102-107.

Roberts et al., Expression of the Thyroid Hormone Transports Monocarboxylate Transporter-8 (SLC16A2) and Organic Ion Transporter-14 (SLCO1C1) at the Blood-Brain Barrier, Endocrinol, 2008, vol. 149(12), pp. 6251-6261.

Rosenberg et al., Calcium Signaling in Neuronal Development, 2011, Cold Spring Harb Perspect Biol., vol. 3(a004259), 13 Pages.

Sareen et al., Human Neural Progenitor Cells Generated from Induced Pluripotent Stem Cells can Survive, Migrate, and Integrate in the Rodent Spinal Cord, Journal of Comparative Neurology, 2014, vol. 522(12), pp. 2707-2728.

Sareen et al., Targeting RNA foci in iPSC-Derived Motor Neurons from ALS Patients with C90RF72 Repeat Expansion, 2013, Science Translational Medicine, vol. 5(208), 208ra149, 26 Pages.

Shimojo et al., Rapid, Efficient and Simple Motor Neuron Differentiation from Human Pluripotent Stem Cells, Molecular Brain, 2015, vol. 8(1), pp. 1-15.

Shimuzu et al., Microfluidic Devices for Construction of Contractile Skeletal Muscle Microtissues, J. Biosci. Bioeng., 2015, vol. 119, pp. 212-216.

Soria-Valles et al., NF-kB Activation Impairs Somatic Cell Reprogramming in Ageing, 2015, Nat. Cell Biol., vol. 17(8), pp. 1004-1013.

Stepniewski et al., Induced Pluripotent Stem Cells as a Model for Diabetes Investigation, Scientific Reports, 2015, 5:8597, 14 pages.

Telias et al., Electrical Maturation of Neurons Derived from Human Embryonic Stem Cells, F1000 Research, 2014, vol. 3(196), p. 1-12.

Tenstad et al., Extensive Adipogenic and Osteogenic Differentiation of Patterned Human Mesenchymal Stem Cells in a Microfluidic Device, Lab on a Chip, 2010, vol. 10(11), pp. 1401-1409.

Uzel et al., New Microfluidic Chip Replicates Muscle-Nerve Connection, 2016, Science Daily, pp. 1-4.

Vatine et al., Human iPSC-Derived Blood-Brain Barrier Chips Enable Disease Modeling and Personalized Medicine Applications, Cell Stem Cell, 2019, vol. 24(6), pp. 995-1005.

Vatine et al., Human iPSC-Derived Blood-Brain Barrier Chips Enable Disease Modeling and Personalized Medicine Applications, Cell Stem Cell, 2019, vol. 24, Supplemental Figures, p. 1-10.

Wang et al., Androgen Receptor-Mediated Apoptosis in Bovine Testicular Induced Pluripotent Stem Cells in Response to Phthalate Esters, 2013, Cell Death Dis., vol. 4(e907), pp. 1-11.

Wang et al., Modeling the Mitochondrial Cardiomyopathy of Barth Syndrome with Induced Pluripotent Stem Cell and Heart-on-Chip Technologies, Nature Medicine, 2014, vol. 20(6), pp. 616-623.

Watson et al., Modelling the Endothelial Blood-CNS Barriers: A Method for the Production of Robust in Vitro Models of the Rat Blood-Brain Barrier and Blood-Spinal Cord Barrier, 2013, BMC Neuroscience, vol. 14(59), pp. 1-21.

Wehkamp et al., Reduced Panetll Cell [alpha]-Defensins in Ileal Crohn's Disease, PNAS, 2005, vol. 102, pp. 18129-18134.

Workman et al., Enhanced Utilization of Induced Pluripotent Stem Cell-Derived Human Intestinal Organoids Using Microengineered Chips, CMGH Cellular and Molecular Gastroenterology and Hepatology, 2018, vol. 5(4), pp. 669-677.

Yamamoto et al., Fluid Shear Stress Induces Differentiation of Flk-1-positive Embryonic Stem Cells into Vascular Endothelial Cells in vitro., 2004, Am. J. Physiol. Heart Circ. Physiol., vol. 288, pp. 1915-1924.

Zilio et al., Universal Hydrophilic Coating of Thermoplastic Polymers Currently Used in Microfluidics, 2014, Biomed. Microdevices, vol. 16(1), pp. 107-114.

Fridley et al., Hydrodynamic modulation of pluripotent stem cells, Stem cell research & therapy, 2012, vol. 45.

Zhang et al., Patient-specific 3D microfluidic tissue model for multiple myeloma, Tissue Engineering Part C: Methods, 2014, pp. 663-670.

Jenke et al., DNA Methylation Analysis in the Intestinal Epithelium—Effect of Cell Separation on Gene Expression an Methylation Profile, PLOS One, 2013, vol. 8(2), pp. 1-8.

Brittan et al., The gastrointestial stem cell, Cell Prolif., 2004, vol. 37, pp. 35-53.

Yamamoto et al., The Stabilization Effect of Mesenchymal Stem Cells on the Formation of Microvascular Networks in a Microfluidic Device, Journal of Biomechanical Science and Engineering, 2013, vol. 8(2).

Danmark et al., Development of a novel microfluidic device for long-term in situ monitoring of live cells in 3-dimensional matrices, Biomed Microdevices, 2012, pp. 885-893.

Yu et al., A Microfluidic-Based Multi-Shear Device for Investigating the Effects of Low Fluid-Induced Stresses on Osteoblasts, PLOS One, 2014, vol. 9(2), pp. 1-7.

GB 1903007.1 Search Report dated Jun. 24, 2020, 3 pages.

Extended European Search Report for EP 18802136.4 dated Jan. 22, 2021, 12 pages.

Kuratnik et al., Intestinal organoids at tissue surrogates for toxicological and pharmacological studies, biochemical Pharmacology, Apr. 25, 2013, vol. 85:12, pp. 1721-1726.

Workman et al., Intestine-Chip: A new model to understand the role of the Intestinal Epithelium inIBD by combining Microengineering

(56)         References Cited

OTHER PUBLICATIONS

Technology and IPSC-Derived human intestinal organoids, Gastroenterology, Apr. 1, 2017, vol. 152:5, Abstract only.

Jha et al., Motor Neuron differentiation from Pluripotent Stem Cells and Other Intermediate Proliferative Precursors that can be Discriminated by Lineage Specific Reports, Stem Cell Rev Rep, Aug. 2014, 11:194-204.

Lee et al. Microfluidic 3D bone tissue model for high-throughput evaluation of would healing and infection-preventing biomaterials, Biomaterials 33.4 2012 999-1006.

Amoroso M. W. et al., Accelerated High-Yield Generation of Limb-Innervating Motor Neurons from Human Stem Cells. J Neurosci, Jan. 9, 2013, vol. 33, No. 2, pp. 574-586 pp. 575 and 578, Fig. 1 and 2.

Faravelli I. et al., Motor neuron derivation from human embryonic and induced pluripotent stem cells: Experimental approaches and clinical perspectives. Stem Cell Res Ther, Jul. 14, 2014, vol. 5, No. 4, pp. 87.

Written Opinion 11201901628X dated Mar. 10, 2021, 9 pages.

International Search Report and Written Opinion of PCT/US2019/26178, Dated Jun. 11, 2019, 14 Pages.

Notice of Reasons for Rejection for JP 2018-540028 dated Mar. 1, 2021.

EP 19782199.4 Partial Supplementary Search Report dated Nov. 30, 2021, 15 pages.

EP 19796470.3 European Extended Search Report dated Dec. 10, 2021, 11 pages.

Burkhardt et al., A Cellular Model for Sporadic ALS using Patient-Derived Induced Pluripotent Stem Cells, Molecular and Cellular Neuroscience, 2013, vol. 56, pp. 355-364.

Kitamura et al., Possible Involvement of Both Mitochondria and Endoplasmic Reticulum-Dependent Caspase Pathways in Retenone-Induced Apoptosis in Human Neuroblastoma SH-SY5Y Cells, Neuroscience Letters, 2002, vol. 2002, pp. 25-28.

Lenzi et al., Differentiation of Control and ALS Mutant Human iPSCs into Functional Skeletal Muscle Cells, A Tool for the Study of Neuromuscolar Diseases, Stem Cell Research, 2016, vol. 17, pp. 140-147.

Tian et al., Salvianolic Acid B, An Antioxidant from Saliva Miltiorrhiza, prevents 6-hydroxydopamine Induced Apoptosis In SH-SY5Y Cells, The International Science Journal of Biochemistry & Cell Biology, 2008, vol. 40, pp. 409-422.

Wu et al., Nuclear Accumulation of Histone Deacetylase 4 (HDAC4) Exerts Neurotoxicity in Models of Parkinson's Disease, Moi Neurobiol, 2017, vol. 54, pp. 6970-6983.

International Search Report and Written Opinion for PCT/US2018/015318 May 2, 2018, 16 pages.

International Search Report and Written Opinion for PCT/US2018/024198 dated Aug. 13, 2018, 15 pages.

International Search Report and Written Opinion for PCT/US2020/056896 dated Oct. 22, 2020, 11 pages.

International Search Report and Written Opinion for PCT/US2020/056906 dated Mar. 16, 2021, 13 pages.

International Preliminary Report on Patentability for PCT/US2018/015318 dated Jul. 30, 2019, 12 pages.

International Preliminary Report on Patentability for PCT/US2018/024198 dated Feb. 25, 2020, 12 pages.

EP 19782199.4 Extended European Search Report dated Mar. 3, 2022, 12 pages.

EP 19796911.6 Extended Search Report dated Apr. 29, 2022, 15 pages.

Akhtar et al., Inducible Expression of GDNF in Transplanted iPSC-Derived Nueral Progenitor Cells, Stem Cell Reports, 2018, vol. 10, pp. 1696-1704.

Araoka, et al., Efficient and rapid induction of human iPSCs/ESCs into nephrogenic intermediate mesoderm using small molecule-based differentiation methods, PLoS One, 2014, 9(1), 14 pages.

Badger et al., Parkinson's disease in a dish – Using stem cells as a molecular tool. Neuropharmacology, 2014, vol. 76, pp. 88-96.

Bai et al., BMP-2, VEGF and bFGF Synergistically Promote the Osteogenic Differentiation of Rat Bone Marrow-Derived Mesenchymal Stem Cells, Biotechnol Lett, 2013, vol. 35, pp. 301-308.

Bar-Am et al., Regulation of protein kinase C by the anti-Parkinson drug, MAO-B inhibitor, rasagiline and its derivatives, in vivo, Journal of Neurochemistry, 2004, vol. 89, No. 5, pp. 1119-1125.

Bohrnsen et al. Supportive angiogenic and osteogenic differentiation of mesenchymal stromal cells and endothelial cells in monolayer and co-cultures. International Journal of Oral Science (2016) 8, 223-230 (Year: 2016).

Chen, et al., Chemically defined conditions for human iPSC derivation and culture, 2011, Nat. Methods, 8(5), 8 pages.

Cooper et al., Differentiation of human ES and Parkinson's disease iPS cells into ventral midbrain dopaminergic neurons requires a high activity form of SHH, FGF8a and specific regionalization by retinoic acid, Molecular and Cellular Neurosciences, 2010, vol. 45, No. 3, pp. 258-266.

Farrelly et al., Extracellular matrix regulates apoptosis in mammary epithelium through a control on insulin signaling, The Journal of Cell Biology, 1999, 144(6):1337-1347.

Gurusamy et al., Hepatocyte Growth Factor-Like Protein is a Positive Regulator of Early Mammary Gland Ductal Morphogenesis, Mechanisms of Development, 2014, vol. 133, pp. 11-22.

Hiens et al., BMP4 and PTHrP interact to stimulate ductal outgrowth during embryonic mammary development and to inhibit hair follicle induction, Development, 2017, 134:1221-1230.

Ichida et al., Probing disorders of the nervous system using reprogramming approaches, The EMBO Journal / European Molecular Biology Organization, 2015, vol. 34, No. 11, pp. 1456-1477.

Kessler et al., The Notch and Wnt pathways Regulate Stemness and Differentiation in Human Fallopian Tube Organoids, Nature Communications, 2015, vol. 6, p. 8989.

Kim et al. A practical guide to microfluidic perfusion culture of adherent mammalian cells. Lab Chip, 2007, 7, 681-694 (Year: 2007).

Kim et al. Shear Stress Induced by an Interstitial Level of Slow Flow Increases the Osteogenic Differentiation of Mesenchymal Stem Cells through TAZ Activation. PLoS ONE 9(3): e92427. p. 1-9 (Year: 2014).

Kreke et al. Effect of Intermittent Shear Stress on Mechanotransductive Signaling and Osteoblastic Differentiation of Bone Marrow Stromal Cells. Tissue Engineering: Part A vol. 14, No. 4, 2008. p. 529-537 (Year: 2008).

Levanon, et al., Primary ex vivo cultures of human fallopian tube epithelium as a model for serous ovarian carcinogenesis, Oncogene, 2010, 29(8):1103-1113.

Maegawa et al. Enhancement of osteoblastic differentiation of mesenchymal stromal cells cultured by selective combination of bone morphogenetic protein-2 (BMP-2) and fibroblast growth factor-2 (FGF-2). J Tissue Eng Regen Med 2007; 1: 306-313 (Year: 2007) Abstract Only.

Nishimura et al. Effect of osteogenic differentiation medium on proliferation and differentiation of human mesenchymal stem cells in threedimensional culture with radial flow bioreactor. Regenerative Therapy 2 (2015) 24-31 (Year: 2015).

O'Neill et al., Genetic disorders coupled to ROS deficiency, Redox Biology, 6: 135-156. (Year: 2015).

Qu et al., Differentiation of human induced pluripotent stem cells to mammary-like organoids, Stem Cell Reports, 2017, 8(2):205-215.

Rey, et al., Chapter 7, Sexual Differentiation, 2016 [online]. [Retrieved on Sep. 19, 2019]. Retrieved from the Internet <URL:https://www.endotext.org/wp-content/uploads/pdfs/sexual-differentiation.pdf>, 89 pages.

Ryan et al., Isogenic Human iPSC Parkinson's Model Shows Nitrosative Stress-Induced Dysfunction in MEF2-PGCI [alpha] Trans, Cell, Elsevier, 2013, vol. 155, No. 6, pp. 1351-1364.

Sanchez-Danes et al., Disease-specific phenotypes in dopamine neurons from human iPS-based models of genetic and sporadic Parkinson's disease, EMBO Molecular Medicine, 2015, vol. 4, No. 5, pp. 380-395.

Simeone et al., The Otx Family, Pattern Formation and Development Mechanisms, 2002, vol. 12, pp. 409-415.

(56)            References Cited

OTHER PUBLICATIONS

Sun et al., Role of Bone Morphogenetic Protein-2 in Osteogenic Differentiation of MesenChymal Stem Cells, Molecular Medicine Reports, 2015, vol. 12, pp. 4230-4237.

Vogel et al., Co-culture of human induced pluripotent stem cells 9iPSCs) with human fallopian tube epithelium (FTE) induces Pax8 and CK7 expression: Initial steps in modeling fallopian tube epithelium to study serous carcinogenesis; Gynecologic Oncology, 2015 137(1):206.

Zhang et al., Regulation and Patterning of Cell Differentiation and Pluripotency, Thesis, Columbia University, pp. 1-177, 2011.

Zhang et al., FGF Ligands of the Postnatal Mammary Stroma Regulate Distinct Aspects of Epithelial Morphogenesis, Stem Cells and Regeneration, 2014, vol. 141, pp. 3352-3362.

Zhou et al., Rapid and efficient generation of transgene-free iPSC from a small vol. of cryopreserved blood, Stem Cell Reviews and Reports 11: 652-665. (Year: 2015).

Arendt et al., Form and Function: how Estrogen and Progesterone Regulate the Mammary Epithelial Hierarchy, J. Mammary Gland Biol Neoplasia, 2015, 20:9-25.

Qiao et al., AP2y regulates neural and epiderman development downstream of the BMP pathway at early stages of ectodermal patterning, Cell Research, 2012, 22:1546-1561.

Lin et al., Embryoid body formation from human pluripotent stem cells in chemically defined E8 media, StemBook, ed, Jun. 1, 2014.

JP Reasons for Rejection-2020-560893 dated Feb. 6, 2023, 9 pages.

Matsumoto et al., Functional neurons generated from T Cell-derived induced pluripotent stem cells for neurological disease modeling, 2016, 6:422-435.

Moors et al., Therapeutic potential of autophagy-enhancing agents in Parkinson's disease, Molecular Neurodegeneration, 2017, 12:11, p. 1-18.

Okita et al., An efficient nonviral method to generate integration-free human-induced pluripotent stem cells from cord blood and peripheral blood cells, Stem Cells 2013, 31:458-466.

Kondo et al., iPSC-Based compound screening and in vitro trials identify a synergistic anti-amyloid B combination for Alzheimer's Disease, Cell Reports 2017, 21:2304-2312.

Hojo et al., Development of high-throughput screening system for osteogenic drugs using a cell-based sensor, Biochemical and Biophysical Research Communiatins 376(2):375-379, 2008.

Hayes et al., Strategies to generate induced pluripotentstem cells, Methods in Molecular Biology 1029: 77-92. doi: 10.1007/978-1-62703-478-4_6 (Year: 2013).

Shafa et al., Human-Induced Pluripotent Stem Cells Manufactured Using a Current Good Manufacturing Practice-Compliant Process Differentiate Into Clinically Relevant Cells From Three Germ Layers, Frontiers in Medicine 5: 69. doi: 10.3389/fmed.

Ionescu et al., Compartmental microfluidic system for studying muscle-neuron communication and neuromuscular junction maintenance, 2016 European Journal of Cell Biology, 95:69-88.

DMEM F-12 Formulation, pp. 1-5, 2022.

Mehta et al., The actions of retinoids on cellular growth correlate with their actions on gap junctional communication, JCB 108, 1053-1065, 1989.

Essential 8 medium C037161 Essential8System Brochure (thermofisher.com), downloaded on Aug. 24, 22, pp. 1-2.

ISR and WO for PCT/US2021/030128 mailed Aug. 25, 2021, 10 pages.

Kim, et al. [3-Cell regeneration through the transdifferentiation of pancreatic cells: Pancreatic progenitor cells in the pancreas, Journal of Diabetes Investigation 7(3): 286-296. doi: 10.1111/jdi .12475. (Year: 2016).

Clayton, et al., Generating induced pluripotent stem cell derived endothelial cells and induced endothelial cells for cardiovascular disease modelling and therapeutic angiogenesis, International Journal of Cardiology 197: 116-122. doi: 10.1016/ j.ijcard.2015.06.038. (Year: 2015).

EP 19771249.0 Partial Supplemental European Search Report dated Nov. 8, 2011, 15 pages.

EP 18802136.4 Examination Report dated Oct. 14, 2021, 8 pages.

Abbott et al., Structure and function of the blood-brain barrier, Neurobiology of Desease, 2010 27:13-25.

Abbott et al., Structure and function of the blood-brain barrier, Pharm Tox BBB: Feb. 1-3, 2010, Conf. Abstract.

Demers et al., Development-on-Chip: in vitro Neutral Tube Patterning with a Microfluidic Device, Development, 2016, vol. 143(11), pp. 1884-1892.

Kauffman et al., Alternative functional in vitro models of human intestinal epithelia, frontiers in Pharmacology, Jul. 2013, vol. 4, Article 79, 18 pages.

Kelamangalath et al. k-Opioid receptor inhibition of calcium oscillations in spinal cord neurons,, Molecular Pharmacology, 2011, 79:1061-1071.

Kwasny et al., Static biofilm cultures of gram-positive pathogens grown in a microtiter format used for anti-biofilm drug discovery, Current Protocols in Pharmacology, 2010, 13A.8.1-13A.8.23.

Loo et al., An Arduous Journey from Human Pluripotent Stem Cells to Functional Pancreatic Beta Cells, Diabetes Obes Metab., 2018, vol. 20(3), pp. 3-13.

Mcgaugh et al., Efficient Differentiation of Pluripotent Stem Cells to NKX6-1 + Pancreating Progenitors, Journal of Visualized Experiments, 2017, vol. 121, pp. 1-5.

Naik et al., In vitro blood-brain models: Current and perspective technologies, J. Phar Sci., 2012, 1014(4):1337-1354.

Perry et al., The Neuromuscular junction: Structure and function, downloaded from the internet (Neuromuscular junction: Parts, structure and steps/Kenhub>, pp. 1-6, downloaded Feb. 25, 2021.

Polydimethylsiloxane—Wikipedia, dowloaded on Feb. 24, 2021 <Silicon dioxide—Wikipedia>, pp. 1-11.

Ryan et al., Progranulin is expressed within motor neurons and promotes neuronal cell survival, BMC Neuroscience, 2009, 10:130, pp. 1-22.

Sances et al., Modeling ALS with Motor Neurons Derived from Human Induced Pluripotent Stem Cells, Nature Neuroscience , 2016, vol. 19, pp. 542-553.

Santaguida et al., Side By Side Comparison Between Dynamic Versus Static Models of Blood-Brain-Barrier in vitro: A Permeability Study, Brain Research, 2006, vol. 1109(1), pp. 1-13.

Schiesser et al., Derivation of Insulin-Producing Beta-Cells from Human Pluripotent Stem Cells, The Review of Diabetic Studies, 2014, vol. 11(1), pp. 6-18.

Schwartz et al., Allan-Herndon-Dudley Syndrome and the Monocarboxylate Transporter 8 (MCT8) Gene, 2005, AJHG, vol. 77(1), pp. 41-53.

Silicon dioxide—Wikipedia, downloaded on Feb. 24, 21 <silicon dioxide—Wikipedia> pp. 1-20.

Southam et al., Microfluidic primary culture model of the lower motor neuron-neuromuscular junction circuit, J Neurosc Meth 2013, 218:164-169.

Southam et al., A Novel in vitro Primary Culture Model of the Lower Motor Neuron-Nueromuscular Junction Circuit, Microfludic and Compartmentalized Platforms for Neurobiological Research, Humana Press, 2015, pp. 181-193, abstract only.

Uzei et al., Microfluidic Device for the Formation of Optically Excitable, Three-Dimensional, Compartmentalized Motor Units, Science Advances, 2016, pp. e1501429.

Wang et al., Microfluidics: A new cosset for neurobiology, Lab Chip, 2009, 9:644-652.

Wang et al., Generation of an Induced Pluripotent Stem Cell Line (SHCDNi003-A) from a One-Year Old Chinese Han Infant with Allan-Herndon-Dudley Syndrome, Stem Cell Research, 2020, vol. 46, 4 pages.

Yang et al., From the vascular microenvironment to neurogenesis, Brain Res Bull. Jan. 15, 2011; 84(1):1-7.

Munera et al., Differentiation of Human Pluripotent Stem Cells into Colonic Organoids via Transient Activation of BMP Signaling, Cell Stem Cell, 21, 51-64, 2017.

International Search Report and Written Opinion of PCT/US2019/ 26183, Dated Jun. 12, 2019, 10 Pages.

International Search Report and Written Opinion of PCT/US2019/ 026195 Jun. 12, 2019, 10 pages.

(56)          References Cited

OTHER PUBLICATIONS

International Search Report and Written Opinion of PCT/US2019/026193 Jul. 1, 2019, 8 pages.

Kondo, T. et al., Ipsc-based Coound screening and in vitro trials identify a synergistic anti-amyloid b combination for Alzheimer's Disease, Cell Reports, 2017, vol. 21, pp. 2304-2312.

McKinney, C.E. et al., Using induced pluripotent stem cells derived neurons to model brain diseases, Neural Regeneration Research, 2017, 12:7 pp. 1-11.

Li, Y. et al., Protein kinase C controls lysosome biogenesis independently of mTORC1, Nature Cell Biology, 2016, 10:10, pp. 1-26.

Kilpatrick, K. et al., Genetic and chemical activation of TFEB mediates clearance of aggregated a-synuclein, PLoS One, 2015, 10:3, pp. 1-21.

Chou, B.K. et al., Efficient human iPS cell derivation by a non-integrating plasmid from blood cells with unique epigenetic and gene expression signatures, Cell Research, 2011, 21:3, pp. 518-529.

Sundberg, m. et al., Improved cell therapy protocol for Parkinson's Disease based on differentiation efficiency and safety of Hesc-, Hipsc and non-human primate Ipsc-derived DA neurons, Stem Cells, 2013, 31:8, pp. 1-25.

Hoveizi et al., Differential effect of Activin A and WNT3a on definitive endoderm differentiation on electrospun nanofibrous PCL scaffold, Cell Biology International, 2015, 9999, pp. 1-9.

Oceguera-Yanez et al., Engineering the AAVS1 locus for consistent and scalable transgene expression in human IPSCs and their differentiated derivatives, Methods, 2016, 1:43-55.

ISR and WO for PCT/US2021/051492 mailed Dec. 27, 2021, 11 pages.

Lamas et al., Neurotrophic Requirements of Human Motor Neurons Defined Using Amplified and Purified Stem Cell-Derived Cultures, PLosOne, Oct. 22, 2014, vol. 9, No. 10, pp. 1-13.

Li et al., An integrated multi-omic analysis of IPSC-derived motor neurons from C9ORF72 ALS patients, iScience, Oct. 12, 2021, vol. 24, No. 11, pp. 1-33.

EESR for EP 21873328.5 dated Sep. 5, 2024, 9 pages.

Kosar et al., A nanofabricated planar aperture as a mimic of the nerve-muscle contact during synaptogenesis, Lab on a Chip, 2016, 6:632-638.

Guo et al., Neuromuscular junction formation between human stem cell-derived motoneurons and human skeletal muscle in a defined system, Biomaterials, 2011 32:9602-9611.

Adams et al., Development of flexible arrays for in vivo neuronal recording and stimulation, Nuclear Instruments & Methods in Physics Research, 2005, 546:154-159.

Baloh et al., "Transplantation of human neural progenitor cells secreting GDNF into the spinal cord of patients with ALS: a phase 1/2a trial." Nature medicine 28.9 (2022): 1813-1822.

Faravelli et al., "Motor neuron derivation from human embryonic and induced pluripotent stem cells: experimental approaches and clinical perspectives." Stem cell research & therapy 5 (2014): 87.

Klein et al., "GDNF delivery using human neural progenitor cells in a rat model of ALS." Human gene therapy 16.4 (2005): 509-521.

Extended European Search Report in European Patent Application No. 20878850, mailed Dec. 8, 2023 (12 pages).

EPO Communication Article in European Patent Application No. 18802136, mailed Mar. 17, 2023 (10 pages).

Examination Report in Australian Patent Application No. 2017321489, Mailed Mar. 7, 2023 (4 pages).

Sareen et al., Human induced pluripotent stem cells are a novel source of neural progenitor cells (iNPCs) that migrate and integrate in the rodent spinal cord: Human neural progenitor cells, 2014. Journal of Comparative Neurology, vol. 522, No. 12, pp. 2707-2728.

Office Action in Canadian Patent Application No. 3,034,614, mailed Jan. 28, 2025 (3 pages).

Exam Search Report and Written Opinion in Singaporian Patent Application No. 11201901621V, mailed May 12, 2020 (12 pages).

Achyuta A.K.H. et al., A modular approach to create a neurovascular uniton-a-chip. Lab Chip, Sep. 26, 2012, vol. 13, No. 4, pp. 542-553.

EPO Communication in European Patent Application No. 19796470, mailed Jan. 16, 2024 (10 pages).

Klepac et al. "An update on the management of young-onset Parkinson's disease." Degenerative neurological and neuromuscular disease (2013): 53.

Notice of Reasons for Rejection in Japanese Patent Application No. 2020-560894, mailed Apr. 4, 2023 (6 pages).

Wu et al., "Nuclear accumulation of histone deacetylase 4 (HDAC4) exerts neurotoxicity in models of Parkinson's disease." Molecular neurobiology 54 (2017): 6970-6983.

Offica Action in Chinese Patent Application No. 202080074079, mailed Aug. 11, 2023 (11 pages).

Laperle et al., "Human iPSC-derived neural progenitor cells secreting GDNF provide protection in rodent models of ALS and retinal degeneration." Stem cell reports 18.8 (2023): 1629-1642.

Akhtar et al., "Inducible expression of GDNF in transplanted iPSC-derived neural progenitor cells." Stem Cell Reports 10.6 (2018): 1696-1704.

Fernandopulle et al., Transcription factor-mediated differentiation of human iPSCs into neurons, current Protocols in Cell Biology, 2018, 79, e51.

Zhang et al., Molecular biomarkers for embryonic and adult neural stem cell and neurogenesis, BioMed Research International, 2015, vol. 2015, Article ID 727542.

Romero-Ramos et al., Neuronal differentiation of stem cells isolated from adult muscle, Journal of Neuroscience Research, 2002, 69:894-907.

PSA (Aniti-anti) Antibiotic-Antimycotic Solution (100X)-cell culture-TOKU—2 pages downloaded from internet on Jun. 2, 2025, 2025.

Elis et al., Human IPSC-derived myocardium-on-chip with capillary-like flow for personalized mediine, Biomicrofluidics 11, 024105, 2017.

Cardiac cells, Science Direct <https://www.sciencedirect.com/topics/engineering/cardiac-cell>; 2025.

CA Exam Report for CA 3158428 dated Oct. 8, 2025, 5 pages.

Zhou et al., "The positional identity of iPSC-derived neural progenitor cells along the anterior-posterior axis is controlled in a dosage-dependent manner by bFGF and EGF", Differentiation, 92(4), pp. 183-194, Oct. 2016.

Xu et al., "Effect of leukocyte inhibitory factor on neuron differentiation from human induced pluripotent stem cell-derived neural precursor cells", International Journal of Molecular Medicine, 41(4), pp. 2037-2049, Apr. 2018.

McCaughey-Chapman et al., "Human Cortical Neuron Generation Using Cell Reprogramming: A Review of Recent Advances", Stem Cells and Development, 27(24), pp. 1674-1692, Dec. 2018.

Roberts et al., Fluorescent gene tagging of transcriptionally silent genes in hiPSCs, Stem Cell Reports, 2019, 12:1145-1158.

Cell Signaling Technology "Certificate of Analysis" for Product No. 9375, Phospho-PKC alpha/beta II (Thr638/641) antibody, Sep. 5, 2019.

Newton, Protein kinase C: structural and spatial regulation by phosphorylation, cofactors, and macromolecular interactions, Chem Rev. Aug. 2001; 101(8):2353-64.

Laperle et al., iPSC modeling of young-onset Parkinson's disease reveals a molecular signature of disease and novel therapeutic candidates, Nat Med. Feb. 2020;26(2):289-299.

* cited by examiner

FIG. 1

| Patient | KB | BH | CR |
|---|---|---|---|
| Age | 32 | 37 | 39 |
| Gender | F | M | M |
| PD Duration | 1.5 | 5 | 4 |
| Motor subtpe | Mixed | Mixed | Tremor-predominant |
| Hoen & Yahr | 1 | 1 | 1 |
| Reported Family history of PD/Tremor | None | None | None |
| PD SNP Familial Mutation | Negative | Negative | Negative |
| DaTscan Results | Positive | Positive | Positive |
| IPSC Line | 190iPD | 194iPD | 200iPD |

| Patient | CTRL 1 | CTRL 2 | CTRL 3 |
|---|---|---|---|
| Sex | M | M | M |
| Age at Collection | 51 | 37 | 6 |
| Sample Type | Blood (T Fraction) | Blood (NT Fraction) | Fibroblast |
| iPSC Line | 02iCTR | WP3iCTR | 00iCTR |

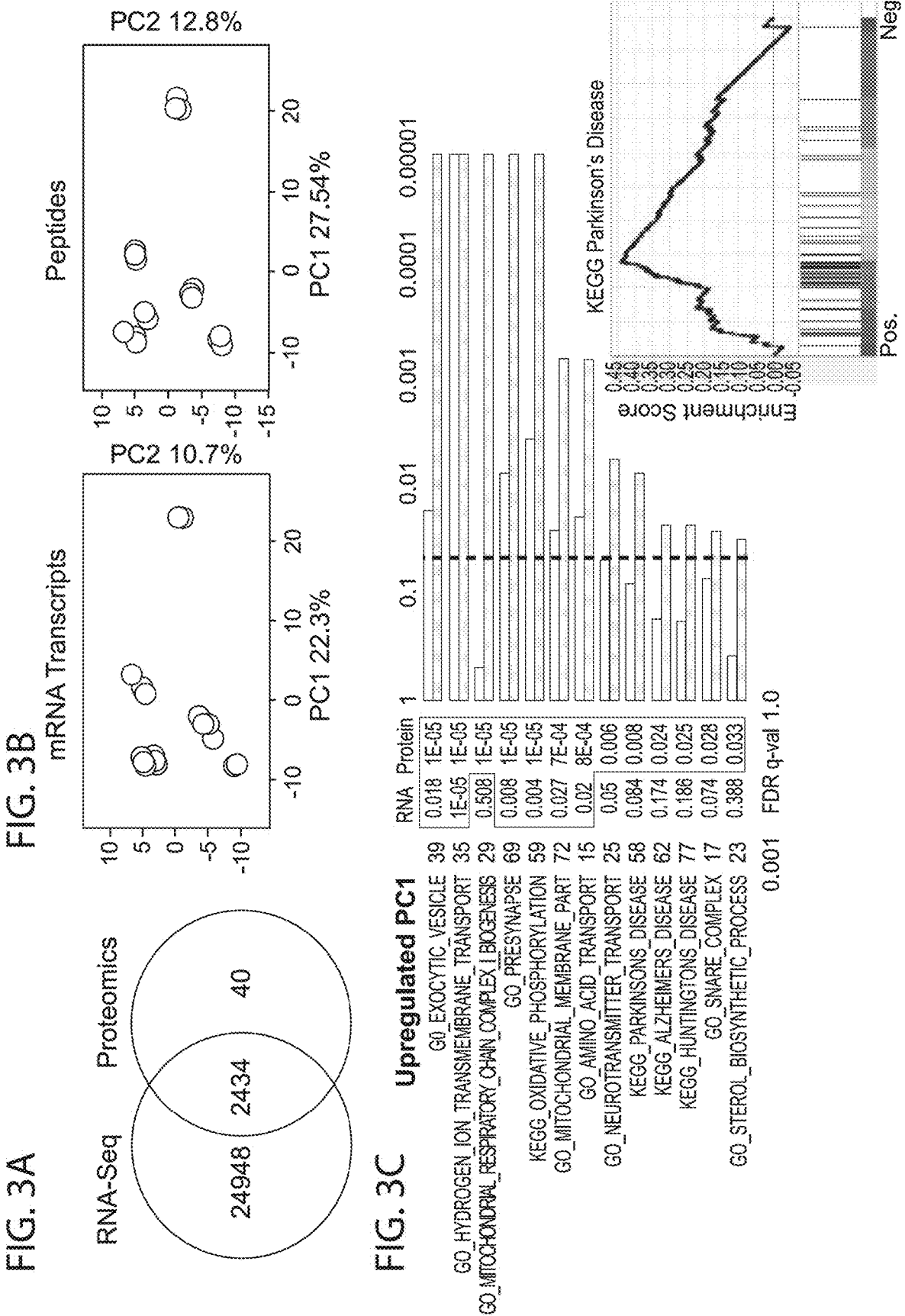

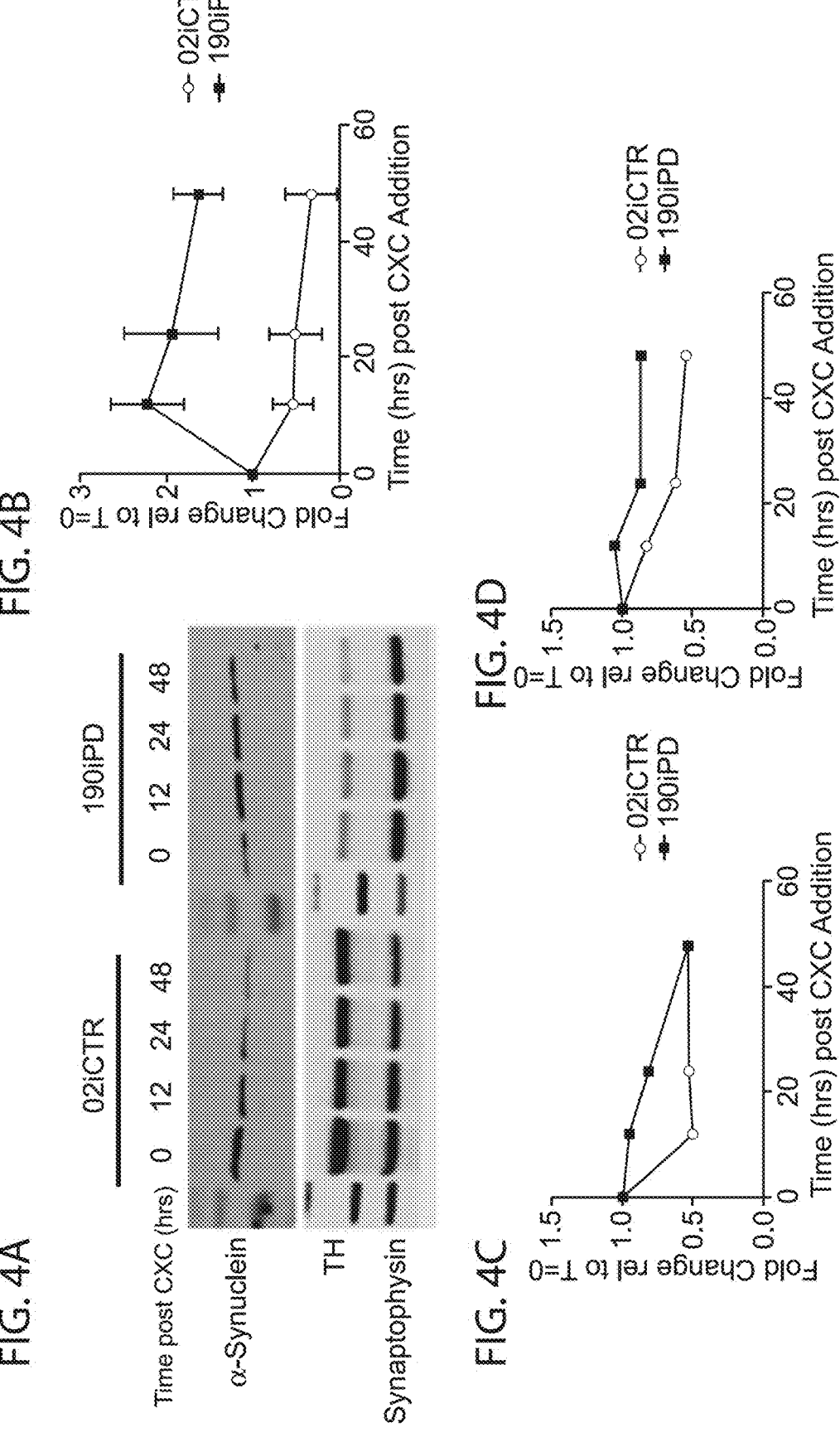

FIG. 4G
FIG. 4F
FIG. 4E
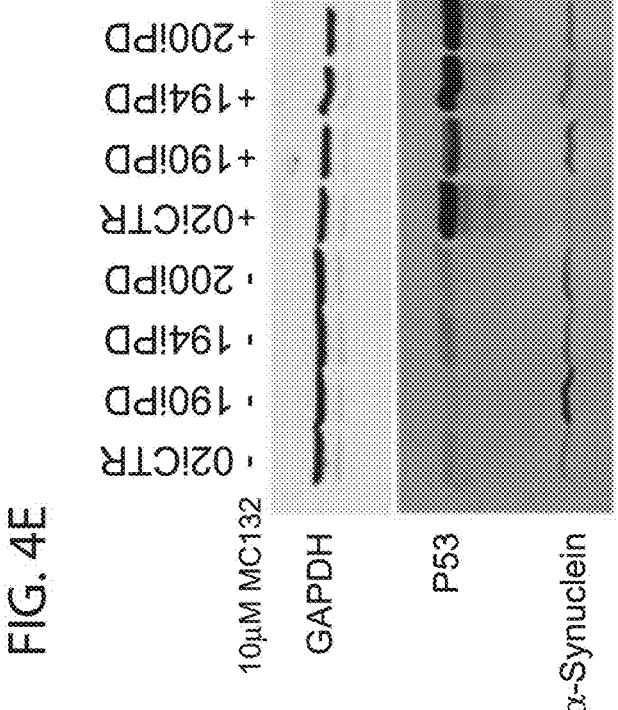
FIG. 4H
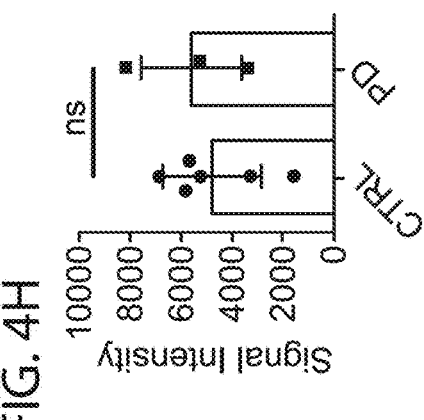

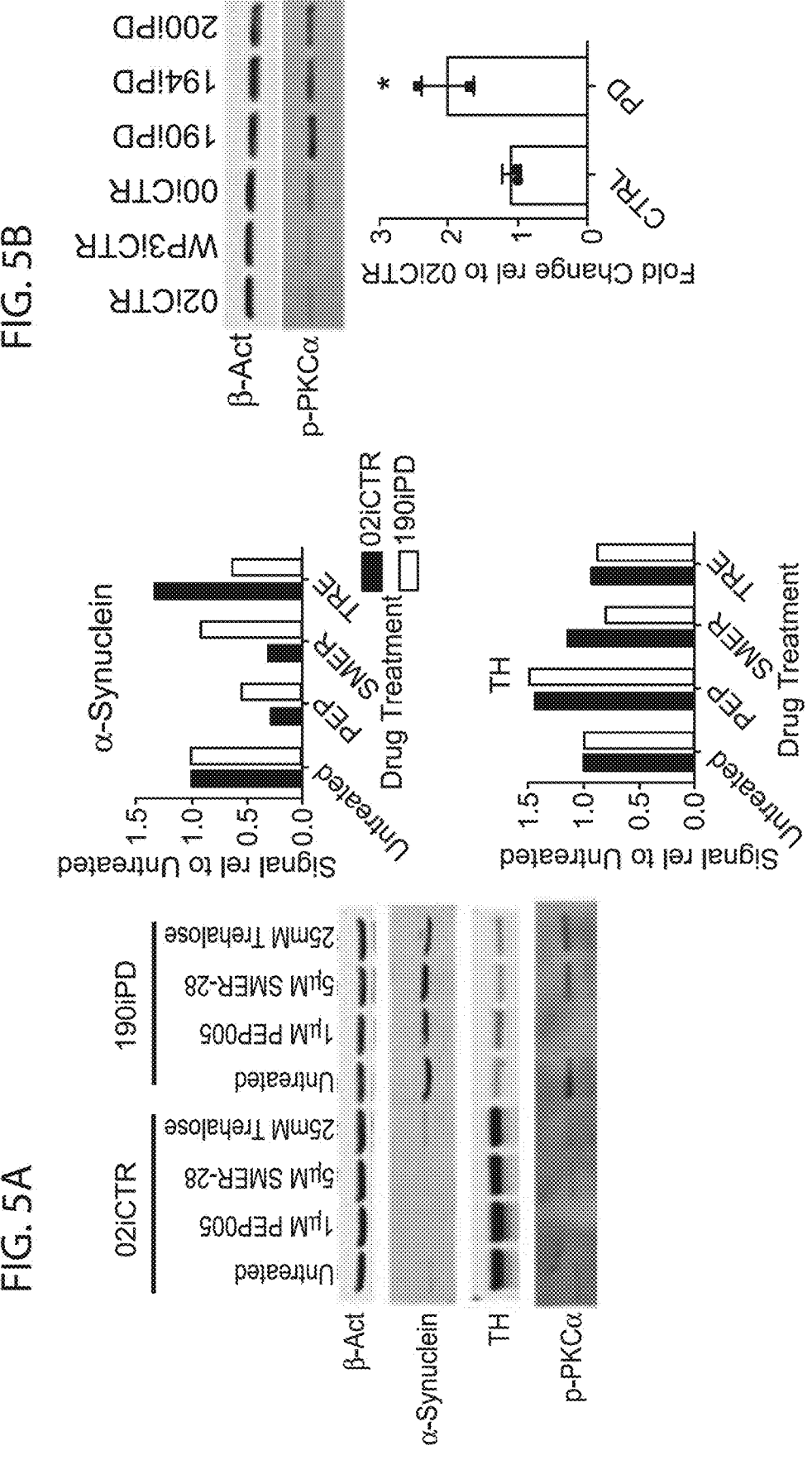

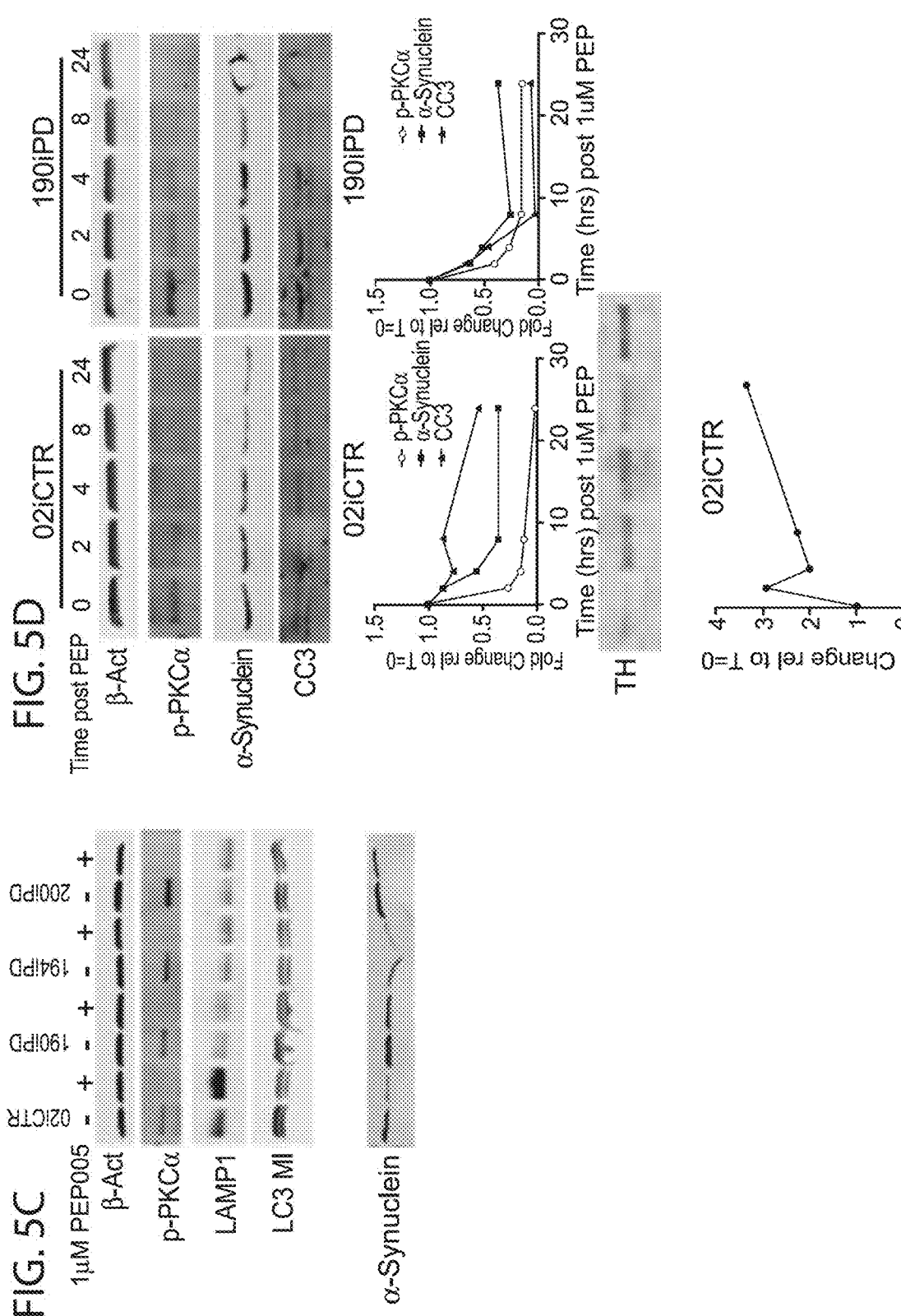

Media E8 + Y27632    Stage 1    Stage 2    Stage 3    Stage 4

Seed at 200k/cm^2

=Stage 1 Feed 3 ml/well each day

=Stage 2 Feed 3 ml/well each day

=Stage 3 Feed 3 ml/well each day

=Stage 4 Feed 3 ml/well each day

=Maturation Media Feed 3ml/6well or 2 ml/24 well every 3rd day, Maturation media good for ~2 weeks Make media at the beginning of each stage, Maturation media good for ~2 weeks

| D14 | D15 | D16 | D17 | D18 | D19 | D20 | D21 | D22 | D23 | D24 | D25 |

Accutase Split*, replate 100k/cm^2 onto matrigel or stage 4 astrocytes**

Maturation Media seed Stage 3 Astrocytes 7 days prior

- Early onset PD < 50 YOA

- EOPD represents ~10% of all PD patients

- Of EOPD patients > 80% are sporadic

FIG. 10

| Clinical Features | Subject 1 | Subject 2 | Subject 3 | Subject 4 | Subject 5 |
|---|---|---|---|---|---|
| Gender | F | M | M | M | F |
| Age of onset | 30 | 32 | 34 | 47 | 41 |
| Family History of PD | None | None | None | None | None |
| Monogenic PD Mutations | Negative | Negative | Negative | Untested | Untested |
| Sample type | Blood (T fraction) | Blood (T fraction) | Blood (T fraction) | Blood (T fraction) | Blood (T fraction) |
| iPSC Line | 190iPD | 194iPD | 200iPD | 172iPD | 192iPD |

| Clinical Features | Control 1 | Control 2 | Control 3 | Control 4 | Control 5 | Control 6 |
|---|---|---|---|---|---|---|
| Gender | M | M | M | M | F | F |
| Age at iPSC generation | 51 | 37 | 6 | 83 | 83 | 83 |
| Sample type | Blood (T fraction) | Blood (Non-T fraction) | Fibroblast | Blood (T Fraction) | Blood (T Fraction) | Blood (T Fraction) |
| iPSC Line | 02iCTR | WP3iCTR | 00iCTR | 0771iCTR | 1034iCTR | 1185iCTR |

FIG. 15

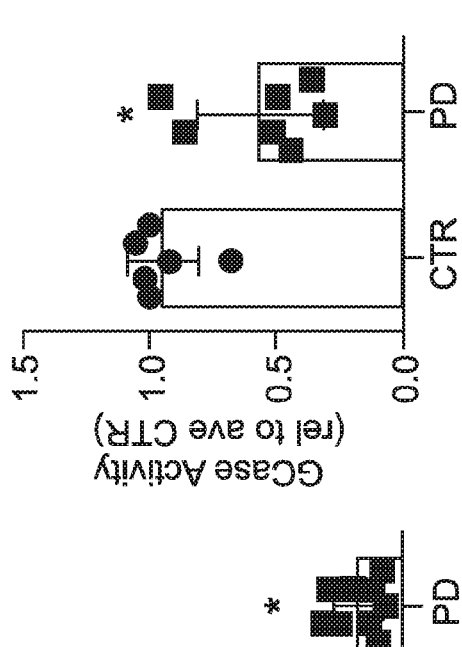
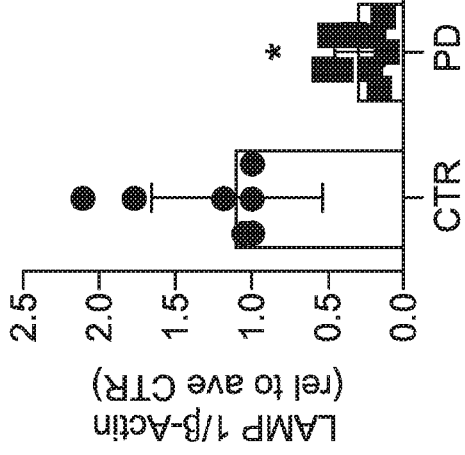
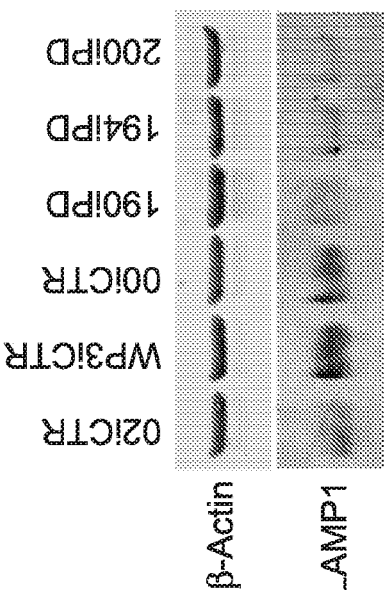
FIG. 16

FIG. 23

FIG. 26
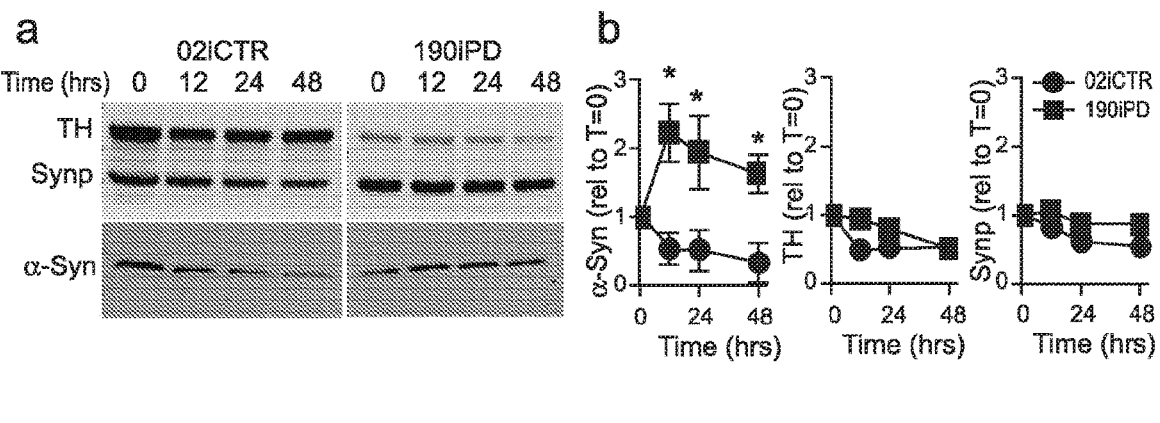
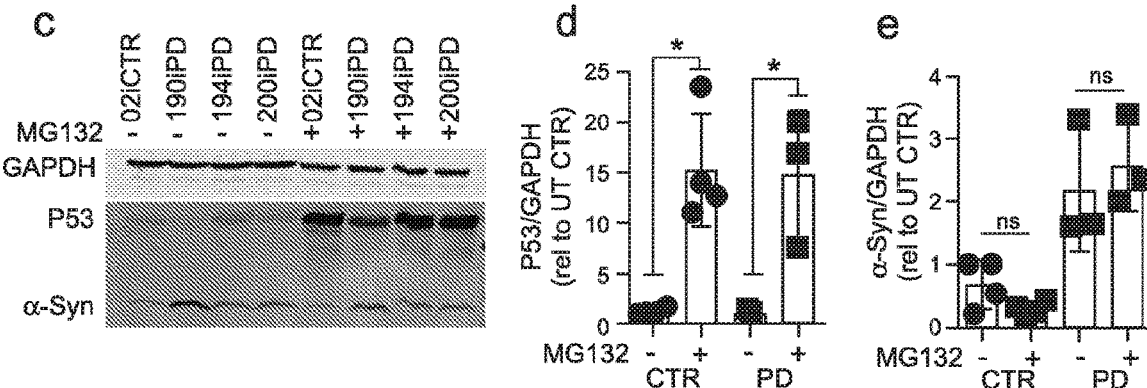
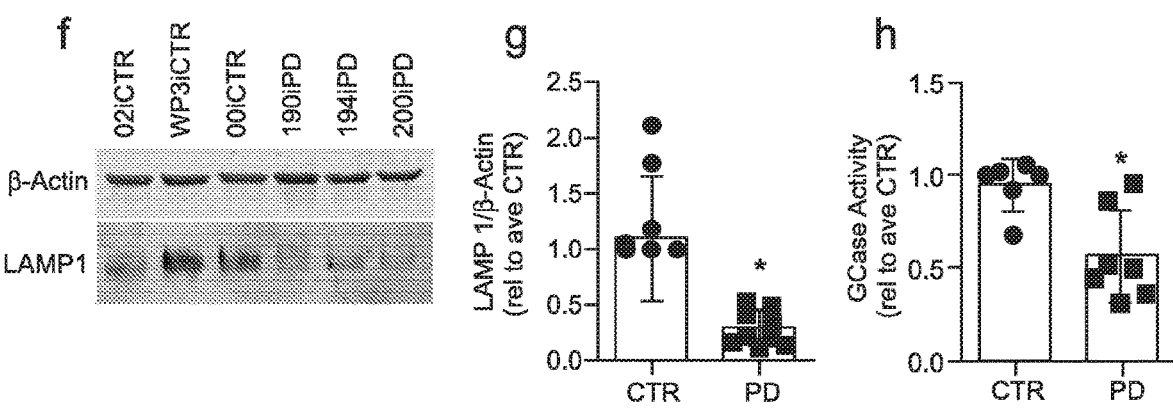
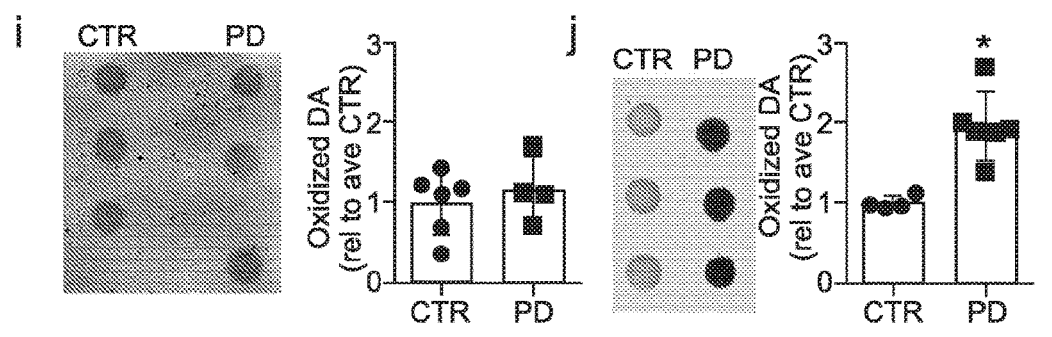

FIG. 30

| Clinical Features | Subject 1 | Subject 2 | Subject 3 | Subject 4 | Subject 5 | Subject 6 |
|---|---|---|---|---|---|---|
| Gender | F | M | M | M | F | M |
| Age of onset | 30 | 32 | 34 | 47 | 41 | 67 |
| PD Duration (yrs) | 1.5 | 5 | 4 | 4 | 3 | |
| Age of iPSC generation | 32 | 37 | 39 | 51 | 44 | 67 |
| Phenotype | Akinetic-Rigid | Mixed | Tremor-predominant | Tremor-predominant | Akinetic-Rigid | |
| Asymmetrical onset | Yes (right) | Yes (right) | Yes (right) | Left | Left | |
| DAT scan abnormality | Yes | Yes | Yes | Yes | Yes | |
| Response to levodopa | Yes | Yes | Yes | Yes | Yes | |
| Family History of PD | None | None | None | None | None | Yes |
| Monogenic PD Mutations | Negative | Negative | Negative | Untested | Untested | Untested |
| Hyposmia | No | No | Yes | | | |
| Constipation | Yes | Yes | No | | | |
| RBD | No | No | Yes | | | |
| Ortostatic Hypotension | No | No | No | | | |
| Depression | Yes | Yes | No | | | |
| Cognitive decline | Yes | Yes | No | | | |
| Sample type | Blood (T fraction) | Blood (T fraction) | Blood (T fraction) | Blood (T fraction) | Blood (T fraction) | Fibroblast |
| iPSC Line | 190iPD | 194iPD | 200iPD | 172iPD | 192iPD | 78iPD |

| Clinical Features | Control 1 | Control 2 | Control 3 | Control 4 | Control 5 | Control 6 |
|---|---|---|---|---|---|---|
| Gender | M | M | M | M | F | F |
| Age at iPSC generation | 51 | 37 | 6 | 83 | 83 | 83 |
| Sample type | Blood (T fraction) | Blood (Non-T fraction) | Fibroblast | Blood (T fraction) | Blood (T fraction) | Blood (T fraction) |
| iPSC Line | 02iCTR | WP3iCTR | 00iCTR | 0771iCTR | 1034iCTR | 1185iCTR |

FIG. 31

Top 20 Downregulated Terms

| NAME | SIZE | ES | NES | NOM p-val | FDR q-val | FWER p-val | RANK AT MAX |
|---|---|---|---|---|---|---|---|
| GO_MICROTUBULE_BUNDLE_FORMATION | 58 | 0.8016834 | 2.054898 | 0 | 0 | 0 | 3304 |
| GO_AXONEME_ASSEMBLY | 36 | 0.85474586 | 2.043947 | 0 | 0 | 0 | 2799 |
| GO_CILIUM_MOVEMENT | 32 | 0.8530499 | 1.995047 | 0 | 0 | 0 | 3304 |
| GO_DOPAMINERGIC_NEURON_DIFFERENTIATION | 28 | 0.86144125 | 1.9729592 | 0 | 0 | 0 | 422 |
| GO_CILIUM_MORPHOGENESIS | 185 | 0.68267757 | 1.9631314 | 0 | 1.98E-04 | 0.001 | 3751 |
| GO_CILIUM_ORGANIZATION | 169 | 0.67708351 | 1.9446292 | 0 | 1.65E-04 | 0.001 | 3732 |
| GO_CILIARY_PLASM | 73 | 0.73292863 | 1.9274043 | 0 | 1.42E-04 | 0.001 | 3340 |
| GO_AXONEME_PART | 20 | 0.88905951 | 1.9183128 | 0 | 3.68E-04 | 0.003 | 1769 |
| GO_POSITIVE_REGULATION_OF_STEM_CELL_DIFFERENTIATION | 49 | 0.76073384 | 1.9050289 | 0 | 5.44E-04 | 0.005 | 3643 |
| GO_ORGAN_GROWTH | 66 | 0.72163314 | 1.8848537 | 0 | 0.001076789 | 0.01 | 1584 |
| GO_CELLULAR_COMPONENT_ASSEMBLY_INVOLVED_IN_LUNG_MORPHOGENESIS | 227 | 0.6370468 | 1.8630521 | 0 | 0.00195453 | 0.021 | 3732 |
| GO_LUNG_MORPHOGENESIS | 45 | 0.74786574 | 1.8569834 | 0 | 0.002039077 | 0.024 | 3379 |
| GO_RESPIRATORY_SYSTEM_DEVELOPMENT | 196 | 0.64352244 | 1.8548173 | 0 | 0.002110945 | 0.027 | 3021 |
| GO_REGULATION_OF_EPITHELIAL_TO_MESENCHYMAL_TRANSITION | 65 | 0.70723591 | 1.8534863 | 0 | 0.0020303.05 | 0.028 | 3453 |
| GO_POSITIVE_REGULATION_OF_ALPHA_BETA_T_CELL_PROLIFERATION | 19 | 0.8656217 | 1.8533652 | 0 | 0.001894951 | 0.028 | 510 |
| GO_MOTILE_CILIUM | 99 | 0.57612021 | 1.8480052 | 0 | 0.002449211 | 0.039 | 2676 |
| GO_EPITHELIAL_TUBE_BRANCHING_INVOLVED_IN_LUNG_MORPHOGENESIS | 25 | 0.8188359 | 1.842965 | 0 | 0.002650158 | 0.045 | 2608 |
| GO_REGULATION_OF_STEM_CELL_DIFFERENTIATION | 111 | 0.66928166 | 1.8385961 | 0 | 0.002936888 | 0.053 | 3453 |
| GO_POSITIVE_REGULATION_OF_EPITHELIAL_TO_MESENCHYMAL_TRANSITION | 33 | 0.7705659 | 1.8350096 | 0 | 0.002991909 | 0.056 | 3453 |
| GO_AXONEMAL_DYNEIN_COMPLEX_ASSEMBLY | 18 | 0.89570021 | 1.8320527 | 0 | 0.003133505 | 0.062 | 2639 |

Top 20 Upregulated Terms

| NAME | SIZE | ES | NES | NOM p-val | FDR q-val | FWER p-val | RANK AT MAX |
|---|---|---|---|---|---|---|---|
| GO_EXOCYTIC_VESICLE_MEMBRANE | 56 | -0.76396424 | -2.34935 | 0 | 0 | 0 | 3324 |
| GO_PRESYNAPSE | 278 | -0.6023617 | -2.3467247 | 0 | 0 | 0 | 3335 |
| GO_SYNAPTIC_MEMBRANE | 253 | -0.5881974 | -2.2813227 | 0 | 0 | 0 | 3054 |
| GO_PRESYNAPTIC_PROCESS_INVOLVED_IN_SYNAPTIC_TRANSMISSION | 112 | -0.6300227 | -2.2216756 | 0 | 0 | 0 | 1822 |
| GO_SYNAPTIC_SIGNALING | 416 | -0.5565259 | -2.2194529 | 0 | 0 | 0 | 3126 |
| GO_PRESYNAPTIC_ACTIVE_ZONE | 28 | -0.87196087 | -2.21288 | 0 | 1.73E-04 | 0.001 | 1661 |
| GO_PRESYNAPTIC_MEMBRANE | 53 | -0.73016983 | -2.2020907 | 0 | 3.00E-04 | 0.002 | 2878 |
| GO_EXOCYTIC_VESICLE | 140 | -0.6071259 | -2.1929407 | 0 | 2.63E-04 | 0.002 | 3335 |
| GO_NEUROTRANSMITTER_TRANSPORT | 151 | -0.5821700 7 | -2.1199322 | 0 | 5.96E-04 | 0.005 | 1911 |
| GO_POSTSYNAPTIC_MEMBRANE | 200 | -0.56747544 | -2.1184075 | 0 | 5.36E-04 | 0.005 | 3054 |
| GO_REGULATION_OF_POSTSYNAPTIC_MEMBRANE_POTENTIAL | 55 | -0.67059153 | -2.112724 | 0 | 4.88E-04 | 0.005 | 3076 |
| GO_NEURONAL_CELL_BODY_MEMBRANE | 20 | -0.8411798 | -2.110995 | 0 | 4.47E-04 | 0.005 | 2988 |
| GO_GLUTAMATE_SECRETION | 28 | -0.78370124 | -2.1071572 | 0 | 4.13E-04 | 0.005 | 3246 |
| GO_POSTSYNAPSE | 368 | -0.5209942 | -2.0977168 | 0 | 6.08E-04 | 0.008 | 3060 |
| GO_NEURON_PROJECTION_TERMINUS | 126 | -0.58788025 | -2.0781355 | 0 | 7.87E-04 | 0.011 | 2723 |
| GO_GABA_RECEPTOR_COMPLEX | 18 | -0.8394702 | -2.0707843 | 0 | 8.08E-04 | 0.012 | 2898 |
| GO_GLUTAMATE_RECEPTER_SIGNALING_PATHWAY | 41 | -0.6967954 | -2.0449016 | 0 | 0.001460181 | 0.023 | 3060 |
| GO_NEURON_NEURON_SYNAPTIC_TRANSMISSION | 56 | -0.6684236 | -2.0264523 | 0 | 0.001847369 | 0.031 | 4419 |
| GO_TERMINAL_BOUTON | 63 | -0.6363248 | -2.0250604 | 0 | 0.001917404 | 0.034 | 2557 |
| GO_MODULATION_OF_SYNAPTIC_TRANSMISSION | 293 | -0.5299329 | -2.015885 | 0 | 0.002244042 | 0.042 | 3422 |

FIG. 36

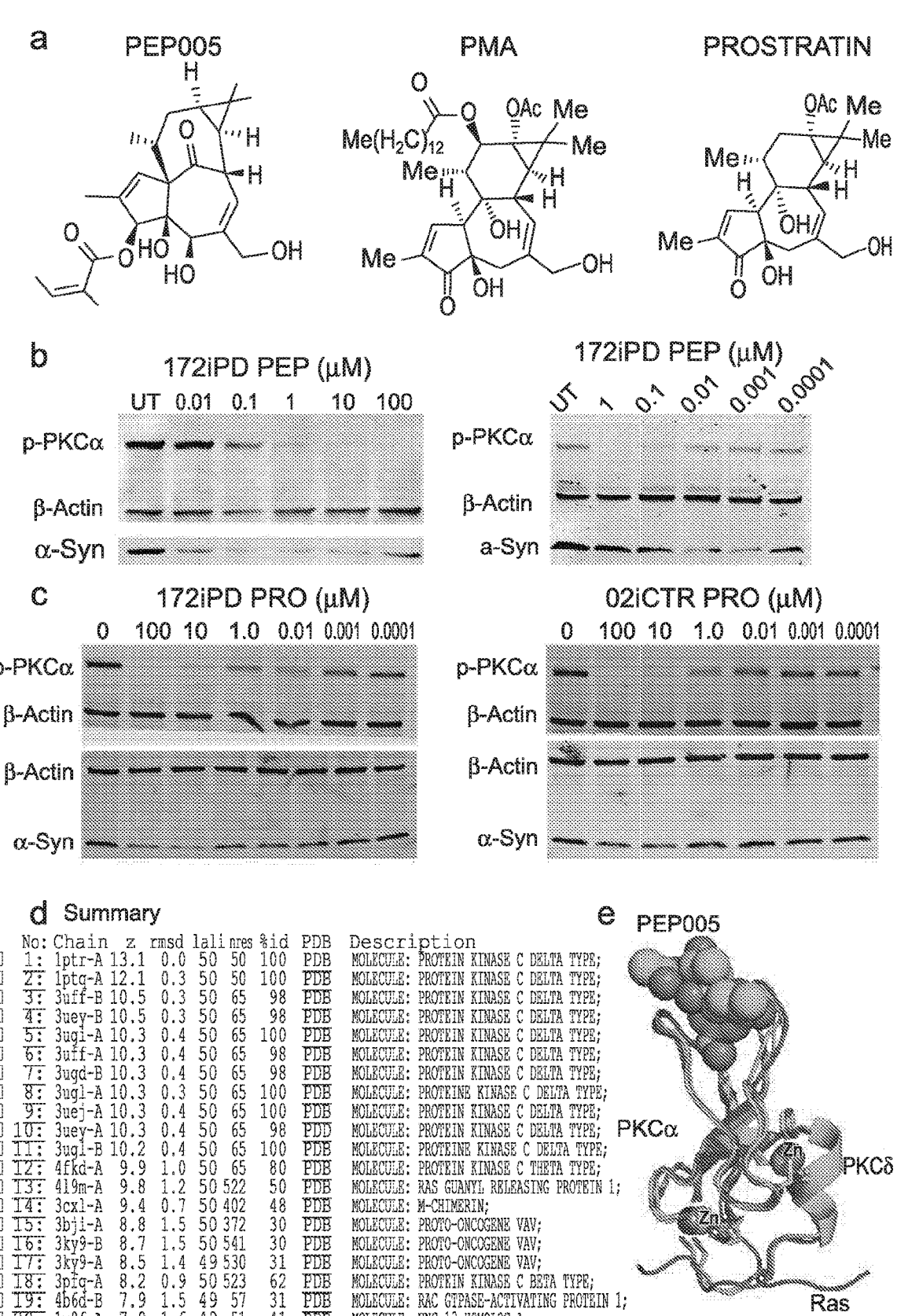

d Summary

| No: | Chain | z | rmsd | lali | nres | %id | PDB | Description |
|---|---|---|---|---|---|---|---|---|
| 1: | 1ptr-A | 13.1 | 0.0 | 50 | 50 | 100 | PDB | MOLECULE: PROTEIN KINASE C DELTA TYPE; |
| 2: | 1ptq-A | 12.1 | 0.3 | 50 | 50 | 100 | PDB | MOLECULE: PROTEIN KINASE C DELTA TYPE; |
| 3: | 3uff-B | 10.5 | 0.3 | 50 | 65 | 98 | PDB | MOLECULE: PROTEIN KINASE C DELTA TYPE; |
| 4: | 3uey-B | 10.5 | 0.3 | 50 | 65 | 98 | PDB | MOLECULE: PROTEIN KINASE C DELTA TYPE; |
| 5: | 3ugi-A | 10.3 | 0.4 | 50 | 65 | 100 | PDB | MOLECULE: PROTEIN KINASE C DELTA TYPE; |
| 6: | 3uff-A | 10.3 | 0.4 | 50 | 65 | 98 | PDB | MOLECULE: PROTEIN KINASE C DELTA TYPE; |
| 7: | 3ugd-B | 10.3 | 0.4 | 50 | 65 | 98 | PDB | MOLECULE: PROTEIN KINASE C DELTA TYPE; |
| 8: | 3ugi-A | 10.3 | 0.3 | 50 | 65 | 100 | PDB | MOLECULE: PROTEINE KINASE C DELTA TYPE; |
| 9: | 3uej-A | 10.3 | 0.4 | 50 | 65 | 100 | PDB | MOLECULE: PROTEIN KINASE C DELTA TYPE; |
| 10: | 3uey-A | 10.3 | 0.4 | 50 | 65 | 98 | PDB | MOLECULE: PROTEIN KINASE C DELTA TYPE; |
| 11: | 3ugi-B | 10.2 | 0.4 | 50 | 65 | 100 | PDB | MOLECULE: PROTEINE KINASE C DELTA TYPE; |
| 12: | 4fkd-A | 9.9 | 1.0 | 50 | 65 | 80 | PDB | MOLECULE: PROTEIN KINASE C THETA TYPE; |
| 13: | 4l9m-A | 9.8 | 1.2 | 50 | 522 | 50 | PDB | MOLECULE: RAS GUANYL RELEASING PROTEIN 1; |
| 14: | 3cx1-A | 9.4 | 0.7 | 50 | 402 | 48 | PDB | MOLECULE: M-CHIMERIN; |
| 15: | 3bji-A | 8.8 | 1.5 | 50 | 372 | 30 | PDB | MOLECULE: PROTO-ONCOGENE VAV; |
| 16: | 3ky9-B | 8.7 | 1.5 | 50 | 541 | 30 | PDB | MOLECULE: PROTO-ONCOGENE VAV; |
| 17: | 3ky9-A | 8.5 | 1.4 | 49 | 530 | 31 | PDB | MOLECULE: PROTO-ONCOGENE VAV; |
| 18: | 3pfq-A | 8.2 | 0.9 | 50 | 523 | 62 | PDB | MOLECULE: PROTEIN KINASE C BETA TYPE; |
| 19: | 4b6d-B | 7.9 | 1.5 | 49 | 57 | 31 | PDB | MOLECULE: RAC GTPASE-ACTIVATING PROTEIN 1; |
| 20: | 1y8f-A | 7.9 | 1.6 | 49 | 51 | 41 | PDB | MOLECULE: UNC-13 HOMOLOG A; |
| 21: | 2eli-A | 7.8 | 0.8 | 50 | 85 | 62 | PDB | MOLECULE: PROTEIN KINASE C ALPHA TYPE; |

Go 6976

Bryostatin 1

FIG. 37

PKC PATHWAY IN PARKINSON'S DISEASE

CROSS-REFERENCE TO RELATED APPLICATIONS

This application is a National Phase of International Application No. PCT/US2019/026193, filed Apr. 5, 2019, which designated the U.S. and that International Application was published under PCT Article 21(2) in English, which claims the benefit under 35 U.S.C. § 119(e) to U.S. Provisional Application Ser. No. Ser. No. 62/664,888 filed Apr. 30, 2018; U.S. Provisional Application Ser. No. 62/664,827 filed Apr. 30, 2018; U.S. Provisional Application Ser. No. 62/664,942 filed May 1, 2018; U.S. Provisional Application Ser. No. 62/755,365 filed Nov. 2, 2018; and U.S. Provisional Application Ser. No. 62/816,795 filed Mar. 11, 2019, the contents of which are incorporated herein by reference in their entirety.

STATEMENT REGARDING FEDERALLY-SPONSORED RESEARCH OR DEVELOPMENT

This invention was made with government support under Grant No. NS105703 awarded by the National Institutes of Health. The government has certain rights in the invention.

FIELD OF THE INVENTION

Described herein are methods and compositions related to production of midbrain neurons, including those related to Parkinson's Disease.

BACKGROUND

Parkinson's Disease (PD) is the second most commonly diagnosed neurodegenerative disorder and represents a substantial economic burden among current aging populations. The classically associated pathology in PD is characterized by the progressive loss of dopaminergic neurons (DaNs) in the substantia nigra pars compacta and the presence of cytoplasmic inclusions known as Lewy bodies and Lewy neurites. These inclusions are composed mainly of the protein α-synuclein. Mutations or triplication of the gene encoding α-synuclein (SNCA) are causal in these specific familial PD cases. In its native state, α-synuclein is found in the presynaptic terminal of neurons throughout the human brain and functions in vesicle trafficking, neurotransmitter release and reuptake.

While many genes and proteins, such as α-synuclein, have been linked to PD, the inability to extract live neurons from patients and the lack of effective PD models leaves unanswered questions regarding the initiation and progression of the disease. Reprogramming patient-derived cells into iPSCs enables the observation of disease progression and pathological phenotypes at a molecular level. Interestingly, previous iPSC studies on the larger non-familial (sporadic) population do not show overt differences when compared those derived from control individuals. Thus, there is a great need in the art for iPSC disease models that represent the complex biological background underpinning Parkinson's disease pathology.

Described herein are compositions and methods for modeling and treating Parkinson's Disease. Importantly, generation of midbrain neurons, floorplate induction in a manner faithfully mirroring development allows for identification of cellular cues leading to neurodegeneration, this includes the complex etiology behind sporadic PD cases that have not yet been fully utilized in iPSC models. Establishing such models, the Inventors herein identified hereto unknown role of α-synuclein and lysosomal degradation dysfunction, as mediated in-party by PKC. Targeting PKC via an agonist improved measurable outcomes, thereby suggesting new therapeutic avenues for Parkinson's Disease.

BRIEF DESCRIPTION OF THE FIGURES

FIG. 1: PD patient data

FIGS. 3A, 3B, 3C, and 3D: Combined detection of overlapping transcripts and proteins from paired RNA-Seq and Proteomics (a). PCA plots of matched transcriptomic and proteomic data (b) GSEA analyses of PC1 components upregulated in PD (c) GSEA analysis of PC1 components downregulated in PD (d)

FIGS. 4A, 4B, 4C, 4D, 4E, 4F 4G, and 4H: representative western blot showing synuclein degradation under cycloheximide inhibition (a). average intensities of 3 separate differentiations and western blots from 02iCTR and 190iPD cells, presented as a fold change to time=0 synuclein (b), Synaptophysin (c), and TH (d). Western blot showing synuclein degradation under 24 hrs of MG132 proteosomal inhibitor (e). Western blot showing reduced LAMP1 protein in PD DaNs (f). GCase activity, each point is an average of 3 separate wells from a single differentiation. Data were normalized to 02iCTR for each differentiation and presented as a fold change (g). NIRF detection of oxidized dopamine from D30 DaN lysates (h)

FIGS. 5A, 5B, 5C, 5D, 5E, 5F, and 5G: Treatment with lysosomal agonists and elevated p-PKCa in PD lines. Western blot and relative band quantifications of d30 DaNs treated with indicated compounds for 72 hours (a). Baseline levels of p-PKCa in d30 DaNs (b). Day 30 DaNs treated with PEP from multiple PD and control lines (c). Timecourse of PEP treatment and synuclein levels (d) Timecourse of PEP treatment SNCA (e) and TH (f) gene expression. Confirmation of elevated synuclein and p-PKCa in addition control and PD lines (g)

FIG. 10: Summary of patient lines. Lines were generated from non-integrating episomal reprogramming from peripheral blood cells. Patients exhibited early onset of PD, no family history NeuroX array and WGS to confirm no causal monogenic PD mutations.

Figure 15:
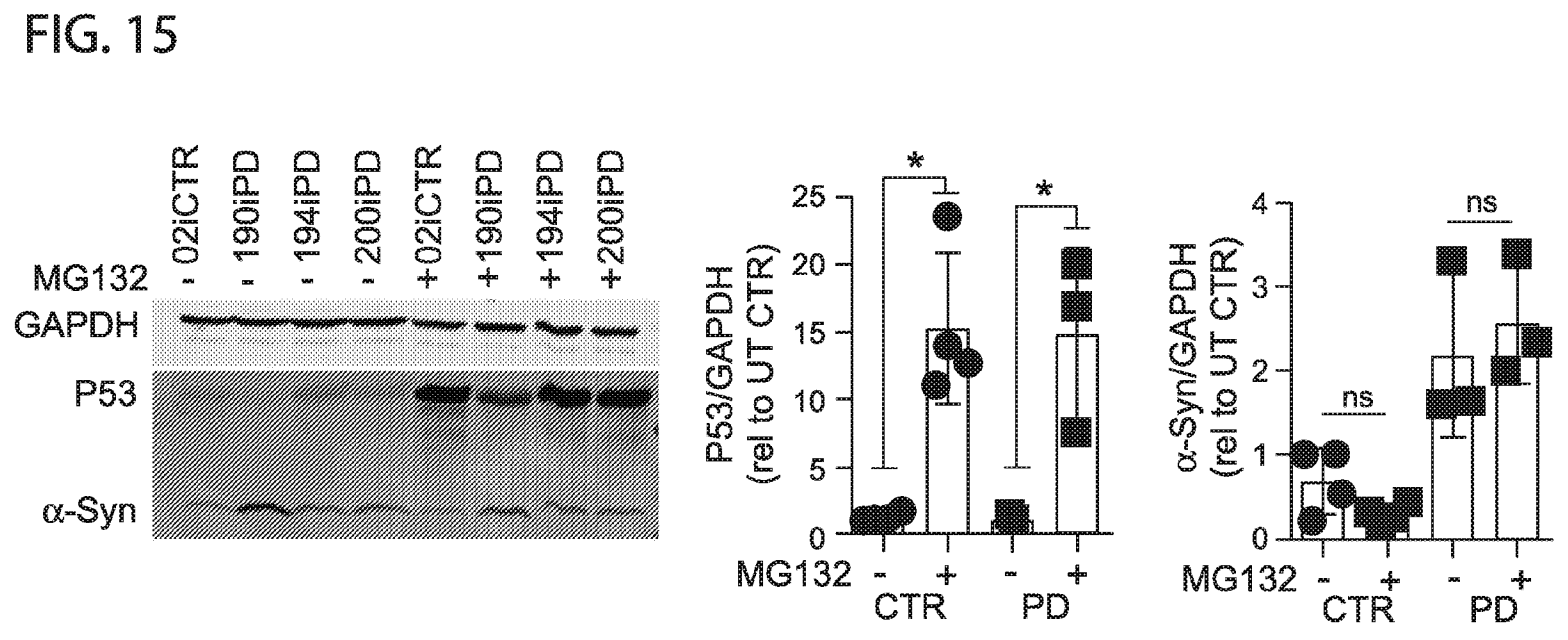

FIG. 15: α-synuclein is not degraded in the proteasome. D30 mDA cultures were treated with proteosomal inhibitor MG132 for 24 hours. P53—canonically degraded by proteosomal means FIG. 16: Lysosomal pathways are impaired in EOSPD mDA cultures. Lysosomal associated membrane protein 1 (LAMP1). GCase—Lysosomal hydrolase.

Figure 23:
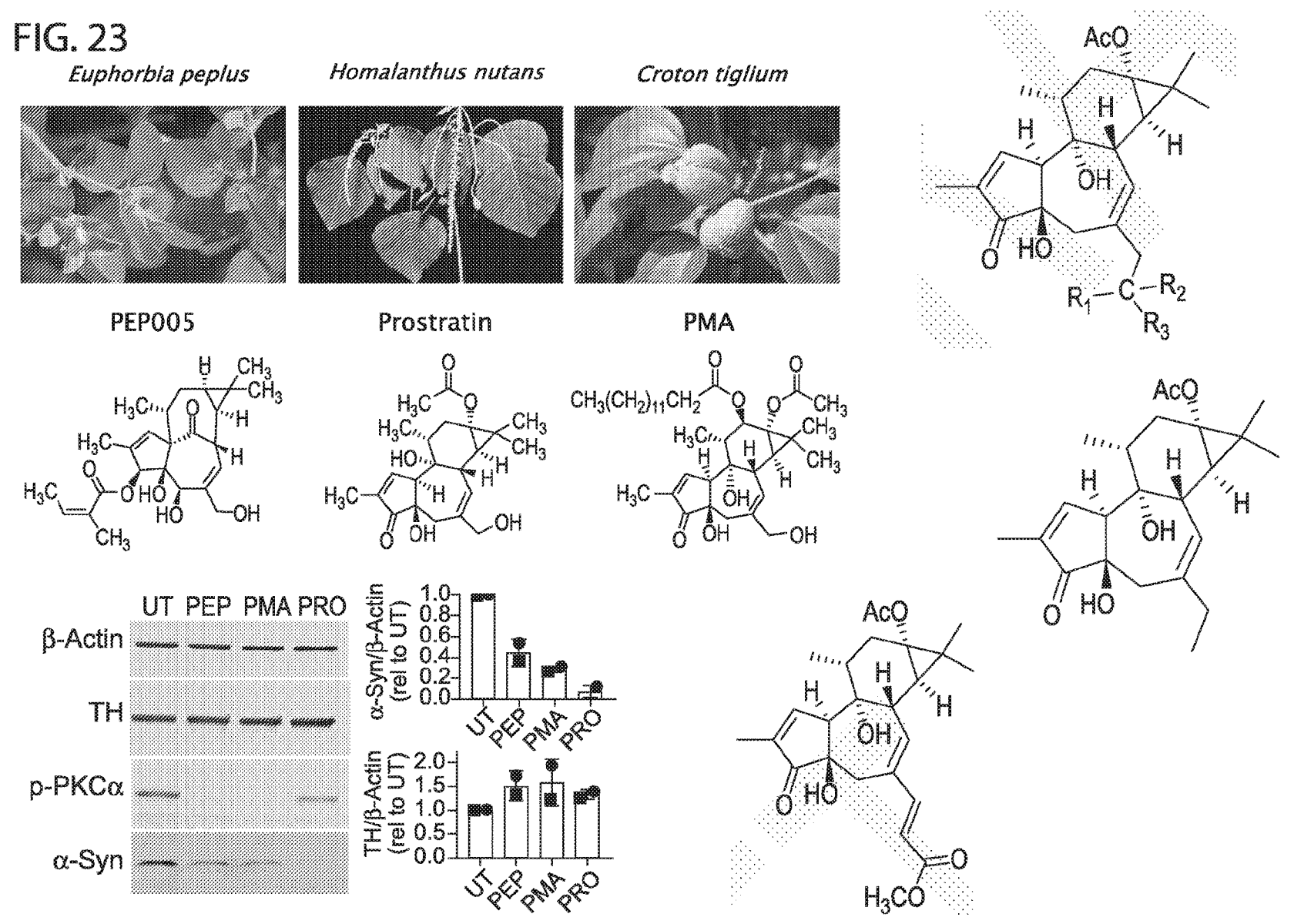

FIG. 23: Additional phorbol ester compounds. PEP005, Prostratin and PMA are all phorbol esters derived from different plant species. Very similar chemical structures. All 3 phorbol ester compounds have a similar effect on synuclein, pPKCa, and TH levels in in vitro tests in our model system

FIG. 26: Lysosomal α-synuclein degradation is specifically impaired in EOSPD mDA cultures. (a) Representative western blot showing tyrosine hydroxylase (TH), synaptophysin (Synp) and α-synuclein (α-Syn) degradation under cycloheximide inhibition. (b) Average intensities of 3 separate differentiations and western blots from 02iCTR and 190iPD cells, presented as a fold change to time=0. * denotes significance (p<0.005) to control cells at the same timepoint via one-way ANOVA (F 15.6, DF 23) with Sidak's multiple comparisons test. (c) Western blot showing α-synuclein degradation under 24 hrs of MG132 proteosomal inhibitor. Quantification of P53 (d) and α-synuclein (e) band intensities after MG132 treatment relative to untreated cells, * indicates significance relative to untreated cells p<0.05 t-test with Welch's correction. (f) Western blot showing LAMP1 protein in EOSPD and control mDA cultures. (g) Quantification of LAMP1 band intensities relative to control cells. Each point represents a separate differentiation and western blot, * indicates significance relative to control cells p<0.005 t-test with Welch's correction. (h) GCase activity, each point is an average of 3 separate wells from a single differentiation. Data were normalized to control cells for each differentiation and presented as a fold change, * indicates significance relative to untreated cells p<0.05 t-test with Welch's correction. NIRF detection of oxidized dopamine from day 30 (i) and day 60 (j) mDA culture lysates. Dot blots and signal intensity relative to control cells are presented. * indicates significance relative to control cells p<0.005 t-test with Welch's correction. Error bars represent standard deviation (SD).

FIG. 30: Clinical summary of EOSPD patients and controls.

FIG. 31: 20 most significant up and down regulated GSEA results for independent RNA-Seq data.

FIG. 36: Dose-response and in silico analysis of PEP005 and related molecules. (a) Structures of Phorbol esters similar to PEP005 tested in mDA cultures. (b) Western blots of α-synuclein and p-PKCα in response to varying PEP005 doses. (c) Western blots of α-synuclein and p-PKCα in response to varying Prostratin (PRO) doses in both EOSPD and control mDA cultures. (d) Predictive modeling of PEP005 binding sites on PKCα and similar affinity sites on additional proteins. (e) 3D model of PEP005 binding sites on PKCα, PKCδ, and Ras overlaid to show similarity.

Figure 37:
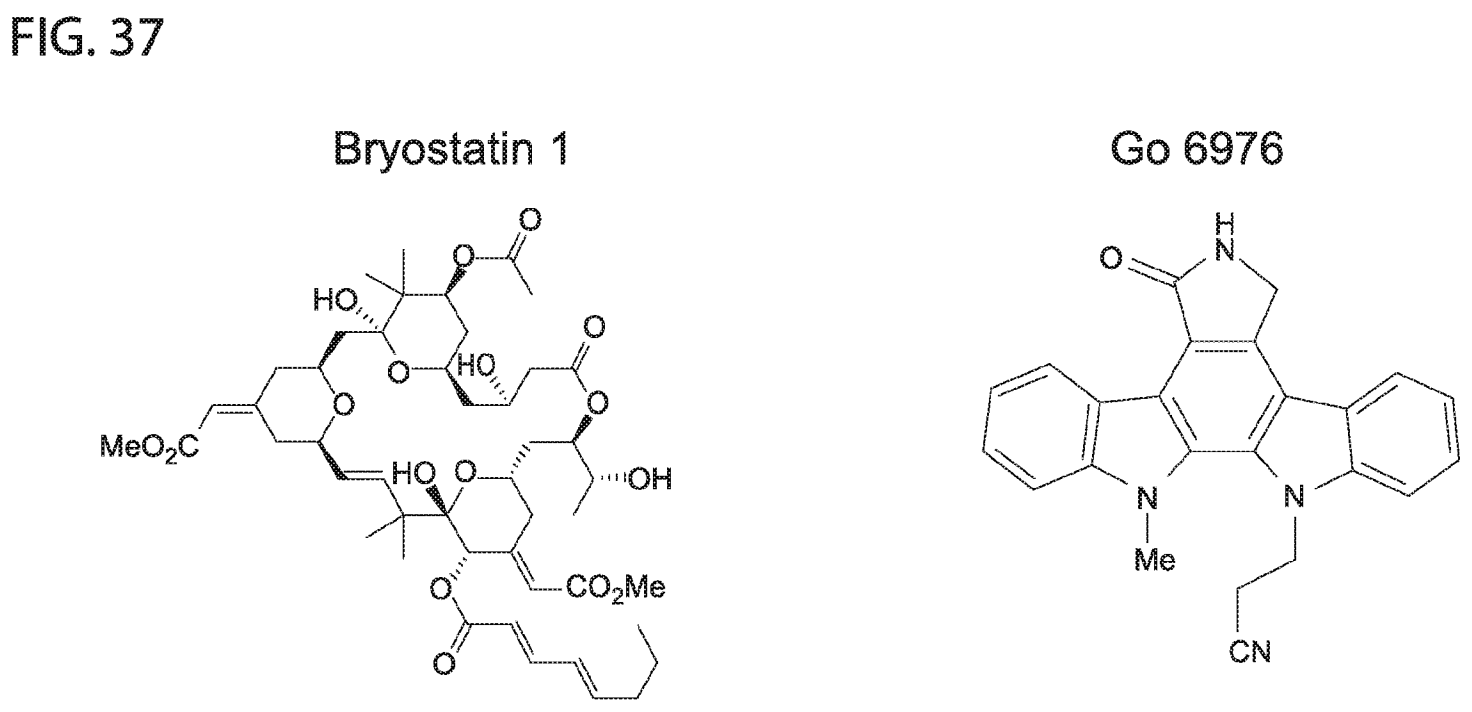

FIG. 37: Bryostatin 1 is a PKC agonist (same class of drug as PEP005) but with a clearly distinct chemical structure. Treatment of D30 mDA neurons with Bryostatin seems to result in a reduction of phospho PKCα as PEP but has unclear effects on synuclein. Go6976 is a PKC antagonist and should have the opposite effect as PEP. Treatment of D30 mDA neurons with Bryostatin did not seem to affect pPKCα or synuclein levels.

SUMMARY OF THE INVENTION

Figures 2A, 2B, 2C:
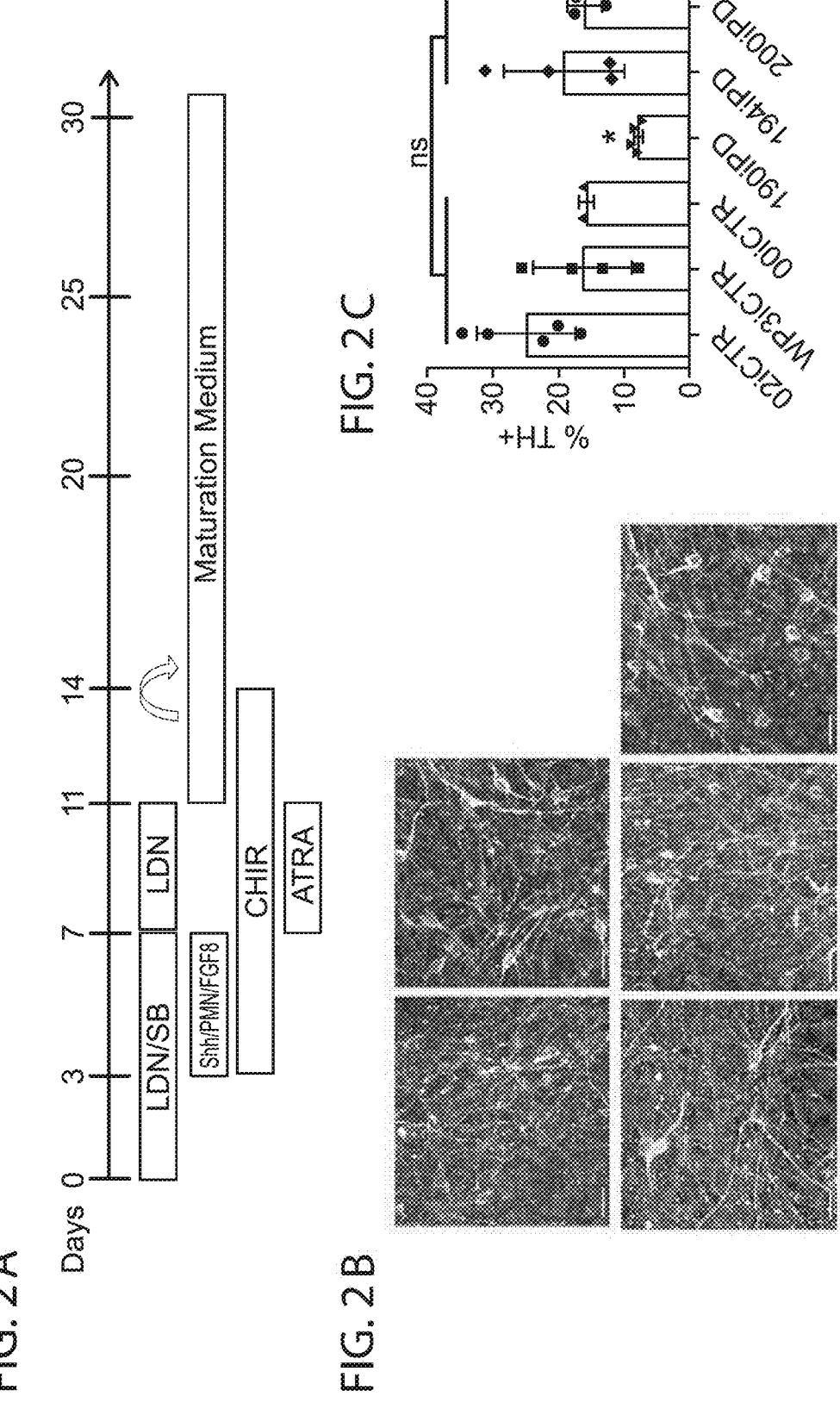
FIGS. 2A, 2B, 2C, 2D, 2E, 2F, 2G, and 2H: Differentiation schematic (a). representative images showing TH expression and morphology (b) Flow cytometry data showing differentiation efficiency, each point represents an average of 3 separate wells of an independent differentiation (c). HLPC detection of total dopamine content (d) and dopamine content normalized to differentiation efficiency by line (e). Western blot showing bACT (housekeeping) and synuclein expression in 30 day old DaNs (f). Relative intensities from multiple western blots, each point is a band from a separate differentiation, colors indicate ipsc lines, data were normalized to 02iCTR for each differentiation (g). SNCA expression by qPCR in 30 day old DaNS (h).

Described herein is a method of treatment, including administering a pharmaceutical composition including a therapeutically effective agent and a pharmaceutically acceptable carrier to a subject afflicted with Parkinson's Disease, thereby treating the subject. In other embodiments, the therapeutically effective agent includes a small molecule. In other embodiments, the small molecule includes a PKC activator, analog and derivative thereof. In other embodiments, the PKC activator includes DAG, DAG lactone, phorbol, ingenol, indolactams, benzolactamm, bryostatin, and calphostin. In other embodiments, the PKC activator analog and derivative thereof include an ingenol derivative. In other embodiments, the ingenol derivative includes ingenol-3-angelate. In other embodiments, the PKC activator, analog and derivative thereof includes a PKC agonist. In other embodiments, the therapeutically effective agent is capable of modulating activity of one or more of: α-synuclein, TFEB, ZKSCAN3, LAMP, GCase, tyrosine hydroxylase (TH) and dopamine. In other embodiments, the therapeutically effective agent is capable of modulating expression of one or more of: α-synuclein, TFEB, ZKSCAN3, LAMP, GCase, tyrosine hydroxylase (TH) and dopamine. In other embodiments, modulating expression includes transcript expression level. In other embodiments, modulating expression includes protein expression level. In other embodiments, protein expression level includes a decrease in α-synuclein protein. In other embodiments, protein expression level includes an increase in TH protein. In other embodiments, the therapeutically effective agent is capable of promoting lysosomal protein degradation. In other embodiments, the therapeutically effective agent is capable of improving coordinated burst of electrical activity.

In other embodiments, the therapeutically effective agent is capable of improving one or more of: stepping, rotational asymmetry, and kinesia.

Described herein is a method of reversing or retarding progression of Parkinson's Disease, including administering a pharmaceutical composition including a therapeutically effective agent and a pharmaceutically acceptable carrier to a subject afflicted with Parkinson's Disease, thereby reversing or retarding progression of Parkinson's Disease in the subject. In other embodiments, the therapeutically effective agent includes a PKC activator, analog and derivative thereof. In other embodiments, the PKC activator, analog and derivative thereof includes ingenol-3-angelate. In other embodiments, the therapeutically effective agent is capable of decreasing α-synuclein protein level. In other embodiments, the therapeutically effective agent is capable of decreasing promoting lysosomal protein degradation. In other embodiments, the therapeutically effective agent is capable of reversing or regarding degeneration of substantia nigra. In other embodiments, the therapeutically effective agent is capable of maintaining or promoting dopamine levels.

DETAILED DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3rd *ed., Revised*, J. Wiley & Sons (New York, NY 2006), and Sambrook and Russel, *Molecular Cloning: A Laboratory Manual* 4th *ed*., Cold Spring Harbor Laboratory Press (Cold Spring Harbor, NY 2012), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

Parkinson's Disease (PD) is one of the most common neurodegenerative disorders characterized by tremor and an inability to initiate movement. The core pathology involves progressive loss of nigral dopamine neurons, and the presence of cytoplasmic inclusions known as Lewy bodies and Lewy neurites. These inclusions consist largely of abnormally aggregated α-synuclein protein. Native state α-synuclein localizes to neuronal presynaptic terminals throughout the brain and functions in vesicle trafficking as well as neurotransmitter release and reuptake. Mutations or triplication of the α-synuclein gene (SNCA) are known to cause PD suggesting that this protein is critical to disease initiation and progression.

The inaccessibility of living dopamine neurons from patients and limitations of animal models inhibit the study of disease and effective drug discovery. Reprogramming patient-derived cells into induced pluripotent stem cells (iPSCs) with subsequent differentiation into dopamine neurons now provides a human tissue-specific model of PD. During the reprogramming process, most epigenetic changes to the cells are wiped clean. New neurons generated from the iPSCs will be immature, yet still reflect the genetics of the patient. While this immaturity is a potential weakness for modeling an adult-onset disease, it is also a strength in that any disease-specific phenotypes present in the cells must originate from the genetic composition of the patient and represent the very earliest stages of the disease process.

There has been an extensive effort to elucidate the role of α-synuclein in the origin and progression of PD using iPSC-based modeling. Several studies have employed iPSCs derived from PD patients with monogenic mutations including a triplication of SNCA, as well as mutations in the LRRK2 and GBA1 genes. While iPSC-derived dopaminergic neural cultures with such monogenic mutations display phenotypic abnormalities and demonstrate accumulation of α-synuclein, these inherited cases represent <10% of all PD patients. iPSC models using the more prevalent sporadic PD population however, do not show accumulation of α-synuclein when compared to control cells.

Ten percent of PD patients are described as early onset, with symptom onset prior to 50 years of age 26. Over 80% of these early onset patients are referred to as sporadic, with no familial history or known PD mutations. The Inventors reasoned that the early onset of disease symptoms may lead to a more severe phenotype in iPSC models, as has been seen previously for early onset diseases such as spinal muscular atrophy.

As described, reprogramming patient-derived cells into iPSCs enables the observation of disease progression and pathological phenotypes at a molecular level. The iPSCs, which are genetically identical to the donor, can be differentiated into DaNs providing a tissue-specific model of Parkinson's Disease in vitro that harbor genetic backgrounds known to relate to clinical presentation in vivo. Recently, an intense effort has been made to elucidate the role of α-synuclein in the origin and progression of PD using similar iPSC modeling techniques. Several studies have employed iPSCs derived from PD patients with monogenic mutations including a triplication of SNCA, as well as mutations in the LRRK2 and GBA1 genes. While DA neurons derived from these iPSC lines display some phenotypic abnormalities and demonstrate accumulation of α-synuclein, familial monogenic mutations are present only in a small minority of PD patients and pathophysiology of these cases are not easily related to the PD population at large. Interestingly, previous iPSC studies on the larger non-familial (sporadic) population do not show overt differences when compared those derived from control individuals.

Here, the Inventors generate iPSC lines from a cohort of early onset sporadic PD (EOSPD) patients. The Inventors hypothesized that these lines represent a promising opportunity to better understand sporadic PD, as early onset sporadic patients could have unknown genetic risk factors that may influence a more aggressive form of the disease. The Inventors show that by comparing differentiated DaNs from either EOSPD patient and non-diseased control lines, aberrant accumulation of α-synuclein protein is indeed specifically reproduced in the PD patient cohort. Molecular and physiological profiling of these tissues including proteomic, whole transcriptomic and enzyme activity assays find dysregulated degradation pathways and implicate a previously unreported upregulation of phosphorylated PKC-α in EOSPD cultures. Finally, by targeting this pathway, the Inventors observe reversal of α-synuclein accumulation after treatment with a small molecule PEP005 both in vitro and in vivo. The iPSC-based model described here provides evidence of the genetic origin of sporadic PD that contributes PD and provides a platform for potential clinical diagnostics and development of new therapeutic targets for EOSPD patients.

Described herein is a method, including: contacting a quantity of blood cells with one or more vectors encoding a reprogramming factor, and delivering a quantity of reprogramming factors into the Hood cells, culturing the blood cells in a reprogramming media, wherein the quantity of blood cells are obtained from a human subject afflicted with a neurodegenerative disease, and further wherein delivering the reprogramming factors, and culturing in a reprogramming media generates blood cell derived induced pluripotent stem cells (iPSCs). In other embodiments, the neurodegenerative disease is Parkinson's disease (PD). In other embodiments, the neurodegenerative disease is early onset PD. In other embodiments, the neurodegenerative disease is familial PD. In other embodiments, the iPSCs are further cultured in fluidic communication with one or more of astrocytes, microglia, and vascular cells. In other embodiments, the one or more vectors are oriP/EBNA1 vectors. In other embodiments, the method includes differentiating the iPSCs into neuron. In other embodiments, the method includes differentiating the iPSCs into vascular cells. In various embodiments, the vascular cells are brain microvascular endothelial cells (BMECs). In other embodiments, the method includes differentiating the iPSCs into astrocytes. In other embodiments, the method includes differentiating the iPSCs into microglia. In other embodiments, the method includes differentiating the iPSCs into neurons, including neurons of the forebrain, midbrain, and/or hindbrain. In various embodiments, the neurons are spinal motor neurons, dopaminergic neurons, or cholinergic neurons. Further information on iPSC reprogramming is found in Barrett, R. et al. Reliable Generation of Induced Pluripotent Stem Cells from Human Lymphoblastoid Cell Lines. *Stem Cells Transl Med.* 2014 December; 3(12):1429-34 and also U.S. Prov. App. No. 62/653,697, U.S. Prov. App. No. 62/755,282, U.S. Prov. App. No. 62/816,785, U.S. Prov. App. No. 62/664,888, U.S. Prov. App. No. 62/664,827, U.S. Prov. App. No. 62/816,795, U.S. Prov. App. No. 62/664,942, U.S. Prov. App. No. 62/755,365, which are fully incorporated by reference herein.

Described herein is a method of treatment, including administering a pharmaceutical composition including a therapeutically effective agent and a pharmaceutically acceptable carrier to a subject afflicted with Parkinson's Disease, thereby treating the subject. In other embodiments, the therapeutically effective agent includes a small molecule. In other embodiments, the small molecule includes a PKC activator, analog and derivative thereof. In other embodiments, the PKC activator includes DAG, DAG lactone, phorbol, ingenol, indolactams, benzolactamm, bryostatin, and calphostin. In other embodiments, the PKC activator analog and derivative thereof include an ingenol derivative. In other embodiments, the ingenol derivative includes ingenol-3-angelate. In other embodiments, the PKC activator, analog and derivative thereof includes a PKC agonist. In other embodiments, the small molecule including a PKC activator, analog and derivative thereof is capable of modulating DAG signalling. In other embodiments, the PKC activator, analog and derivative thereof is specific to a PKC isofom, including for example, conventional, novel, atypica PKC isoforms such as PKC-alpha, PKC-beta1/ beta2, PKC-gamma, among other isoforms known to one of ordinary skill. In various embodiments, the therapeutically effective agent is administered intravenously at a dosage of 0.1-1, 1-5, 5-10, 10-25, 25-50, or 50 or more ug/kg. In various embodiments, the therapeutically effective agent is administered intravenously at a dosage of 5 ug/kg. In various embodiments, the therapeutically effective agent is administered via direct brain infusion at a dosage of 0.1-1, 1-5, 5-10, 10-25, 25-50, or 50 or more ug/kg.

In other embodiments, the therapeutically effective agent is capable of modulating activity of one or more of: α-synuclein, TFEB, ZKSCAN3, LAMP, GCase, tyrosine hydroxylase (TH) and dopamine. In other embodiments, the therapeutically effective agent is capable of modulating expression of one or more of: α-synuclein, TFEB, ZKSCAN3, LAMP, GCase, tyrosine hydroxylase (TH) and dopamine. In other embodiments, modulating expression includes transcript expression level. In other embodiments, modulating expression includes protein expression level. In other embodiments, protein expression level includes a decrease in α-synuclein protein. In other embodiments, protein expression level includes an increase in TH protein. In other embodiments, the therapeutically effective agent is capable of promoting lysosomal protein degradation. In other embodiments, the therapeutically effective agent is capable of improving coordinated burst of electrical activity. In other embodiments, the therapeutically effective agent is capable of improving one or more of: stepping, rotational asymmetry, and kinesia. In various embodiments, the Parkinson's Disease is familial, sporadic, further including early onset sporadic Parkinson's Disease.

Described herein is a method of preventing Parkinson's Disease, including administering to a subject prognosed with a strong likelihood of developing Parkinson's Disease, a prophylactic agent and a pharmaceutically acceptable carrier, thereby preventing Parkinson's Disease. Described herein is a method of reversing or retarding progression of Parkinson's Disease, including administering a pharmaceutical composition including a therapeutically effective agent and a pharmaceutically acceptable carrier to a subject afflicted with Parkinson's Disease, thereby reversing or retarding progression of Parkinson's Disease in the subject. In other embodiments, the prophylactically or therapeutically effective agent includes a PKC activator, analog and derivative thereof. In other embodiments, the PKC activator, analog and derivative thereof includes ingenol-3-angelate. In other embodiments, the prophylactically or therapeutically effective agent is capable of decreasing α-synuclein protein level. In other embodiments, the prophylactically or therapeutically effective agent is capable of decreasing promoting lysosomal protein degradation. In other embodiments, the prophylactically or therapeutically effective agent is capable of reversing or regarding degeneration of substantia nigra. In other embodiments, the therapeutically effective agent is capable of maintaining or promoting dopamine levels. In various embodiments, the subject prognosed with a strong likelihood of developing, or afflicted with Parkinson's Disease includes a human subject possessing one or more mutations in EIFG1, PARK2, LRRK2, GBA, SNCA, PINK1, PARK7, VSP35, ATP13A2 or multiplications of the SNCA locus. In various embodiments, the subject prognosed with a strong likelihood of developing, or afflicted with Parkinson's Disease includes a human subject with reduced DAT signature in the striatum. In various embodiments, the Parkinson's Disease is familial, sporadic, further including early onset sporadic Parkinson's Disease.

Example 1

Generation of iPSCs from Early Onset Sporadic Parkinson's Disease Patients (EO-sPD)

Three early onset sporadic Parkinson's patients between the ages of 30-39 with no reported family history of PD were selected for iPSC production (FIG. 1). Based on analysis with the NeuroX platform, no monogenic mutations in EIFG1, PARK2, LRRK2, GBA, SNCA, PINK1, PARK7, VSP35, ATP13A2 or multiplications of the SNCA locus were detected in the patient lines. All 3 patients demonstrated reduced DAT (phenyltropane) signature in the striatum consistent with their PD diagnosis (FIG. 1). For comparison, 3 control lines were generated from normal individuals with no neurological disease at time of collection.

Peripheral blood mononuclear cells (PBMCs) were collected and subsequently reprogramed to iPSCs using non-integrating episomal techniques (FIG. 1). All iPSC lines were karyotypically normal, and expressed canonical pluripotency markers.

Example 2

Efficient Differentiation of EOSPD iPSCs to DANs

Figure 6A:
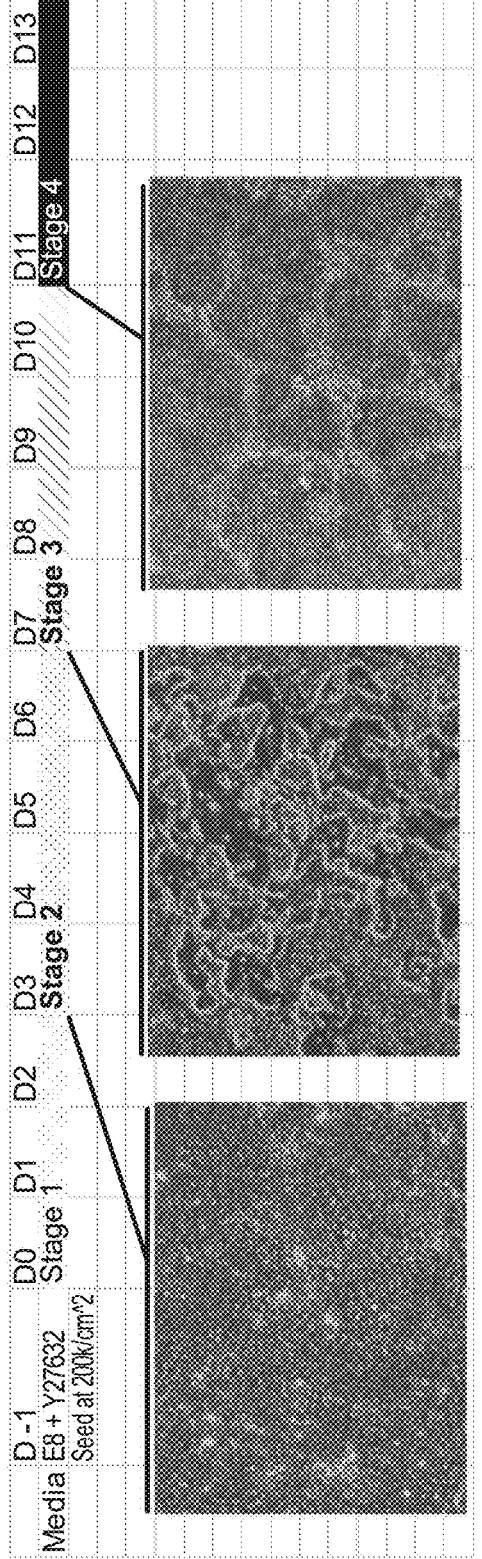
FIGS. 6A and 6B: Differentiation Protocol, including 4 stage time course (a) and maturation (b).
Figure 6B:
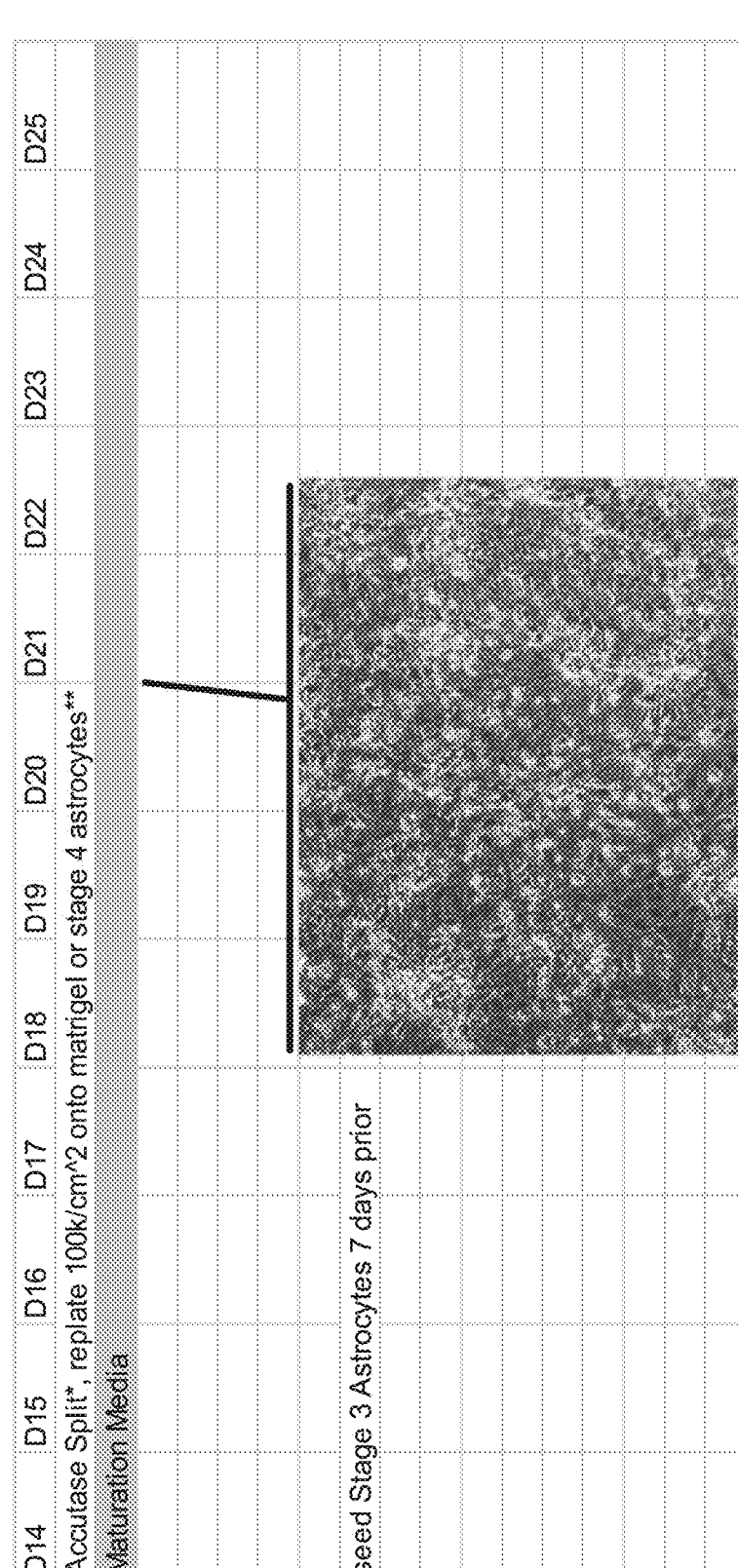
Figure 7:
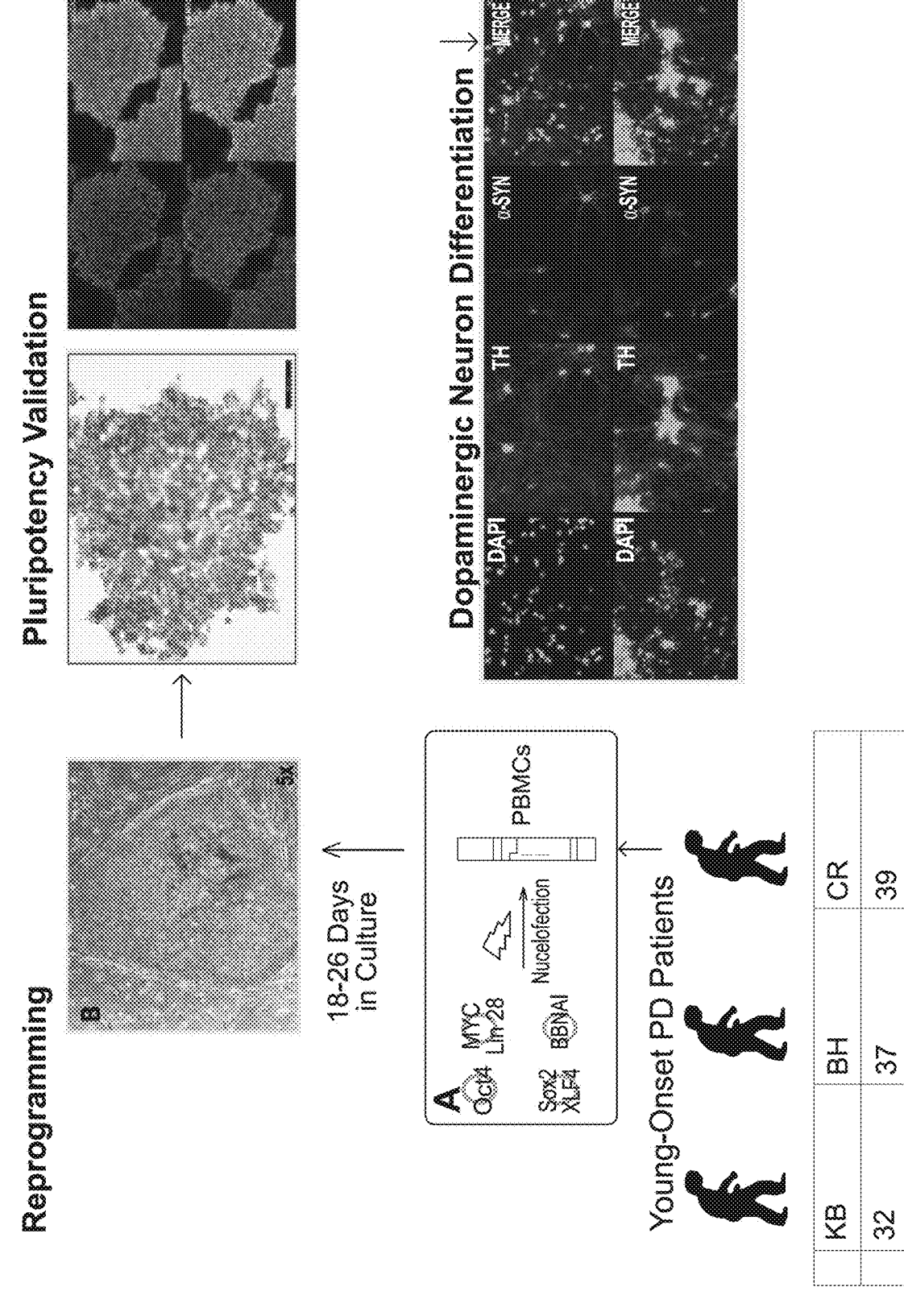
FIG. 7: Study Workflow.
Figure 8:
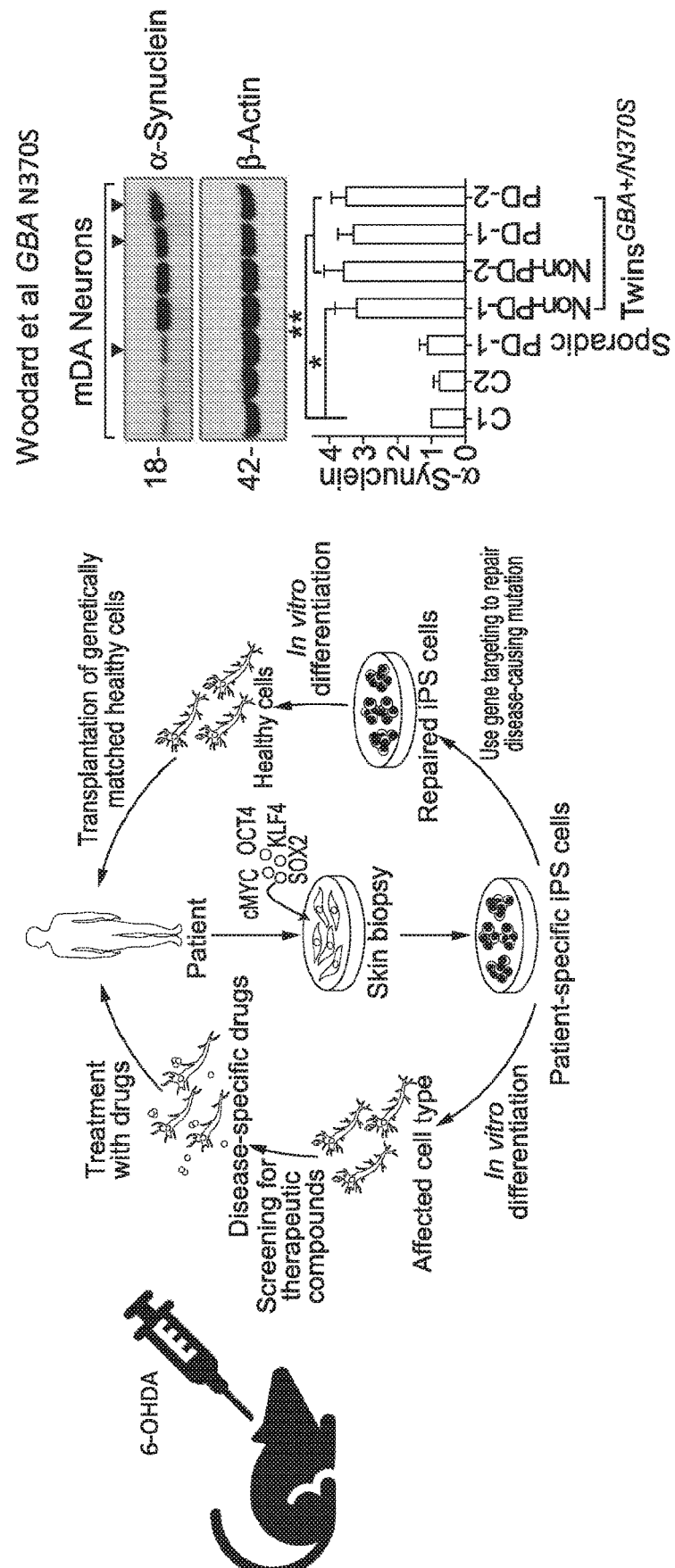
FIG. 8: Models of Parkinson's disease animal models fail to recapitulate classical parkinsonian phenotypes. Leading models include A53T, SNCA triplication, and LRRK2 G2019S. iPSC models capture patient specific genetics.
Figure 9:
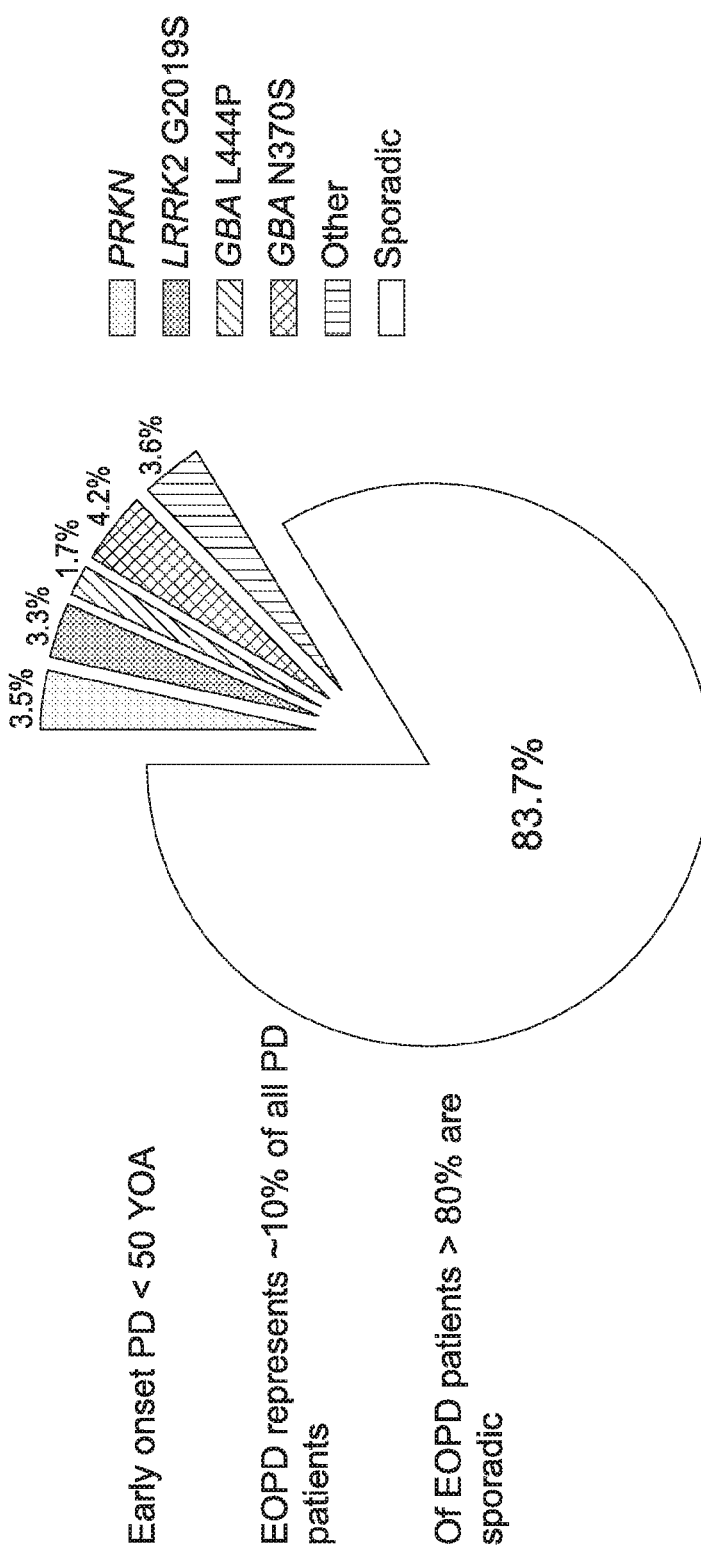
FIG. 9: Early onset PD distribution.
Figure 11:
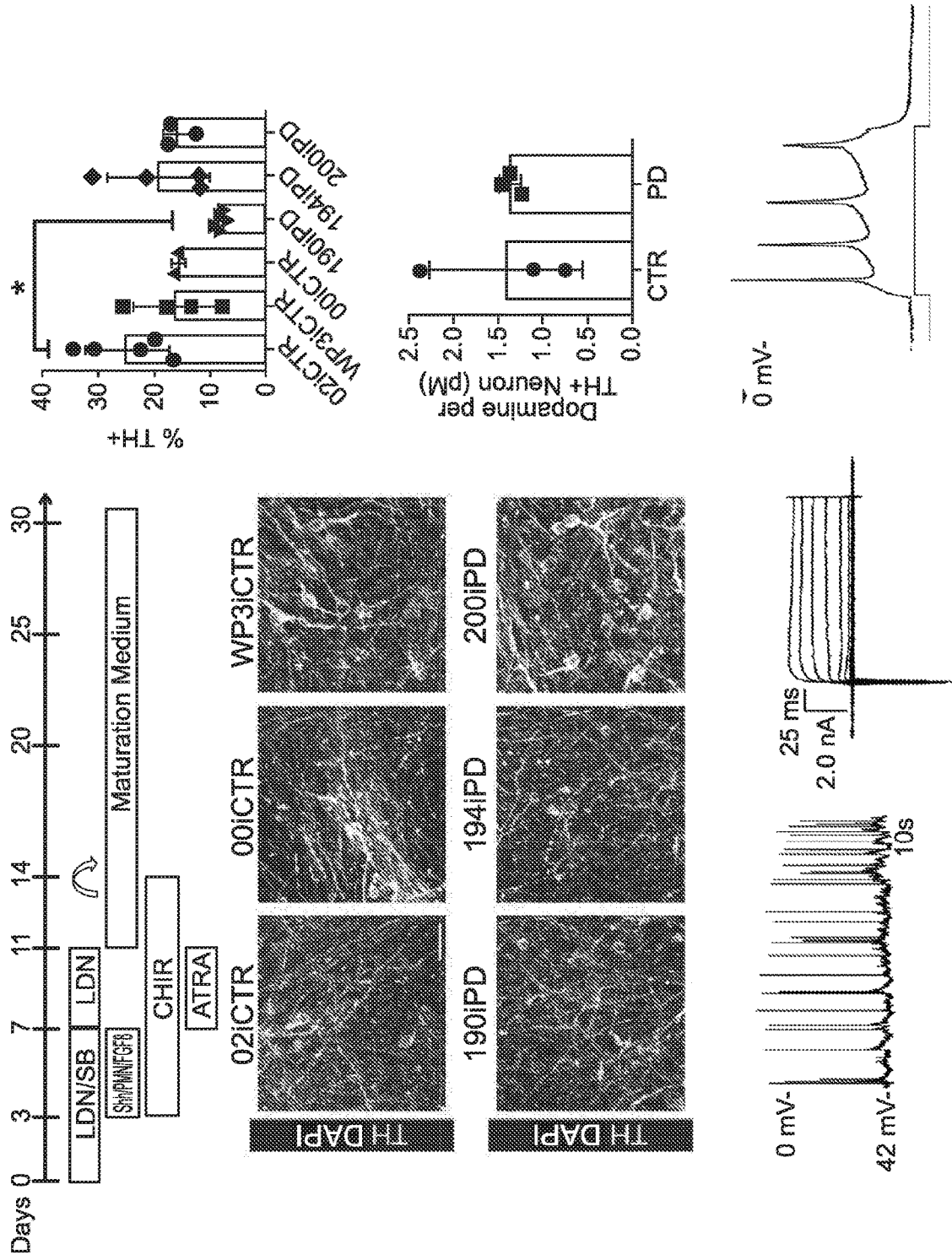
FIG. 11: Differentiation to mDA neural cultures. D30 midbrain dopaminergic neuron (mDA) cultures include ~20% TH+ cells, produce dopamine, exhibit spontaneous activity in K and Na channels, fire trains of APs on current injection.
Figure 12:
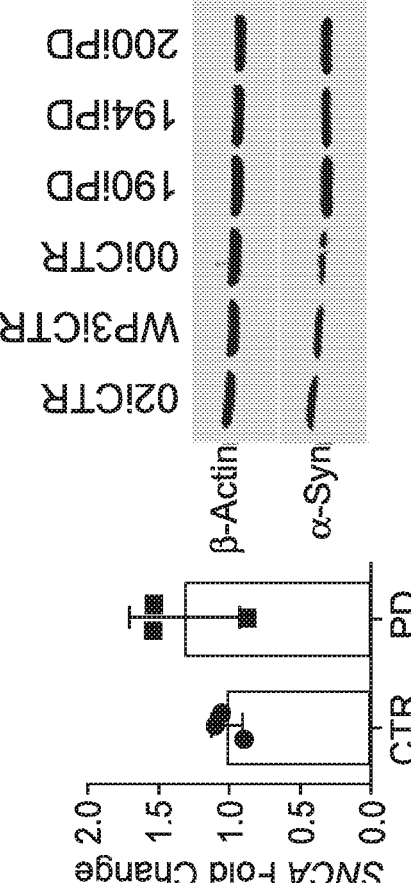
FIG. 12: α-synuclein accumulation in EOSPD mDA cultures. Increased α-synuclein levels in EOSPD mDA cultures by western blot and ELISA.
Figure 13:
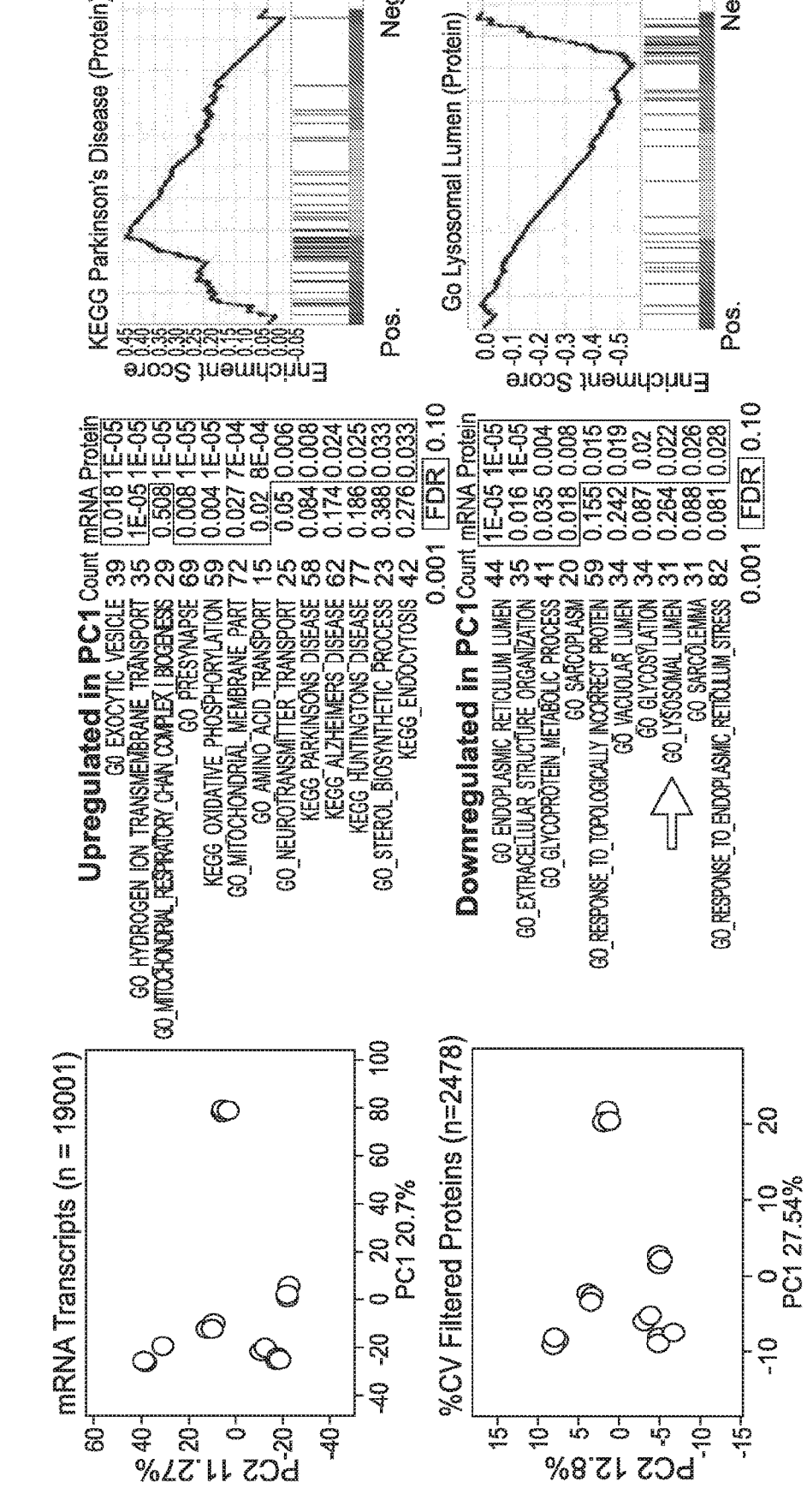
FIG. 13: Paired OMICS analysis of EOSPD mDA cultures. SWATH proteomic analysis paired with RNA-Seq transcriptomics.
Figure 14:
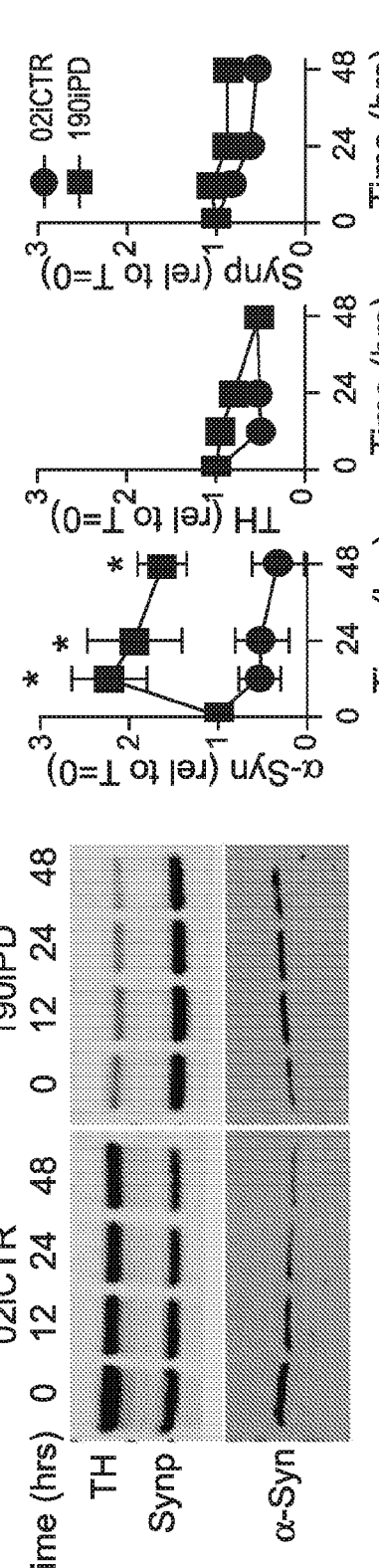
FIG. 14: α-synuclein degradation is impaired in EOSPD mDA cultures. α-synuclein (α-syn), tyrosine hydroxylase (TH), and synaptophysin (Synp) protein levels assayed over 48 hrs of cycloheximide treatment.
Figure 17:
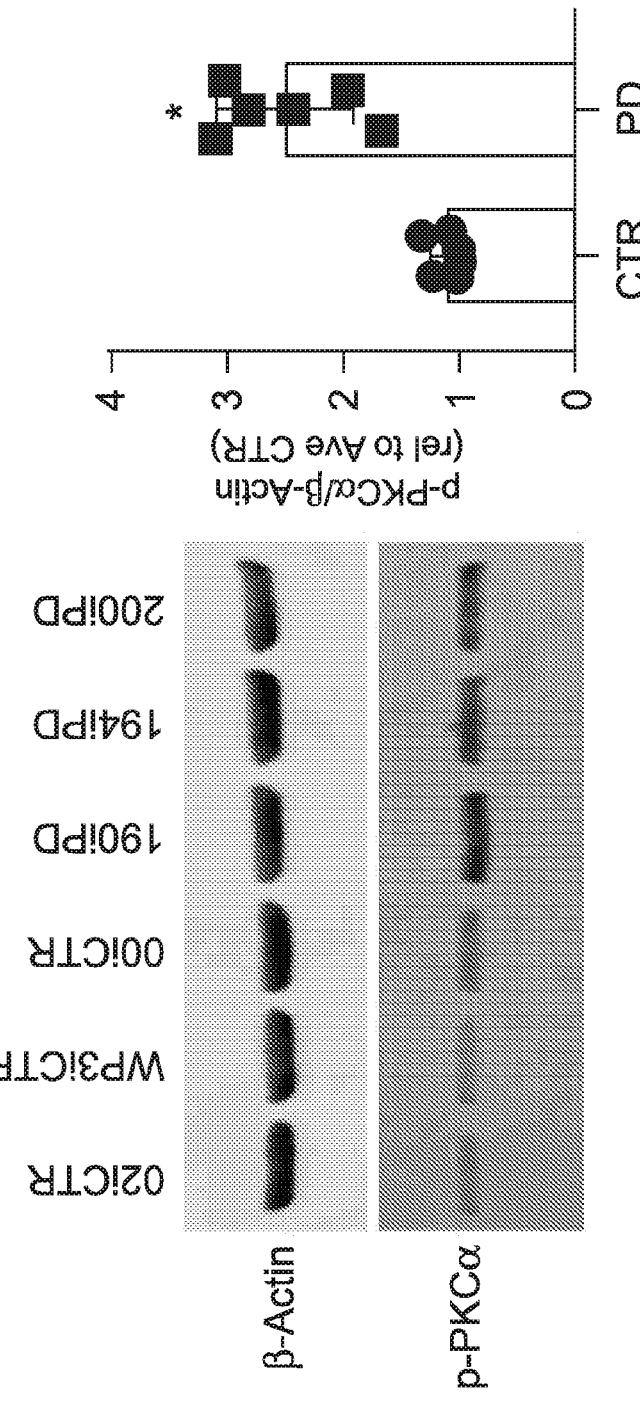
FIG. 17: p-PKCa is elevated in EOSPD mDA cultures. PKCa phospho Thr-638 controls the rate of agonist induced dephosphorylation and inactivation of the protein. Increased activity is associated with other neurodegenerative diseases (Alzheimer's).
Figure 18:
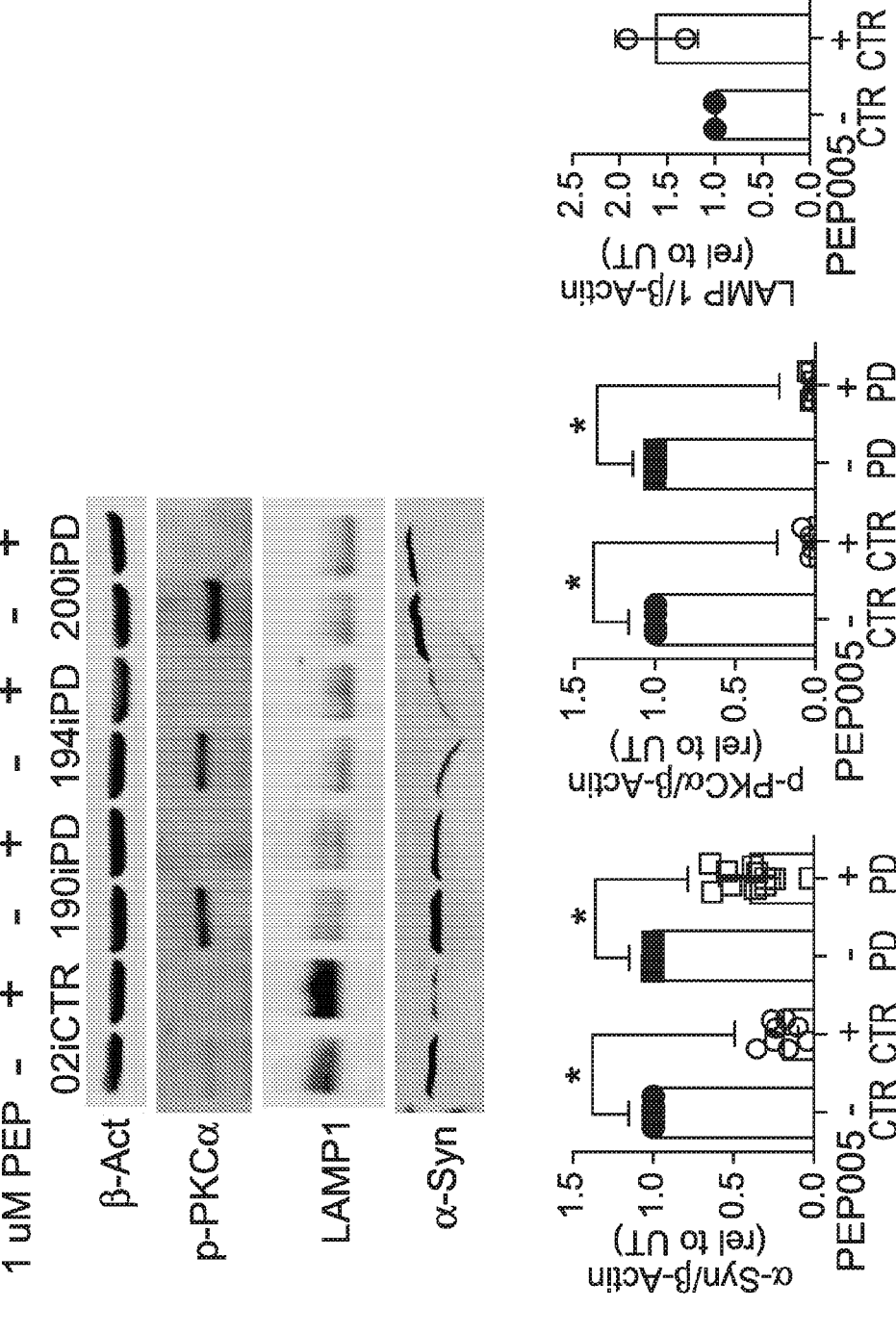
FIG. 18: PEP005 modulates EOSPD phenotypes.
Figure 19:
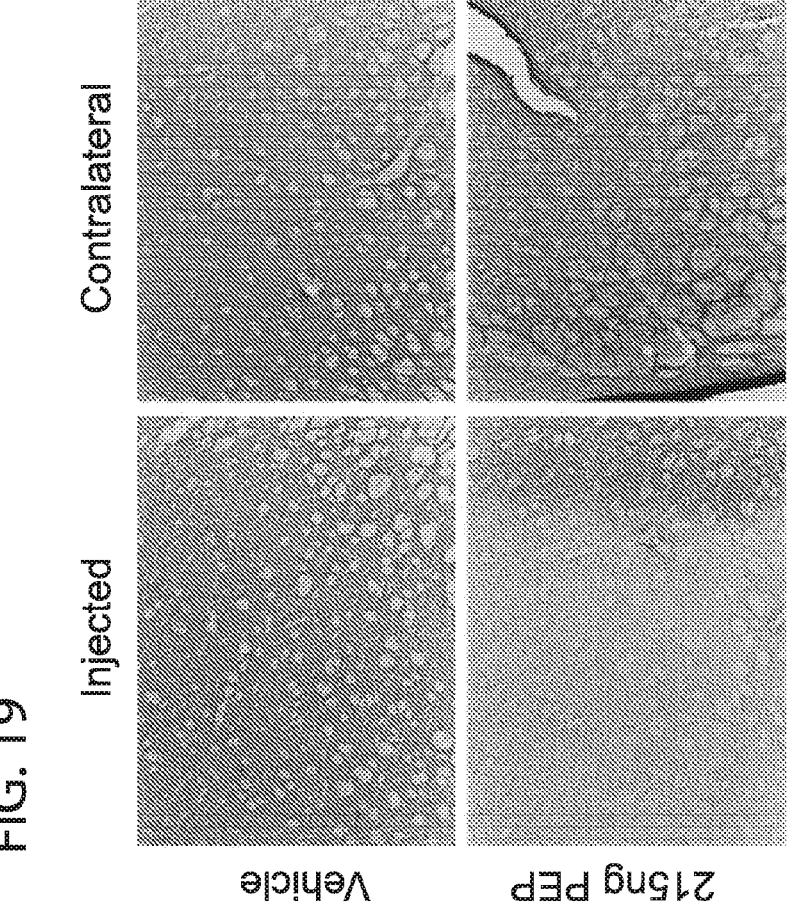
FIG. 19: PEP005 reduces α-synuclein levels in vivo. Wild-type C57/BL6 mice purchased from Jackson Labs. Unilateral striatal injections (L). α-synuclein levels assayed 3 days post-treatment.
Figure 20:
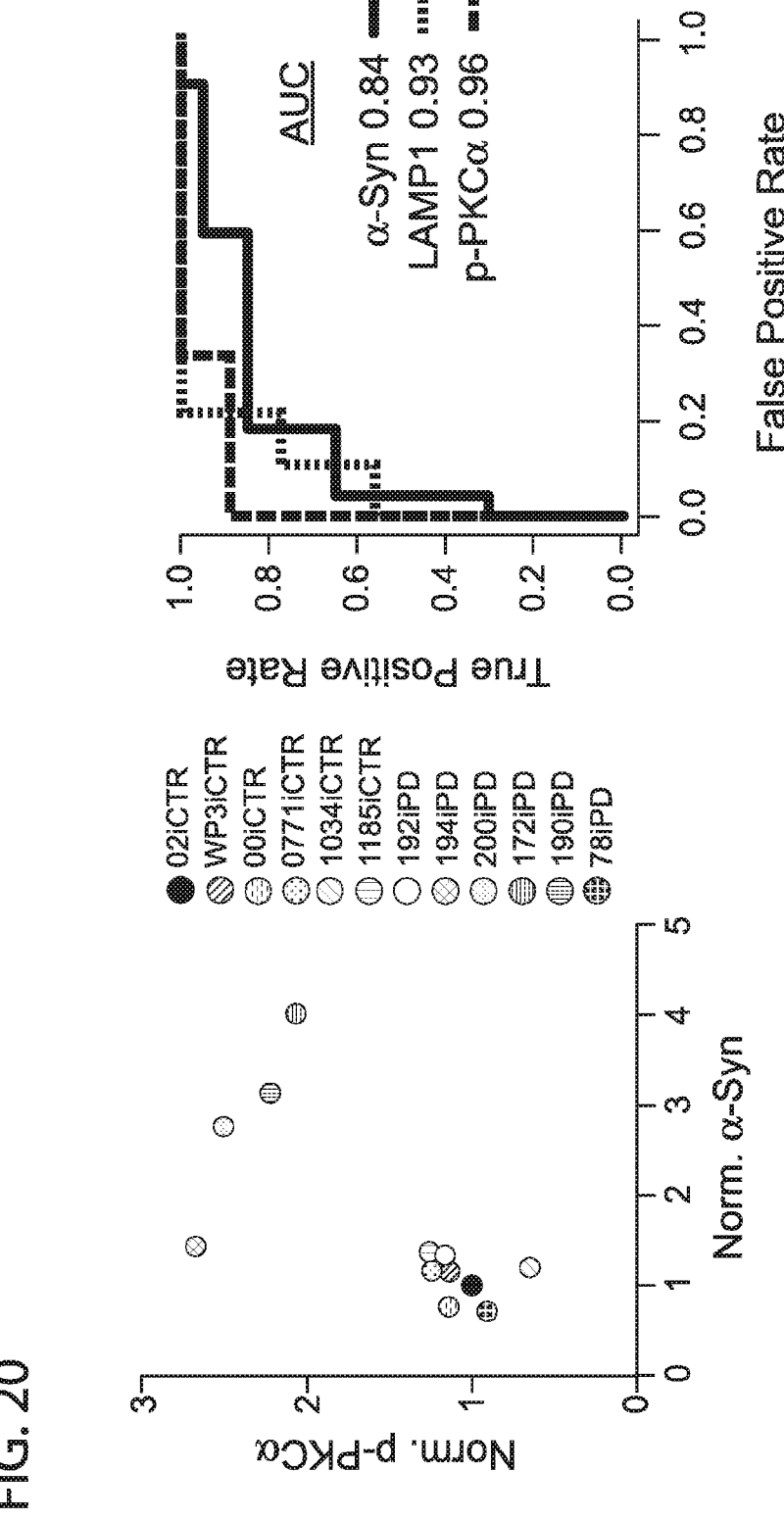
FIG. 20: EOSPD biomarkers correctly identify multiple iPSC lines. 10 of 11 iPSC lines screened in this system are correctly identified 4 of 5 EOSPD. Adult onset PD line does not display EOSPD phenotypes.
Figure 21:
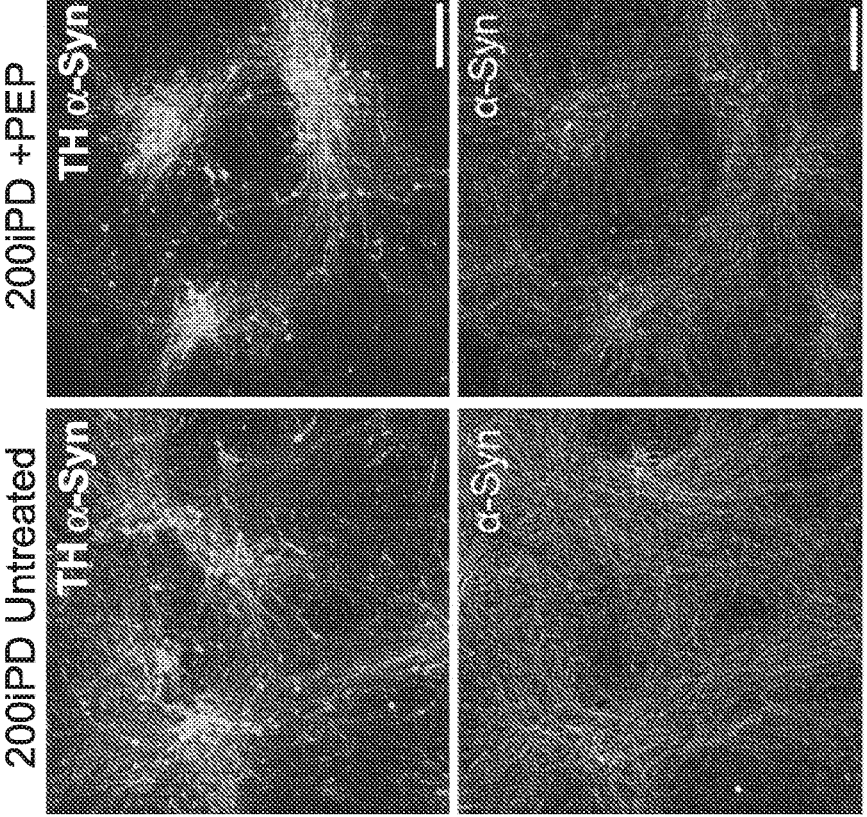
FIG. 21: PEP005 increases TH expression
Figure 22:
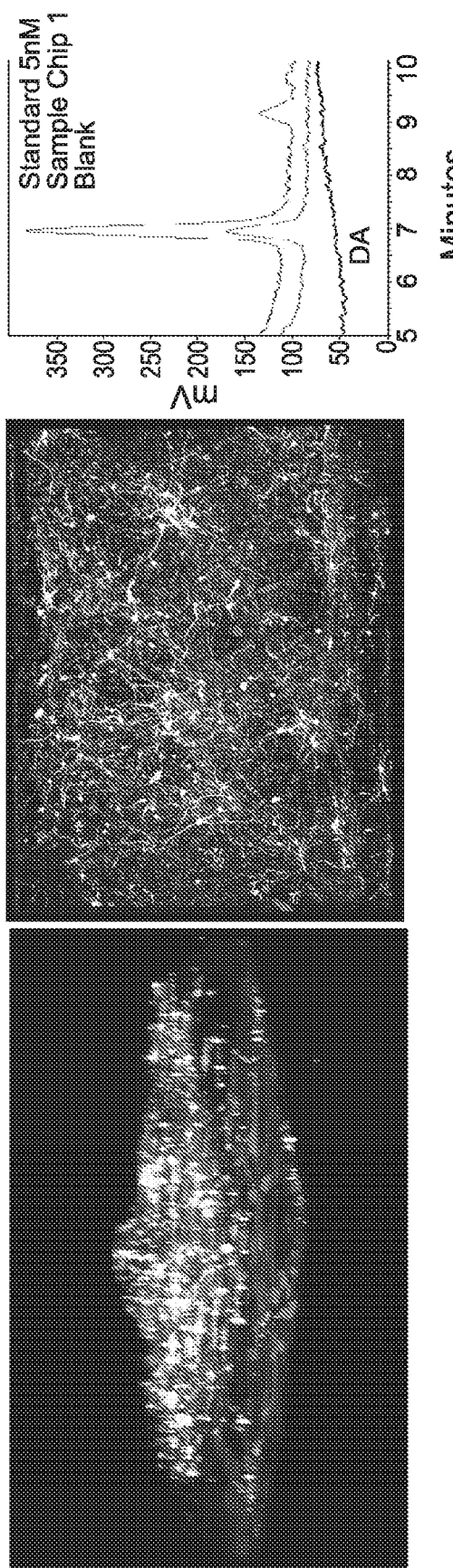
FIG. 22: DA-Chip: dopaminergic neuron endothelial cell co-cultures. Chip system adapted to include midbrain DA neurons for Parkinson's Disease Modeling Reproducible TH expression. Blood Brain Barrier component for drug testing.
Figure 24:
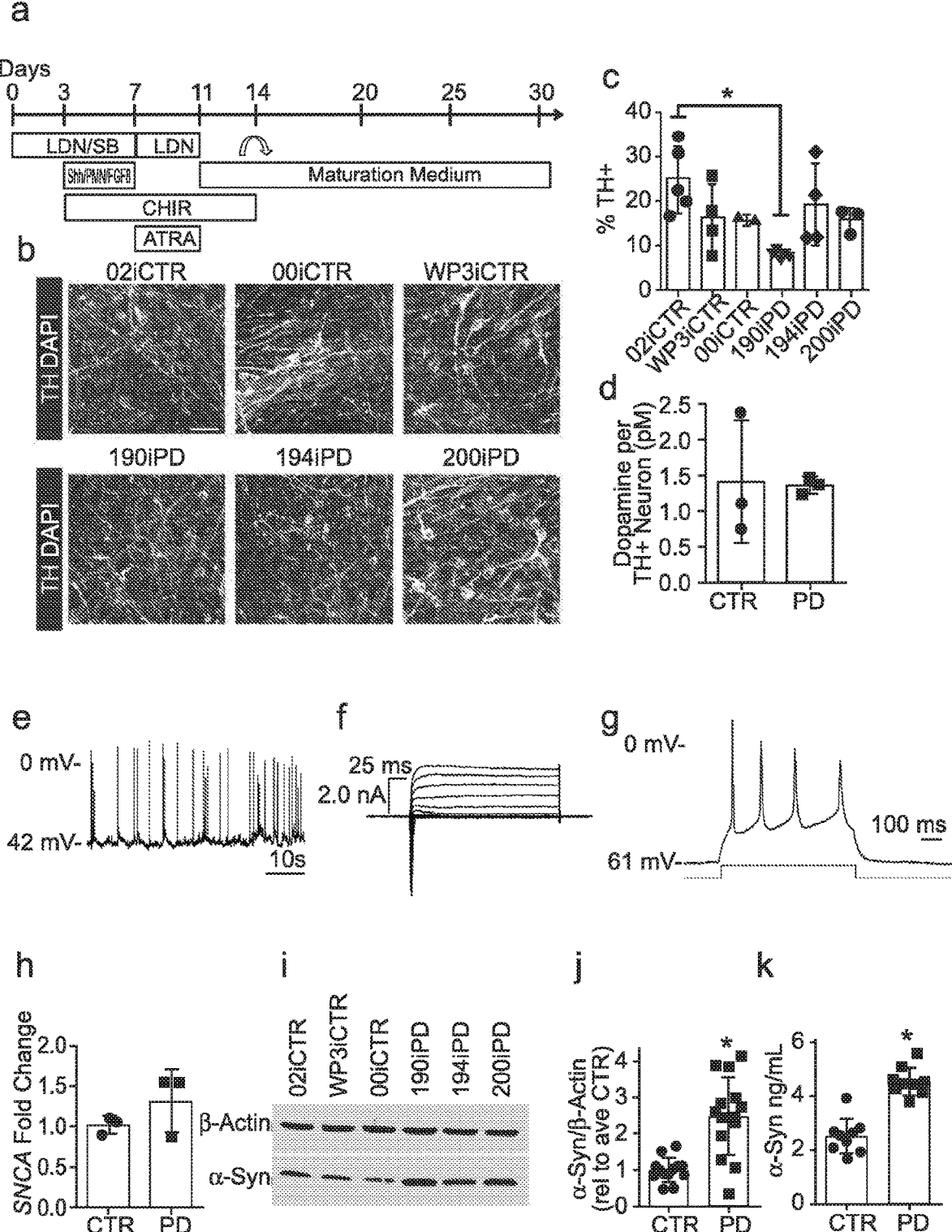
FIG. 24: EOSPD-derived iPSCs can be differentiated into midbrain dopaminergic (mDA) neural cultures that accumulate α-synuclein. (a) Differentiation schematic for mDA cultures. (b) Representative images of mDA cultures show TH expression and morphology. (c) Flow cytometry quantifies differentiation efficiency, with each point representing an average of 3 separate wells of an independent differentiation, repeated at least 3 times per line. * indicates significance (p<0.05) via one-way ANOVA (F 4.07, DF 23) with Tukey multiple comparisons test. (d) HLPC detection of total dopamine content normalized to differentiation efficiency by line. (e) Gap free recording of spontaneous activity in day 30 (d30) mDA neurons. (f) Voltage clamp recording of d30 mDA neurons. (g) Injected current recording of d30 mDA neurons. (h) SNCA expression by qPCR in d30 mDA cultures. (i) Western blot of d30 mDA cultures for α-synuclein production and β-actin as a housekeeping control. (j) Relative intensities from multiple western blots, with each point representing a band intensity from a separate differentiation, intensities are relative to average of control lines. (k) α-synuclein ELISA, each point represents an average of 3 wells from a separate differentiation, 3 independent differentiations are represented. Colors on graphs indicate different iPSC lines. *denotes significance from control p<0.0001 via t-test with Welch's correction (j,k). Error bars represent standard deviation (SD)
Figure 25:
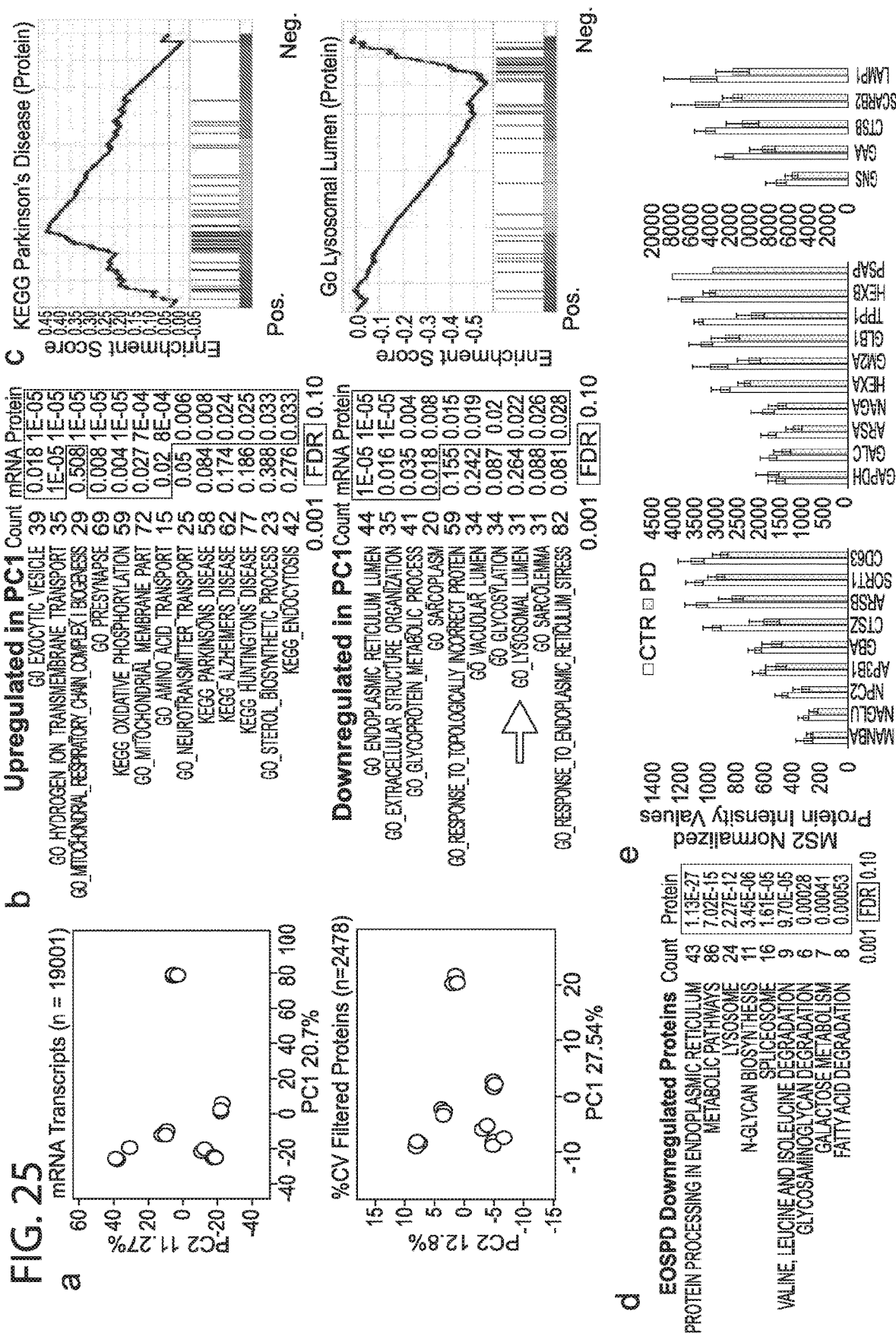
FIG. 25: Paired RNA-sequencing and proteomic analyses from mDA cultures. (a) PCA plots of whole transcriptomic and CV filtered proteomic data sets from matching mDA cultures at 30 days. Colors indicate cell lines. Light blue=02iCTR, dark blue=WP3iCTR, purple=00iCTR, Orange=194iPD, pink=200iPD, and red=190iPD. Replicate colors indicate biological replicates from different culture wells. (b) GSEA analyses of matching gene set components upregulated and downregulated along PC1 from both mRNA-Seq data and proteomic data. Pathways ranked by significance calculated by false discovery rate (FDR). GSEA zero values set to 1E-5. (c) Enrichment plots from proteomic analysis of GSEA terms significantly upregulated and downregulated in PC1. Red color indicates positive weighting score, blue indicates negative weighting score. PC1 genes are ordered by gene weighting along x-axis and black lines indicate genes contained in GSEA term. (d) String analysis of differentially downregulated protein KEGG pathways. (e) Average detected protein intensity values per significantly downregulated gene contained in KEGG Lysosome pathway. Error bars represent standard error of the mean (SEM).
Figure 27:
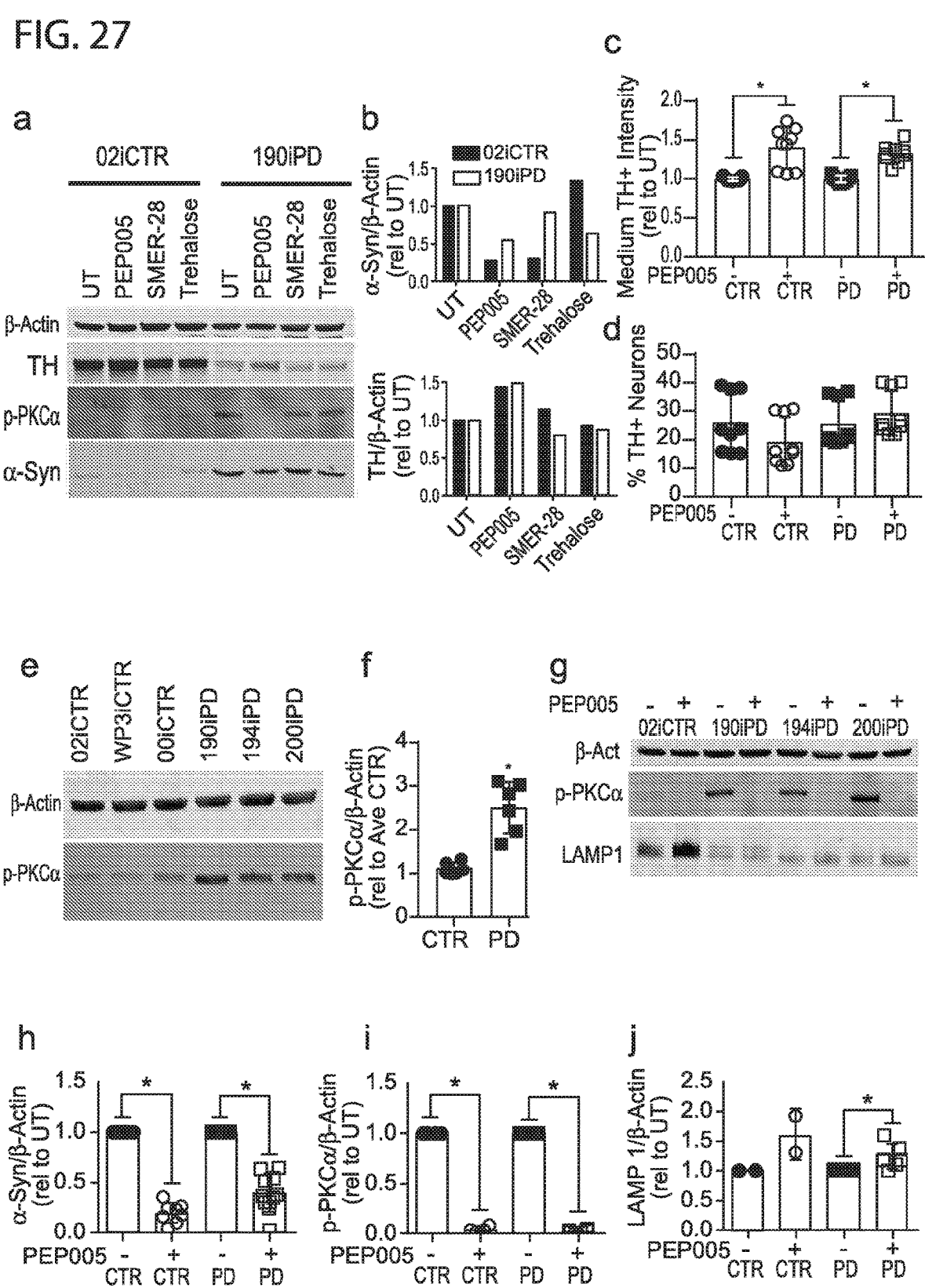
FIG. 27: Treatment of EOSPD mDA cultures with a PKC agonist reduces intracellular α-synuclein. (a) Western blot of day 30 (d30) mDA cultures untreated (UT) or treated with indicated compounds for 72 hours and (b) relative band quantifications. Flow cytometry analysis of d30 mDA cultures treated with PEP005 for 72 hrs (c) median TH intensity of positive cells relative to untreated mDA cultures of the same line, * indicates significance from untreated (p<0.05) via t-test with Welch's correction and (d) differentiation efficiency to TH+ neurons. (e) Baseline levels of p-PKCa in d30 mDA cultures. (f) Quantification of p-PKCa band intensities relative to control cells. Each point represents a separate differentiation and western blot, * indicates significance relative to control cells p<0.005 t-test with Welch's correction. (g) Western blot of d30 mDA cultures treated with PEP005 from multiple EOSPD and control lines. (h) Quantification of α-synuclein band intensities with and without PEP005 relative to untreated cells of the same line. (i) p-PKCa and (j) LAMP1 band intensities with and without PEP005 relative to untreated cells of the same line. * indicates significance relative to untreated cells p<0.005 paired t-test (h,i,j). Error bars represent standard deviation (SD).
Figure 28:
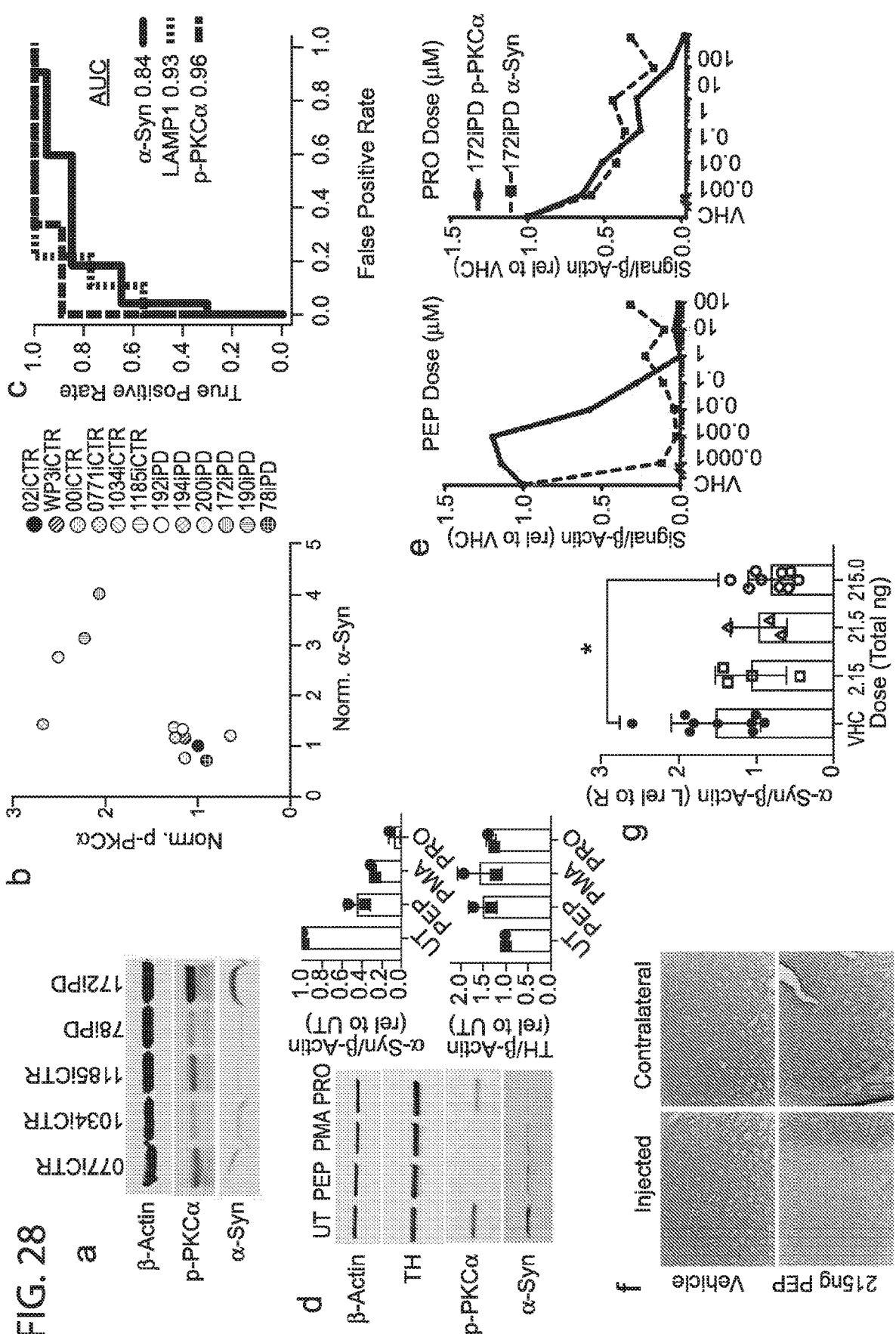
FIG. 28: Confirmation of PKC pathway effects. (a) Western blot and quantification of additional control and EOSPD mDA cultures at day 30. (b) Average α-synuclein and p-PKCa expression from all mDA cultures normalized to 02iCTR. (c) ROC curve plot of normalized α-synuclein (red), LAMP1 (blue), p-PKCa (orange). (d) Treatment of mDA cultures with additional PKC agonists and quantification of band intensities. (e) PEP005 and Prostratin dose-response curve in 172iPD mDA culture. (e) Immunohistochemical staining of α-synuclein in mouse striatum treated with 215 ng of PEP005 for 3 days. (f) Western blot quantification of α-synuclein in mouse striatum presented as injected (L)/contralateral (R) in response to PEP005 dose. n=9 VHC, 4 2.15 ng, 3 21.5 ng, and 9 215 ng animals. * indicates significance (p<0.05) via one-way ANOVA (F 3.96, DF 24) with Tukey multiple comparisons test. Error bars represent standard deviation (SD).
Figure 29:
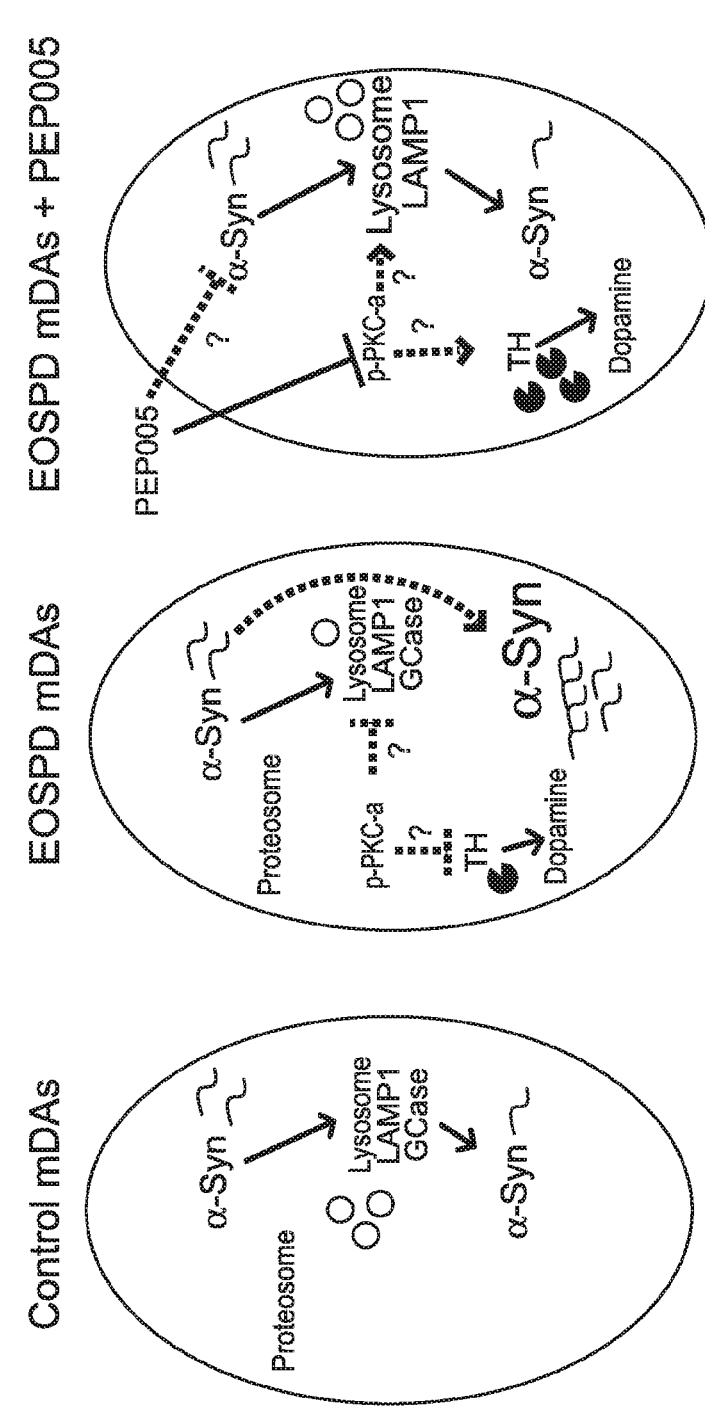
FIG. 29: Schematic representation of EOSPD biomarkers and suspected activity of phorbol ester compounds.
Figure 32:
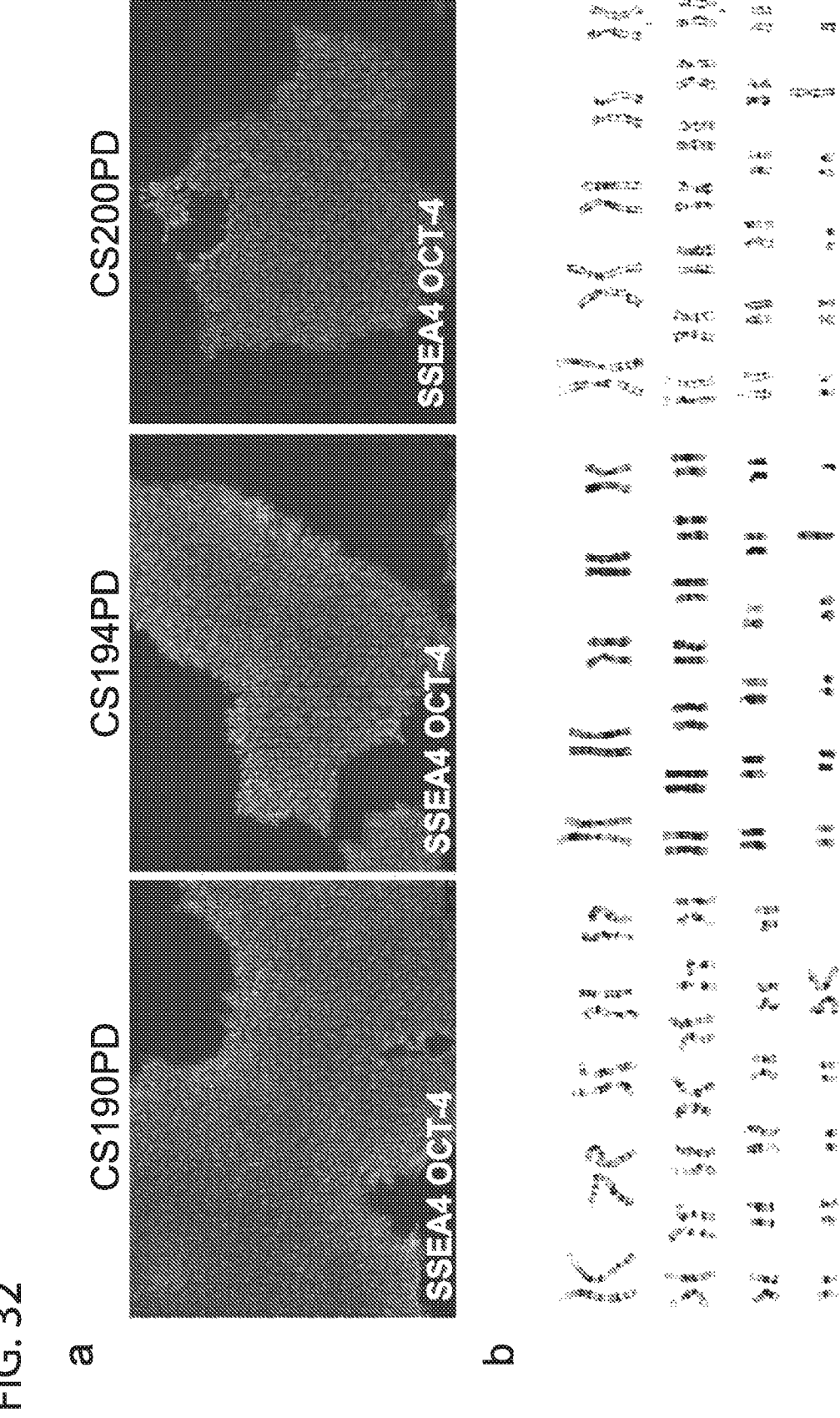
FIG. 32: Generation of EOSPD iPSCs. (a) SSEA4 (green) and OCT-4 immunostaining in undifferentiated iPSCs from EOSPD patients. (b) Normal karyotypes from EOSPD patient iPSCs.
Figure 33:
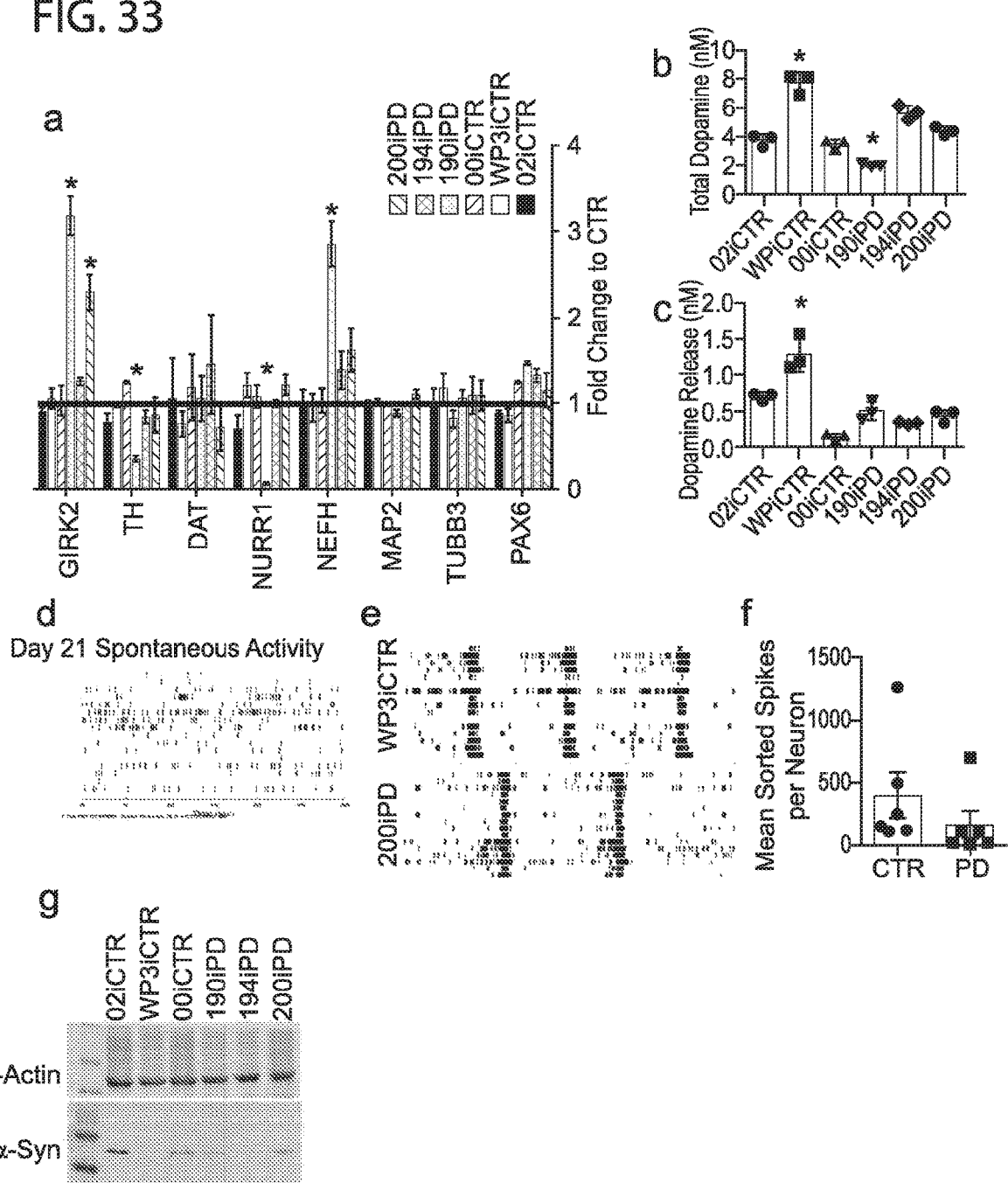
FIG. 33: Additional characterization of mDA cultures. (a) Expression of dopaminergic neuron genes in day 30 (d30) mDA cultures from 6 iPSC lines. Data are relative to average expression in control lines. (b) HPLC detection of total dopamine in d30 mDA culture lysates. * indicates significance from all other lines (p<0.05) via one-way ANOVA (F 67.7, DF 17) with Tukey multiple comparisons test. (c) HPLC detection of released dopamine in aCSF following a 15 min incubation at 37° C. * indicates significance from all other lines (p<0.05) via one-way ANOVA (F 31.6, DF 17) with Tukey multiple comparisons test. ((d) MEA recording of spontaneous activity from 02iCTR mDA neurons at day 21 of differentiation. (e) MEA recordings of control and EOSPD mDA neurons at d30 of differentiation. (f) Average sorted spikes per neuron at d30. Points represent an average of 4 wells, colors indicate iPSC lines. (g) Western blot of α-synuclein in control and EOSPD iPSCs. Error bars represent standard deviation (SD).
Figure 34:
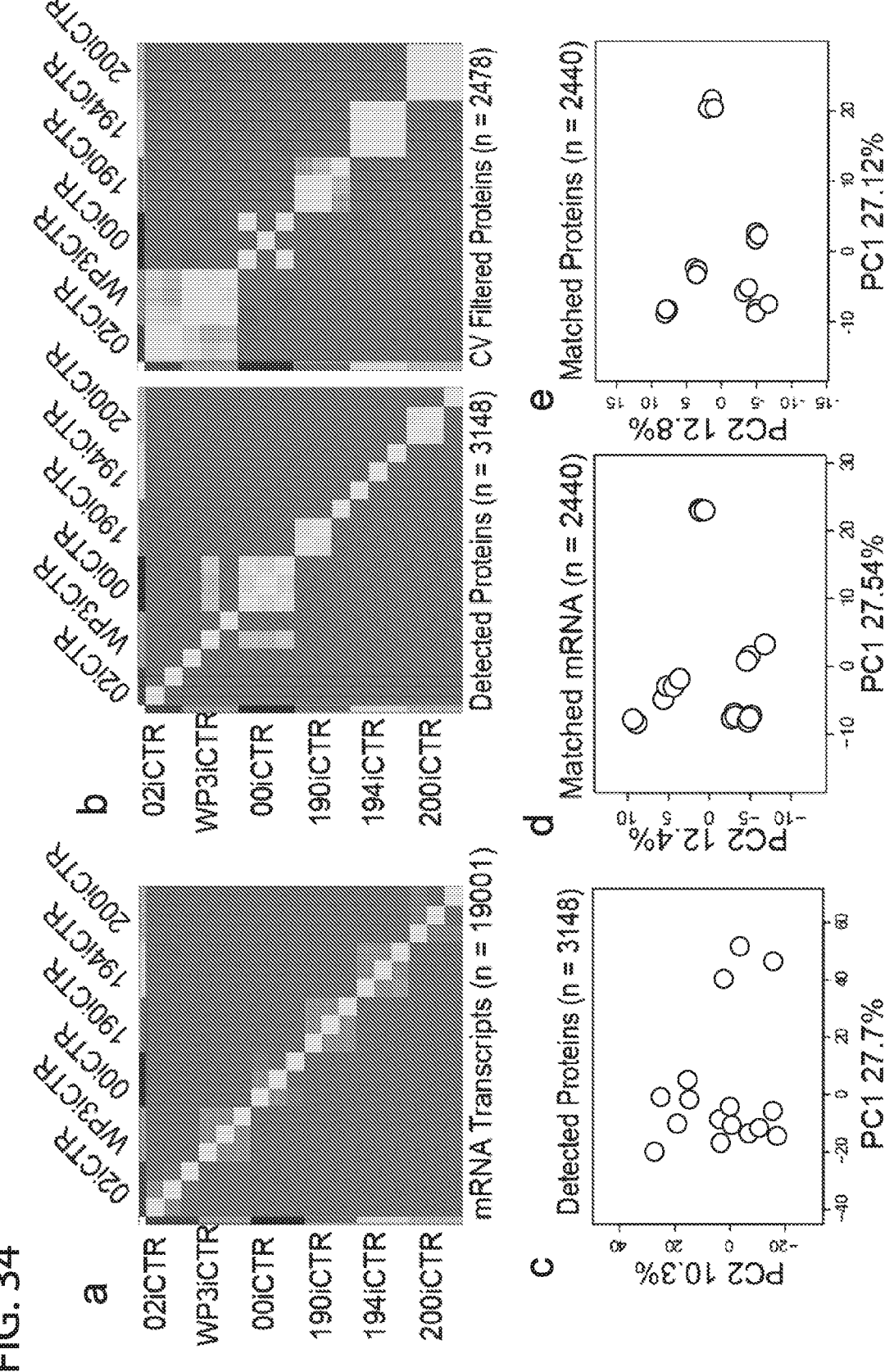
FIG. 34: Paired transcriptomic and proteomic analysis. Pearson correlation plots of (a) transcriptomic and (b) proteomic data. (c) PCA plot of all detected proteins. (d) PCA plot of matching RNA-Seq transcripts. (e) PCA plot of matching proteins.
Figure 35:
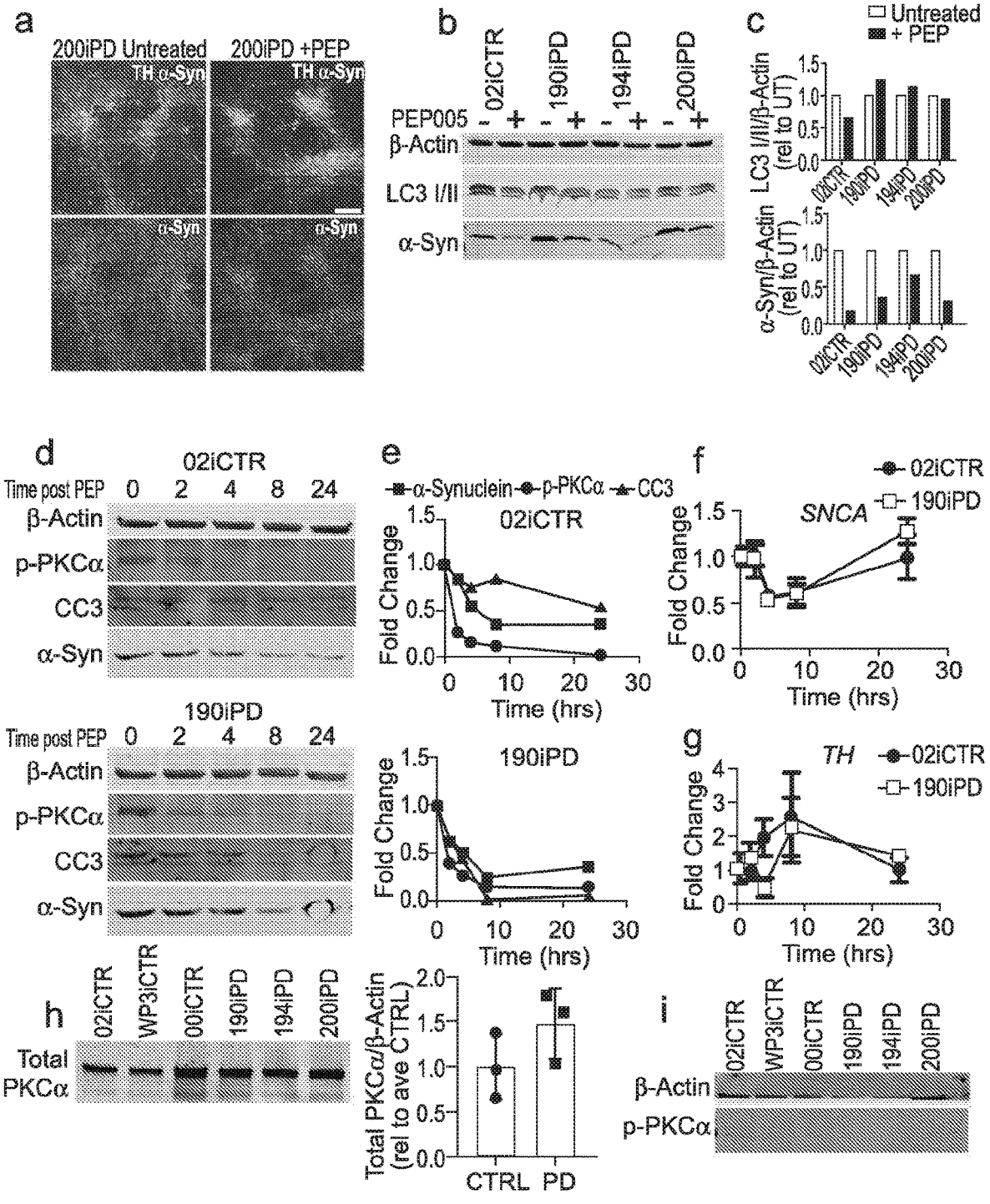
FIG. 35: Additional characterization of PEP005 treatment. (a) Immunocytochemistry showing TH and α-synuclein in 200iPD d30 mDA cultures with and without PEP005 treatment. (b) Day 30 mDA neurons treated with PEP005 from multiple EOSPD and control lines. (c) Quantification of LC3I/II and α-synuclein band intensities relative to untreated cells from the same line. (d) Time-course of PEP005 treatment in EOSPD and control mDA neurons. (e) Quantification of α-synuclein, p-PKCα and CC3 band intensities in EOSPD and control mDA neurons. qPCR from paired samples over PEP005 time-course showing (f) SNCA and (g) TH expression. (h) Western blot of total PKCa in d30 mDA neural cultures and quantification. Not significant (p>0.05) via t-test with Welch's correction. (i) Western blot of undifferentiated iPSCs showing p-PKCa. Error bars represent standard deviation (SD).
Figure 38:
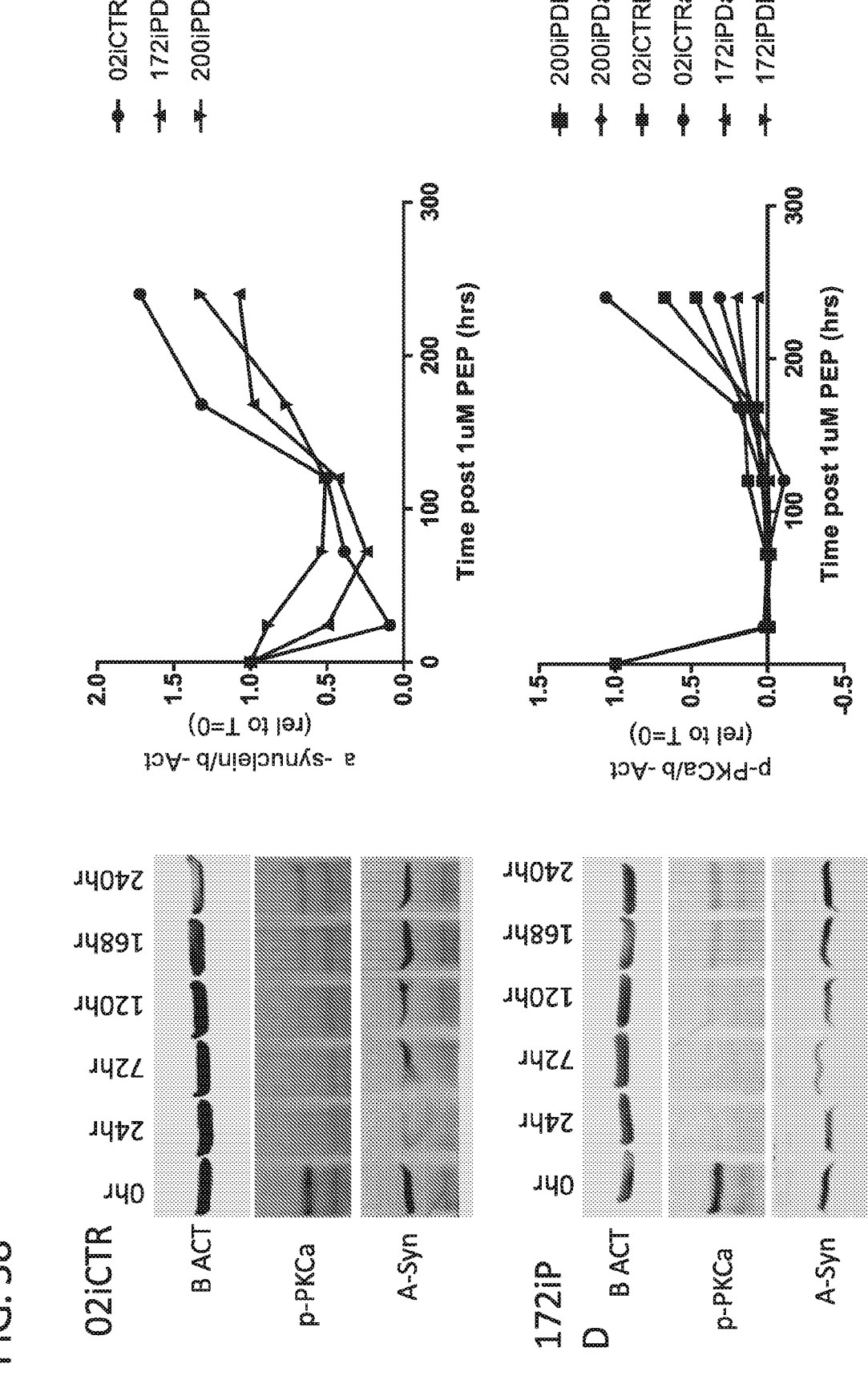
FIG. 38: Duration of PEP005 effects in vitro.

A defining hallmark of PD is the specific loss of dopaminergic neurons in the substantia nigra and it is therefore of interest to differentiate iPSC along this lineage. iPSC lines from both PD and control patients were differentiated to dopaminergic neurons using the protocol described in Table 1, FIG. 2A and FIG. 6.

Briefly, iPSC lines were subjected to a modified dual SMAD-inhibition based floor plate induction protocol. Exposure to LDN/SB, followed by SHH/Purmorphamine/FGF8 and CHIR99021, thereafter including SB withdrawal and retinoic acid addition, support midbrain FP and DA neuron yield (see FIG. 1d). Further maturation was carried out in Neurobasal/B27 medium supplemented with AA, BDNF, GDNF, TGFβ3 and dbcAMP.

TABLE 1

| Differentiation Protocol - Media | | | | | | |
|---|---|---|---|---|---|---|
| Stage 1 Media: | | | | | | for x volume |
| | Working Dilution | | | | x= | 140 mL |
| DMEM/F12 | 50% | | | | DMEM/F12 | 70 mL |
| Neurobasal | 50% | | | | Neurobasal | 70 mL |
| N2 | 1:100 | | | | N2 | 1.4 mL |
| B27 - Vitamin A | 1:50 | Stock: | Working: | | B27 - Vitamin A | 2.8 mL |
| LDN | 1:10000 | 10 mM | 1 uM | | LDN | 14 uL |
| SB | 1:5000 | 10 mM | 2 uM | | SB | 28 uL |
| Stage 2 Media: | | | | | | for x volume |
| | Working Dilution | | | | x= | 220 mL |
| DMEM/F12 | 50% | | | | DMEM/F12 | 110 mL |
| Neurobasal | 50% | | | | Neurobasal | 110 mL |
| N2 | 1:100 | | | | N2 | 2.2 mL |
| B27 - Vitamin A | 1:50 | | | | B27 - Vitamin A | 4.4 mL |
| LDN | 1:10000 | | | | LDN | 22 uL |
| SB | 1:5000 | Stock: | Working: | | SB | 44 uL |
| PMN | 1:5000 | 10 mM | 2 uM | | PMN | 44 uL |
| Shh | 1:1000 | 100 ug/mL | Shh | | Shh | 220 uL |
| CHIR | 1:6670 | 15 mM | 2.25 uM | | CHIR | 33.00 uL |
| FGF8 | 1:5000 | 50 ug/mL | FGF8 | | FGF8 | 44 uL |
| Stage 3 Media: | | | | | | for x volume |
| | | | | | x= | 50 mL |
| DMEM/F12 | 50% | | | | DMEM/F12 | 25 mL |
| Neurobasal | 50% | | | | Neurobasal | 25 mL |
| N2 | 1:100 | | | | N2 | 0.5 mL |
| B27 - Vitamin A | 1:50 | | | | B27 - Vitamin A | 1 mL |
| LDN | 1:10000 | | | | LDN | 5 uL |
| CHIR | 1:6670 | Stock: | Working: | | CHIR | 7.50 uL |
| ATRA | 1:2000 | 10 mM | 5 uM | | ATRA | 25 uL |
| Stage 4 Media: | | | | | | for x volume |
| | | | | | x= | 60 mL |
| DMEM/F12 | 50% | | | | DMEM/F12 | 30 mL |
| Neurobasal | 50% | | | | Neurobasal | 30 mL |
| N2 | 1:100 | | | | N2 | 0.6 mL |
| B27 | 1:50 | Stock: | Working: | | B27 | 1.2 mL |
| AA | 1:1000 | 500 ug/mL | AA | | AA | 60.00 uL |
| BDNF | 1:500 | 10 ug/mL | 20 ng/mL | | BDNF | 120.00 uL |
| GDNF | 1:500 | 10 ug/mL | 20 ng/mL | | GDNF | 120.00 uL |
| dbCAMP | 1:500 | 102 mM | .2 mM | | dbCAMP | 120.00 uL |
| TGF-B3 | 1:10000 | 10 ug/mL | 1 ng/mL | | TGF-B3 | 6.00 uL |
| DAPT | 1:4000 | 10 mM | 2.5 uM | | DAPT | 15.00 uL |
| CHIR | 1:6670 | | | | CHIR | 9.00 uL |
| Maturation Media: | | | | | | for x volume |
| | | | | | x= | 100 mL |
| DMEM/F12 | 50% | | | | DMEM/F12 | 50 mL |
| Neurobasal | 50% | | | | Neurobasal | 50 mL |

TABLE 1-continued

| Differentiation Protocol - Media | | | |
|---|---|---|---|
| N2 | 1:200 | N2 | 0.5 mL |
| B27 | 1:100 | B27 | 1 mL |
| AA | 1:1000 | AA | 100.00 uL |
| BDNF | 1:500 | BDNF | 200.00 uL |
| GDNF | 1:500 | GDNF | 200.00 uL |
| dbCAMP | 1:500 | dbCAMP | 200.00 uL |
| TGF-B3 | 1:10000 | TGF-B3 | 10.00 uL |
| DAPT | 1:4000 | DAPT | 25.00 uL |

At day 30, differentiated cells expressed markers of dopamine neurons including TH, Nurr1, and GRIK2 with roughly 15% of the cells expressing TH (FIG. 2A) (FIG. 2B, FIG. 2C). Overall differentiation efficiency was compared across all 6 lines by counting the number of TH expressing cells using flow cytometry (FIG. 2C). Two of the PD lines showed similar numbers of DA neurons to those found in controls. However, differentiation of the 190iPD line yielded fewer TH positive neurons and these cells expressed less of the floorplate progenitor markers FOXA2 and LMX1A but more of the mature neural markers GRIK2 and NEFH.

Figures 2D, 2E, 2F, 2G, 2H:
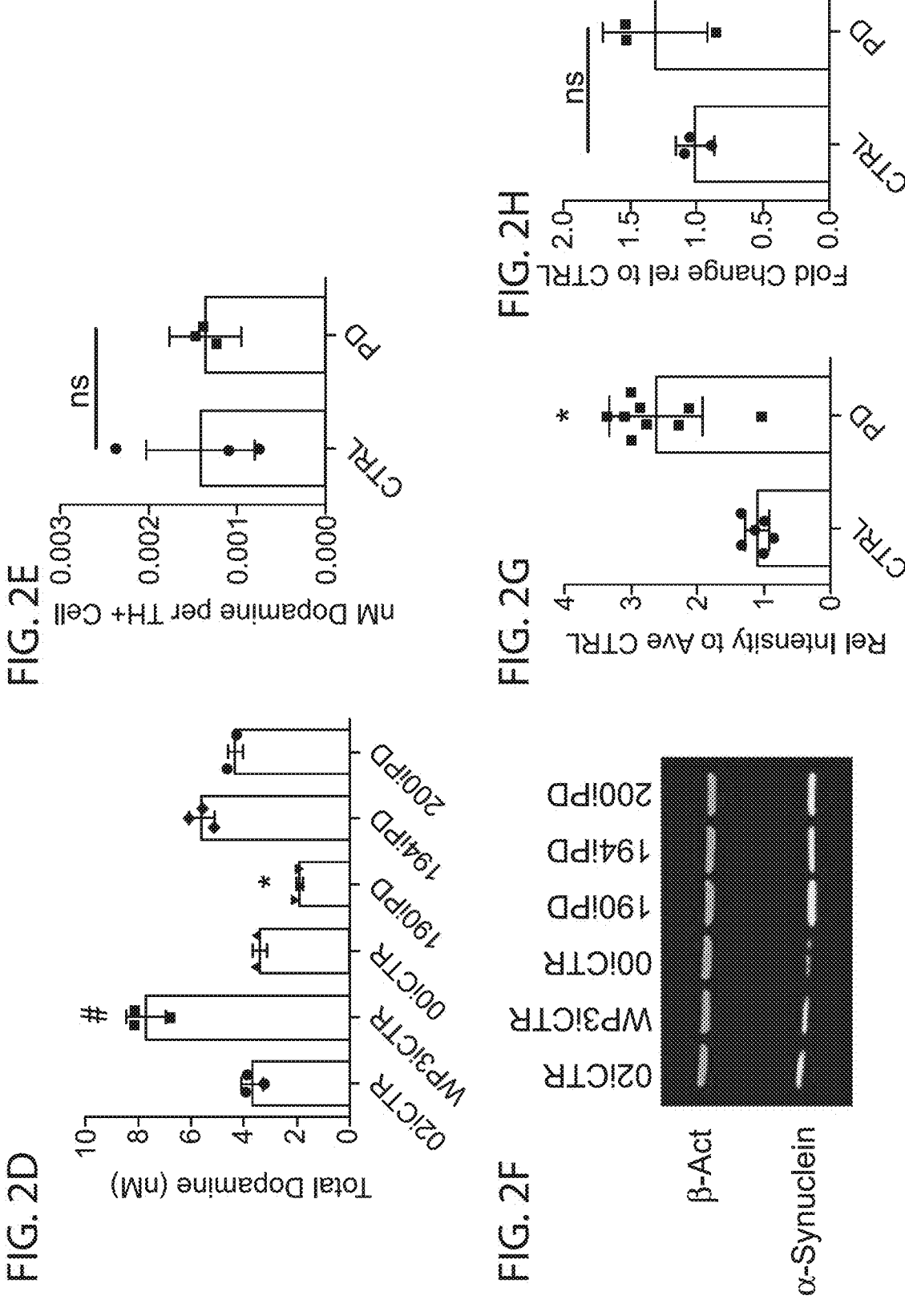

To determine whether TH enzyme resulted in altered levels of dopamine in the developing neurons, 30 day old DANs were lysed and analyzed for dopamine production by HPLC. Differences in total dopamine were present by line with the 190iPD line again producing less dopamine and the WP3iCTR line producing more. However, when normalized to the number of TH expressing neurons, all lines produced dopamine at similar levels (FIG. 2D, FIG. 2E). To determine the electrophysiological function and potential disease signature of the developing neurons, multi-electrode array recordings were conducted over time in culture. Spontaneous activity was observed day 20 of differentiation and by day 30, both PD and control cells produce coordinated bursts of activity. When activity was quantified across all lines, similar levels of spontaneous spikes were observed between disease and control DaN cultures. Together, these data indicate that iPSCs derived from EOSPD patients differentiated efficiently into functional dopaminergic neurons that possessed similar neural activity to non-diseased patient lines.

Example 3

α-Synuclein Accumulates Specifically in EOSPD DANs

The protein α-Synuclein abnormally accumulates within Lewy bodies in all forms of Parkinson's disease, and accumulation through duplication or triplication of the SNCA gene is known to lead to PD. However, it's exact role in sporadic PD remains uncertain and previous studies have not shown consistent differences in adult onset sporadic PD. To determine if α-Synuclein protein accumulated the cultures of early onset sporadic PD origin, the 6 lines were differentiated for 30 days and probed for soluble α-Synuclein by western blot.

Strikingly, all 3 EOSPD DAN lysates exhibited increased levels of α-Synuclein protein when compared to controls (FIG. 2F, FIG. 2G). For verification of α-Synuclein accumulation, an ELISA was conducted on both media supernatant and cell lysates. The supernatant concentration of α-Synuclein was below detection limits, and cell lysates confirmed a significant increase in α-Synuclein protein in the diseased lines. Protein lysates from the lines at the iPSC stage did not exhibit increased α-Synuclein indicating accumulation was specific to the differentiated cultures.

To determine if the increased protein could be attributed to increased transcription of the SNCA gene, QPCR was conducted on DAN cultures at day 30 (FIG. 2H). These data indicate that two of the EOSPD lines, 190iPD and 200iPD, exhibit increased SNCA expression compared to the control lines but the third, 194iPD, does not suggesting that increased transcription alone was not the sole cause of α-Synuclein accumulation.

Example 4

Lysosomal Proteins are Dysregulated in EOSPD DANs

Since increased transcription of the SNCA gene could not fully explain EOSPD specific α-Synuclein protein accumulation, the Inventors next sought to determine other factors that may contribute to this effect through both RNA sequencing and proteomics on a paired sample set derived from the same culture wells. Whole transcriptomic RNA sequencing (RNA-Seq) detected 27384 unique transcripts while proteomic analysis yielded 2478 proteins that met reproducibility thresholds. Pearson correlation coefficients showed high consistency among sample replicates.

Figure 3D:
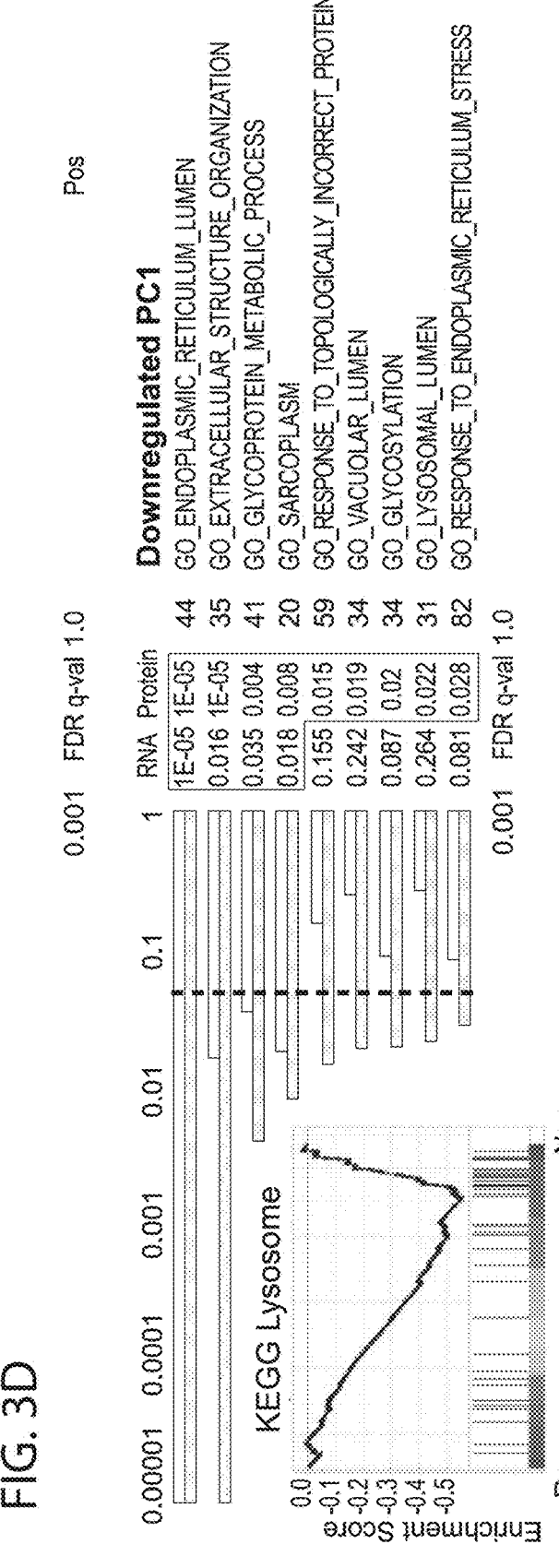

Combinatorial analysis of proteins and transcripts common to both proteomics and RNA-Seq datasets yielded 2437 matched genes between the two analysis modes (FIG. 3A). Unsupervised principal component analysis (PCA) of the matched gene set revealed a clear delineation between the PD cells and control along PC1 from both transcriptomic and proteomic data sets (FIG. 3B). Analysis of the entire RNA-Seq dataset yielded similar PCA. To determine significant pathways that contributed to this separation, all matching genes were ranked by PC1 gene weighting from both the mRNA or proteomic PCA analysis. Separate GSEA analyses of each ranked list were then merged to reveal common pathways significantly dysregulated between the PD and control cells (FIG. 3C). α-Synuclein and other synaptic vesicle genes related to dopamine release such as Synapsin (SYP), synaptic vesicle 2 A (SV2A), and SNAP25 were significantly enriched in the term as well as terms related to general synaptic machinery and function such as GO_EXOCYTIC_VESICLE (FIG. 3C). Metabolic genes contained in KEGG_OXIDATIVE_PHOSPHORYLATION were also significantly upregulated in ESOPD lines. In addition, terms related to neurodegenerative disease such as PD, Alzheimer's, and Huntington's disease were significantly upregulated in PD DANs suggesting that important aspects of neurodegeneration had been captured in the culture system (FIG. 3C). Significantly downregulated terms GO_LYSOSOMAL_LUMEN and GO_ENDOPLASMI- C_RETICULUM_LUMEN indicated deficiencies in proteogenesis and lysosomal protein degradation compared to non-diseased controls (FIG. 3D).

Example 5

Degradation of α-Synuclein is Impaired in PD DANs

Reduction in lysosomal proteins in EOSPD DANs led us to determine if accumulated α-Synuclein was the result of reduced degradation function. To test overall degradation rates, global transcriptional function was inhibited in DANs for 48 hours via cycloheximide treatment and α-Synuclein protein was quantified over time (FIG. 4A, FIG. 4B). In a control line, 02iCTR, α-Synuclein degraded over the course of the 48 hr treatment with an observed half-life of approximately 10 hours (FIG. 4B). However, in the most severe EOSPD line (190iPD) α-Synuclein instead accumulated over the duration of this treatment. This sharp dichotomy suggested fundamental deficiency in the specific degradation of α-Synuclein. This is supported by similar degradation profiles between control and PD cells of other proteins such as TH (FIG. 4A, FIG. 4C) and Synaptophysin (FIG. 4A, FIG. 4D).

Protein degradation can be largely divided into proteosomal and autophagy/lysosomal degradation pathways. To determine proteosomal degradation was responsible for α-Synuclein proteolysis, DaN cultures were treated with the proteasome inhibitor MG132 for 24 hrs which resulted in accumulation of P53, a protein canonically degraded via proteosomal means, but no substantial change in α-Synuclein levels (FIG. 4E). This result indicates proteasome degradation was not a significant contributor to α-Synuclein degradation in DAN cultures.

To determine lysosomal involvement in α-Synuclein degradation, the Inventors probed for glucocerebrosidase or GCase activity and total LAMP1 protein. The Inventors observe a reduction in the amount of LAMP1 in all 3 EOSPD lines consistent with the proteomics analysis (FIG. 4F). GCase is a class of lysosomal hydrolases that have been reported as having reduced activity in peripheral blood of some PD patients. In 30 day old DaNs from EOSPD patients, significantly reduced GCase activity was observed compared to controls (FIG. 4G). Others have found that reduced GCase activity in iPSC derived DaNs was caused by an increase in oxidized dopamine. However, a similar increase in oxidized dopamine was not seen in the Inventors' 30 day old PD DaNs (FIG. 4H). Taken with the significant downregulation of lysosomal pathway proteins, these results provided evidence of dysfunctional lysosomal degradation as the putative cause of α-Synuclein accumulation in EOSPD DANs.

Example 6

Modulation of PKC Signaling Rescues EOSPD Phenotypes

To test if the Inventors could reduce synuclein levels in the Inventors' EOSPD DANs through activation of lysosomal specific pathways, the Inventors selected 3 lysosomal agonists. The compounds the Inventors selected were: PEP005, a PKC agonist and structural analogue of the HEP14 drug, SMER28, a small molecule TFEB agonist shown to reduce Huntington and α-Synuclein aggregates in a PC12 cell model, and Trehalose, another biological compound shown to promote clearance of α-Synuclein. Starting at day 27, DaNs were treated for 3 days with the above lysosomal agonists. Treatment with both PEP005 and SMER28, but not Trehalose significantly reduced the amount of α-Synuclein protein in DaNs from control lines (FIG. 5A). However, in ESOPD DaNs, only the PKC agonist PEP005 substantially reduced synuclein levels. Interestingly in both control and PD DaNs, PEP005 treatment also resulted in an increased amount of TH enzyme present (FIG. 5A).

The interesting combined effects of lowering synuclein levels in both control and PD DANs while simultaneously increasing TH expression in response to PEP005, led us to investigate the mechanism of action of the drug. PEP005 is an established PKC delta agonist that results in a short burst of PKC phosphorylation followed by a strong reduction in phosphorylated PKC over longer times. At endpoint in this study, the Inventors observed increased basal levels of PKC alpha phosphorylation in untreated 190iPD DaNs (FIG. 5A) with PEP005 treatment completely ablating this signal in both control and PD DaNs (FIG. 5A, FIG. 5C).

Figures 5E, 5F:
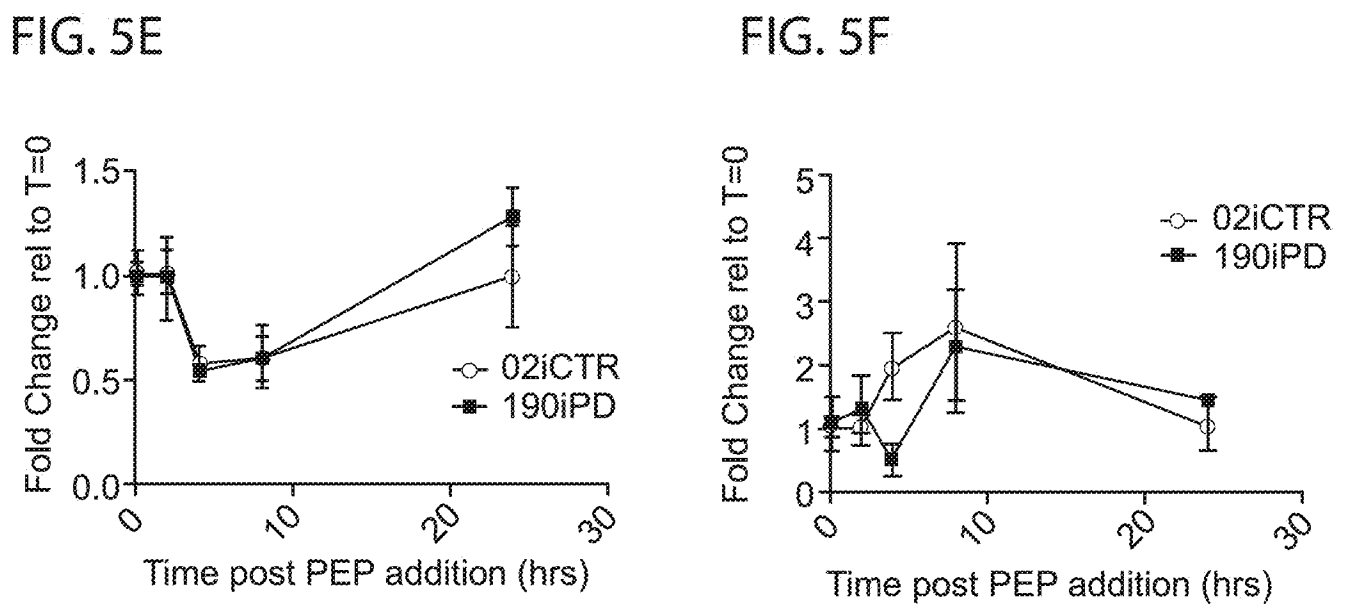
Figure 5G:
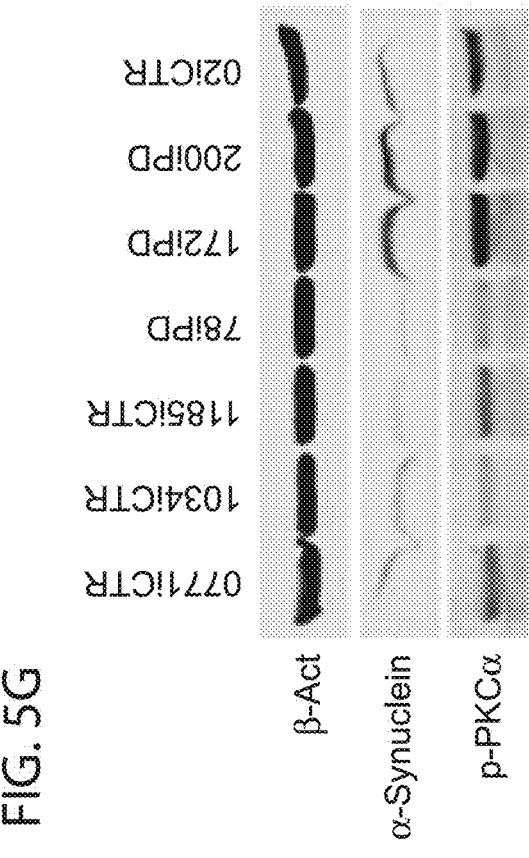

Having observed increases in phospho-PKCα at baseline in the 190iPD line, the Inventors checked all additional DANs to see if this observation was validated across multiple lines. The Inventors found higher levels of p-PKCα in 30 day DANs from all 3 EOSPD lines (FIG. 5B). The Inventors also checked 3 additional newly derived EOSPD lines (172iPD, 183iPD, 192iPD), 3 additional controls (0771iCTR, 1034iCTR, 1185iCTR), and a normal onset PD line (78iPD, age 67 @ onset, family history of PD) for both α-Synuclein accumulation and increased p-PKCα (FIG. 5G).

The elevated phosphorylation of PKCα was absent in the undifferentiated iPSCs and no clear pattern was evident in peripheral blood from the individual patients indicating specificity to the differentiated DaNs. Elevated phosphorylation of PKCα is clearly ablated by the addition of 1 uM PEP005 for 3 days in DaNs from all iPSC lines (FIG. 5C). While this ablation does correlate with reduced synuclein in all treated lines it appears that neither LAMP1 nor LC3 respond to PEP treatment in PD cells (FIG. 5C) indicating that the mechanism of action in the PD cells may be different from a canonical upregulation of lysosomal proteins. A time-course of PEP treatment in control and PD DaNs shows that both p-PKCα and α-Synuclein are degraded in response to drug treatment within about 24 hrs (FIG. 5D). This same timecourse also shows a marked decrease in cleaved caspase 3 (CC3) present in the PD cells. Gene expression data from paired samples along this same timecourse indicates that SNCA is downregulated 4 hours after PEP treatment (FIG. 5E) and TH is upregulated roughly 8 hours after initial exposure (FIG. 5F).

Example 7

In Vivo Reduction of α-Synuclein in WT Mice

In vivo, PEP stimulates synuclein degradation. Dosage studies of 0.3, 3, and 30 uM PEP was injected into the ventricles of WT mice. Reduction of synuclein and increase in TH in mouse striatum after 1 and 5 days post injection.

Example 8

Discussion

The Inventors began this study looking for a signature of parkinsonism in dopaminergic neurons differentiated from early onset sporadic PD patient iPSCs. In a random selection of patients with an early onset and no family history of PD, the Inventors reprogrammed PBMCs from 3 individuals. The resulting iPSC lines were genetically normal and lacked many of the known monogenic PD mutations. The genomic chip assay used to assess this covers ~260,000 known SNPs associated with neurodegenerative disorders. It is possible, if highly unlikely, that the 3 idiopathic individuals used to generate the PD iPSCs all have as yet unknown monogenic mutations that were missed by the NeuroX screen. Regardless, the complex background genetics of these EOSPD iPSCs resulted in the accumulation of α-Synuclein in DaNs at only 30 days of age. This is the first identified phenotype in iPSCs derived from sporadic Parkinson's patients.

The Inventors then moved to complete an in depth analysis of these differentiated cells using both transcriptomic and proteomic techniques. Transcriptomic analysis revealed increased expression of many synaptic and exocytic transcripts in the PD cells. These increased transcripts also directly translated to elevated protein levels in the PD DaNs indicating an overabundance of synaptic machinery. However, despite the presence of more synaptic machinery, neither MEA recordings or live calcium imaging demonstrated a difference in activity between the PD and control DaNs. Conversely, the proteomics data indicate a reduction in the amount of lysosomal lumen proteins in PD DaNs. This decrease was not reflected in the RNA of the same cells which indicates a disconnect in this signaling pathway. There is less protein but the cells are not responding to make more. This reduction in lysosomal proteins is further confirmed by the reduced in GCase activity in PD DaNs, reduced LAMP1 protein by western blot, and the accumulation of α-Synuclein under cycloheximide inhibition, all of which point to some deficit in protein degradation in the PD DaNs. This deficit also seems to be specific to lysosomal degradation pathways as inhibition of proteosomal degradation did not result in any change in α-Synuclein levels.

The Inventors next selected a series of lysosomal agonists to attempt to correct this observed deficiency. Of the 3 tested agonists, only the PEP005 small molecule reduced α-Synuclein levels in both control and PD DaNs. Interestingly, PEP treatment also resulted in an increase in the amount of TH present in the treated cultures of both control and PD DaNs. The dual effects of reducing intracellular α-Synuclein levels and increasing TH observed here make PEP005 a very attractive candidate as a potential therapeutic agent.

PEP005 (ingenol-3-angelate) is an FDA approved drug for topical treatment of actinic keratosis that also has anti leukemic activity and may play a role in reactivating latent HIV. Also known as ingenol-3-angelate and ingenol mebutate, it is the most studied ingenol derivative initially extracted from the sap of the plant *Euphorbia peplus*. This small molecule binds to the PKC C1 domains with subnanomolar affinity and shows no selectivity for individual PKC isoforms in vitro, although patterns of PKC isoform translocation and down-regulation induced by PEP005 can differ, sometimes in a cell line-dependent manner. It was selected in this study as a structural analogue derived from the same *Euphorbia peplus* plant as the HEP14 (5β-O-angelate-20-deoxyingenol) compound identified by Li and colleagues which acts as a TFEB agonist, independent of the MTOR pathway.

In control cells treated with PEP005, the Inventors observed an increase in the lysosomal protein LAMP1 consistent with activation of the lysosomal master regulator TFEB, but this increase does not appear to be replicated in the PD DaNs treated with the drug. PEP is described as both an activator of the pro-apoptotic PKCδ and an inhibitor of PKCa. PEP005 has been described as inhibiting proliferation of various cancer cell lines and primary acute myeloid leukaemia (AML) cells. In leukemic cell lines and primary AML cells, it induces apoptosis by activating PKCδ and by subsequently inducing sustained activation of ERK1/2.

In the Inventors' DaN cultures, the Inventors did not observe a strong PKCδ signal nor do the Inventors see an increase in LDH on drug treatment as might be expected if the Inventors were inducing cell death. In fact, the Inventors observed a decrease in the amount of active caspase 3 on drug treatment, although this effect is most easily observed in the PD DaNs which have higher levels of cleaved caspase 3 to begin with. It is likely that the toxicity of PEP is more specific to highly proliferative cells whereas the Inventors' differentiated neurons are largely post mitotic.

In investigating the mechanism of action of the PEP005 small molecule in the Inventors' DaNs, the Inventors observed increased levels of phosphorylated PKCα in the PD DaNs. It has been suggested that synuclein not only binds to and shares homology with the canonical 14-3-3 proteins involved with TFEB activation, but also binds PKCa, suggesting a link between the Inventors' observed synuclein accumulation, lysosomal biogenesis, and the PKC agonist PEP005. PKC couples activation of the TFEB transcription factor with inactivation of the ZKSCAN3 transcriptional repressor through two parallel signalling cascades. Activated PKC inactivates GSK3, leading to reduced phosphorylation, nuclear translocation and activation of TFEB, while PKC phosphorylate ZKSCAN3, leading to its inactivation by translocation out of the nucleus. PKC activation may therefore mediate lysosomal adaptation to many extracellular cues, including clearance of aggregated proteins, thereby providing viable treatment options for disease and disorders with a lysosome *nexus*, such as the Parkinson's mechanism outlined here.

α-Synuclein degradation has been controversial, but it appears that the bulk of degradation of at least monomeric WT α-synuclein in neuronal cell systems occurs through the lysosomal pathways of chaperone-mediated autophagy (CMA) and macroautophagy. Dysfunction of these degradation pathways may be a contributing factor to PD pathogenesis Here, targeting of PKC demonstrates the viability of strategies directed toward promoting endogenous degradation systems to enhance clearance of excess α-synuclein, and can have the advantage that they could also alleviate the aberrant effects of α-synuclein on their function This work is the first to identify a molecular signature of sporadic Parkinson's disease in iPSCs from early onset patients. The Inventors find that these cells accumulate α-Synuclein, have dysregulated lysosomal biogenesis and function, and also display more heavily phosphorylated PKC alpha. Taken together these three biomarkers give us a platform to screen for new therapeutic agents that may impact the underlying mechanisms in PD. The Inventors went on to identify a novel drug in PD that eliminates this signature and reduces intracellular α-Synuclein in both control and PD cells. These findings implicate a specific and novel drugable pathway that presents an opportunity to finally treat some of the underlying mechanisms of PD.

Example 9

Further Studies

The Inventors generated the first iPSC lines from a cohort of early onset sporadic PD (EOSPD) patients with no detected PD mutations. The Inventors were surprised to find that the majority of EOSPD patient iPSC-derived dopamine neuron cultures showed robust increases in α-synuclein and phosphorylated protein kinase C-α (p-PKCα) as well as decreases in important lysosomal proteins. Targeting these pathways with small molecules revealed that phorbol esters could reverse many of these disease-related phenotypes. The Inventors' findings demonstrate that EOSPD has a yet to be determined genetic basis that subsequently impairs lysosomal degradation of α-synuclein. The fact that specific phorbol esters can reverse this deficit highlights the potential of these drugs as a new treatment for EOSPD.

Further studies were organized as follows.

iPSC line generation: iPSC lines were generated by nucleofecting parent cells with non-integrating oriP/EBNA1 plasmids, which allowed for episomal expression of reprogramming factors as described previously in collaboration with the Cedars-Sinai iPSC Core.

iPSC maintenance, mDA neuron differentiation and drug treatments: iPSCs were maintained in E8 media on Matrigel and passaged every 5 days at split ratios from 1:6 to 1:12 as needed using Versene. Only iPSCs between passage 17 and passage 35 were used in this study. For differentiation, iPSCs were grown to ~80% confluency. Cells were singularized with Accutase (Millipore/Sigma #SCR005) (5 minutes at 37° C.) and plated onto Matrigel-coated 6-well plates (BD Biosciences) at 200K cells per cm² (for a fully confluent monolayer) in E8 media with 5 μM Y27632 (StemGent). 24 hours after plating, media was changed to Stage 1 (50% DMEM/F12, 50% Neurobasal, N2, B27-Vitamin A, LDN-193189 (LDN), SB431542 (SB)). Stage 1 media was changed each day (3 mL per well) for 3 days. Media was next switched to Stage 2 (50% DMEM/F12, 50% Neurobasal, N2, B27-Vitamin A, LDN, SB, Purmorphamine (PMN), CHIR99021 (CHIR), Sonic hedgehog (SHH), Fibroblast Growth Factor 8 (FGF8)). Stage 2 media was changed each day (3 mL per well) for 4 days. Media was then switched to Stage 3 (50% DMEM/F12, 50% Neurobasal, N2, B27-Vitamin A, LDN, CHIR, all-trans-Retinoic acid (ATRA)). Stage 3 media was changed each day (3 mL per well) for 4 days. Finally, media was switched to Stage 4 (50% DMEM/F12, 50% Neurobasal, N2, B27+Vitamin A, Brain-Derived Neurotrophic Factor (BDNF), Glial Cell Line-Derived Neurotrophic Factor (GDNF), dibutyryl cyclic-AMP sodium salt (dbCAMP), L-Ascorbic Acid (AA), γ-Secretase inhibitor (DAPT), CHIR, Transforming Growth Factor beta-3 (TGF β3)). Stage 4 media was changed each day (3 mL per well) for 3 days. On day 15, cells were dissociated to single cells using Accutase (20 mins at 37° C.) and gently lifted. Dissociated cells were resuspended in Maturation Medium (50% DMEM/F12, 50% Neurobasal, N2, B27+Vitamin A, BDNF, GDNF, dbCAMP, AA, DAPT, TGF3) plus 5 μM Y27632 and reseeded onto Matrigel-coated 6-well plates at 200 k/cm² in 1 mL total volume or onto Matrigel-coated L-glass coverslips in a 24-well plate at 200 k/50 μL drop. Cells were allowed to attach for 45 mins at 37° C. and Maturation Medium was then added to final volumes of 3 mL per well for 6-well plates or 1.5 mL per well for 24-well plates with coverslips. A full medium change was performed 48-hours post-seeding and medium was changed every 3 days until day 30. For drug treatments, cells at day-27 were fed with Maturation Medium containing the indicated drug and cells were analyzed at day 30. The drugs were: PEP005 (1 μM, Tocris, #4054), SMER-28 (5 μM, Tocris, #4297), Trehalose (25M, Sigma-Aldrich, #T0167), PMA (10 μM, Tocris, #1201) and Prostratin (PRO) (5 μM, Tocris, #5739).

TABLE 2

| Media Formulation | | |
| --- | --- | --- |
| Reagents List: | Supplier: | Working Dilutions: |
| DMEM/F12 | Life Technologies | 50% |
| Neurobasal | Life Technologies | 50% |
| N2 | Life Technologies | 1% |
| B27 - Vitamin A | Life Technologies | 2% |

TABLE 3

| Media Formulation | | |
| --- | --- | --- |
| B27 | Life Technologies | 2% |
| LDN-193189 | Stemgent | 1 μM |
| SB431542 | Tocris | 2 μM |
| PMN | Cayman Chemical | 2 μM |
| SHH | R&D Systems | 100 ng/mL |
| CHIR99021 | Cayman Chemical | 2.25 μM |
| FGF8 | R&D Systems | 100 ng/mL |
| ATRA | Sigma-Aldrich | 5 μM |
| Ascorbic Acid | Sigma-Aldrich | 500 ng/mL |
| BDNF | Peprotech | 20 ng/mL |
| GDNF | Peprotech | 20 ng/mL |
| dbCAMP | Sigma-Aldrich | .2 mM |
| TGF □3 | Cell Signaling Technology | 1 ng/mL |
| DAPT | Cayman Chemical | 2.5 μM |

Analytical flow cytometry: Day-30 cultures in 6-well plates were washed once in phosphate buffered saline (PBS) then 1 mL Accutase was added to each well and incubated for 25 mins at 37° C. or until the cells fully lifted. Cells were washed with an additional 2 mL Maturation Medium and very gently triturated until large clumps were no longer visible at which point cells were pelleted by centrifugation (1500 RPM for 3 mins). Cells were gently resuspended in 4% paraformaldehyde (PFA) in PBS and allowed to fix for 10-15 mins at room temperature. Fixed single cells were permeabilized using 1% Trition X-100 (Sigma-Aldrich) and stained using primary antibodies against TH (1:500 Immunostar, 22941), α-synuclein (1:1000 Abcam, ab138501), and MAP2ab (1:1000 Sigma-Aldrich, M1406), or isotype controls at same dilution (Cell Signaling IgG Isotype Control rabbit #3900S and mouse #5415S). Secondary antibodies (Alexa Fluor 488 and 594 donkey anti-mouse and donkey anti-rabbit, Invitrogen) were used at 1:500. Stained samples were quantified on an LSR Fortessa cytometer using BD FACSDiva software.

Dopamine detection: mDA neuron cultures were plated on L-glass coverslips and grown as above. For total dopamine, cultures were washed in artificial cerebral spinal fluid (aCSF) and immediately lysed in 200 μL of 0.2M perchloric acid/0.1 mM EDTA. Lysates were flash frozen in LN2. To detect released dopamine on day 30, culture media was aspirated and cells were washed twice with aCSF. After washing, 200 μL of aCSF was carefully plated on top of each coverslip, incubated at 37° C. for 15 mins, and collected. 200 μL of high K⁺ aCSF was then added to the top of each coverslip, incubated for 15 mins, and collected. Immediately after collection, 20 μL of 10× stabilization buffer (2M perchloric acid/1 mM EDTA) was added to each sample. Stabilized samples were snap frozen in LN2 and stored at −80° C. until HPLC (high performance liquid chromatography) analysis. Separation was performed on a 2.1×100 mm 3 μm reversed phase Hypersil ODS column with a mobile phase consisting of 75 mM sodium acetate, 0.75 mM sodium dodecane sulfonate, 2.5% acetonitrile, 12.5% methanol and 10 uM EDTA (pH=5.5) pumped at a rate of 0.2 ml/min.

Electrochemical detection of dopamine was conducted at a glassy carbon electrode held at a potential of 0.29V versus a Ag/AgCl reference electrode and provided a limit of detection of 0.1 nM for a 10 ul injection. Samples were analyzed in triplicate against known standard concentrations of dopamine.

Immunocytochemistry and imaging: mDA neuron cultures were plated on L-glass coverslips and grown as above. Day 30 neurons were fixed in 4% PFA at room temperature for 10-15 mins. Fixed coverslips were washed in PBS and permeabilized for 10 minutes at room temperature in 1% Triton X-100 in PBS, followed by staining in primary antibody solution (5% normal donkey serum, 0.125% Triton-X, PBS) overnight at 4° C. with the following antibodies: TH (1:5000, Immunostar #22941) and α-synuclein (1:500, Abcam #ab138501). Samples were washed 3 times in PBS and stained with species-specific Alexa Fluor 488 or 594-conjugated secondary antibodies (1:500, Invitrogen) for 2 hours at room temperature, followed by DAPI counterstain. Confocal Z-stack images were acquired using a A1 microscope (Nikon) with 40× and 20× objectives and rendered using maximum intensity projection through IMARIS software (Bitplane).

Western blot: Cells were gently scraped off the plates, washed with PBS, centrifuged at 15000 RPM for 1 min, and dry pellets were frozen at −80° C. Samples were then thawed and lysed using 1×NETN buffer (20 mM Tris-HCl (pH 8.0), 100 mM NaCl, 0.5 mM EDTA and 0.5% NP-40) supplemented with phosphatase/protease inhibitor cocktail (MS-SAFE, Sigma-Aldrich). Lysates were sonicated in an automated cold bath sonicator for 20 mins using alternating 10 sec pulses followed by 10 sec rests. Samples were centrifuged for 20 min at 4° C. at 15000 RPM. Total soluble protein concentrations were measured using a Bradford assay (BIO-RAD). 4× Laemmli sample buffer (BIO-RAD 161-0774) was added to either 100 μg or 50 μg of total protein extracts and samples were boiled for 5 min. Samples were run in 4-20% Mini-PROTEAN TGX Precast gels (BIO-RAD, 456-1094) and transferred to PVDF membranes using Trans-Blot Turbo Transfer System (BIO-RAD). Membranes were blocked with Odyssey blocking buffer (LI-COR) and then incubated with primary antibodies for overnight at 4° C. or room temperature for 3 hours. Following incubation with dye-labeled secondary antibodies for 2 hours at room temperature, signals were visualized using an Odyssey Fc imaging system (LI-COR). Primary antibodies used were human α-synuclein (1:1000, Abcam #ab138501), mouse α-synuclein (1:1000, Abcam #ab212184), TH (1:2000, ImmunoStar, #22941), total PKCα (1:1000, Cell Signaling, #2056S), p-PKCα 1:1000, Cell Signaling, #9375s), LAMP1(1:1000, Cell Signaling, #9091S), LCI/II (1:1000, Cell Signaling, #12741S), Cleaved Caspase 3-CC3 (1:1000, Cell Signaling #9661S), Synaptophysin (1:1000, Abcam, ab32127), P53 (1:2000, Santa Cruz, #sc-126), GAPDH (1:5000, Sigma-Aldrich, G8795) and β-actin (1:5000, Sigma-Aldrich, #A5441). Secondary antibodies were IRDye 680 RD goat anti-mouse and IRDye 800CW goat anti-rabbit, (LI-COR 926-68070 and 926-32211, respectively) at a dilution of 1:5,000. Combined α-synuclein and p-PKCα expression plots were calculated by first normalizing bands to β-actin, then to the 02iCTR signal present in each blot. All values were then compared across at least 3 independent differentiations for each line. ROC plot and area under the curve was determined using R package ROCR to determine predicative probability percentages.

qPCR: Total cellular RNA was isolated using TRIzol Reagent followed by Qiagen RNeasy Mini kit with DNase treatment. Total RNA (1 μg) was used for cDNA synthesis using the Quantitate Reverse Transcription Kit for cDNA synthesis for PCR (Qiagen). Real-time PCR was performed using the SYBR Green Supermix (BIO-RAD). The levels of expression of respective genes were normalized to corresponding GAPDH values and shown as fold change relative to the value of the control sample (ΔΔCt method)

NIRF detection of oxidized dopamine: Assay performed as described. Briefly, neurons were scrapped in cold PBS and centrifuged at 15000 RPM for 1 min. The cell pellet was frozen then thawed and homogenized in 1×NETN lysis buffer with phosphatase/protease inhibitor cocktail. Lysates were sonicated in a bath sonicator for 10 mins and spun at 15000 RPM for 15 min. Supernatant was removed and the insoluble pellets were resuspended in 18 MΩ di water. Total protein was measured using a Bradford assay and 100 μg of protein was brought up in 20 □L and dropped onto a Biodyne Nylon Transfer Membrane (Pall, #Pall-60209). Membranes were scanned using an Odyssey infrared imaging system (LI-COR) with the 700 channel. Samples were quantified by obtaining integrated spot intensities using Odyssey infrared imaging software, version 3.1.

GCase activity: Assay performed as described. Briefly, samples were lysed as above centrifuged at 15000 rpm for 15 min at 4° C. 50 μg of total protein was incubated in activity assay buffer (0.25% (v/v) Triton X-100, 1 mM EDTA, in citrate/phosphate buffer, pH 5.4) in 1% Bovine serum albumin (BSA), with 1 mM 4-Methylumbelliferyl β-glucophyranoside (4-MU, Sigma-Aldrich, #M3633) in 200 μl total volume. After 40 min incubation at 37° C., the reaction was stopped by the addition of equal-volume 1M glycine, pH 12.5. 100 μl replicates were loaded into white 96-well plates (Corning Assay plates) and fluorescence (ex=355 nm, em=460) was determined in a Molecular Devices SpectraMax i3 Multi-Mode microplate reader and SoftMax Pro software.

Transcriptomics: Triplicate wells of each line were differentiated as above and split into cell pellets for either mRNA sequencing or proteomic analysis. mRNA was isolated using methods described previously. Briefly, Library construction was performed using the Illumina TruSeq Stranded mRNA library preparation kit (Illumina). Briefly, total RNA samples were assessed for concentration using a Qubit fluorometer (ThermoFisher) and quality using the 2100 Bioanalyzer (Agilent Technologies). Up to 1 μg of total RNA per sample was used for poly-A mRNA selection. cDNA was synthesized from enriched and fragmented RNA using reverse transcriptase (Invitrogen) and random primers. The cDNA was further converted into double-stranded DNA (dsDNA), and the resulting dsDNA was enriched with PCR for library preparation. The PCR-amplified library was purified using Agencourt AMPure XP beads (Beckman Coulter). The concentration of the amplified library was measured with a Qubit fluorometer and an aliquot of the library was resolved on a Bioanalyzer. Sample libraries are multiplexed and sequenced on a NextSeq 500 platform (Illumina) using 75 bp single-end sequencing. On average, about 20 million reads were generated from each sample.

Raw reads obtained from RNA-Seq were aligned to the transcriptome using STAR (version 2.5.0) 62/RSEM (version 1.2.25) 63 with default parameters, using a custom human GRCh38 (or mouse CRCm38) transcriptome reference downloaded from www.gencodegenes.org, containing all protein coding and long non-coding RNA genes based on human GENCODE version 23 (or Mouse GENCODE M8) annotation. Expression counts for each gene (TPM: transcripts per million) in all samples were normalized by the sequencing depth. To determine detected transcripts, a filter of >0.1TPM in at least 9 samples was used as a threshold for detection of a unique transcript (Cluster 3.0). PCA was conducted on log transformed data using Cluster 3.0 software. All transcriptomic data from this study is available in the GEO repository under GSE120746.

Proteomics: Frozen pellets were lysed using 2% SDS+10 mM TCEP (tris 2-carboxyethyl phosphine) buffer and sonicated. The bicinchoninic acid assay (BCA assay, Pierce, #23225) assay was used to determine protein concentration and 125 μg of protein were digested using FASP Protein Digestion kits (Expedeon). 3.125 μg of trypsin/lysC was used to digest each sample overnight at 37° C. with shaking at 1000 rpm. Samples were desalted using Oasis MCX μelution plate and were eluted with 300 μl of Methanol/Ammonium Hydroxide. Samples were dried in a SpeedVac until dry and resuspended in Biognosys iRT solution. Sample/iRT solution (4 μg) was loaded onto an Eksigent 415 LC connected to a 6600 TripleTOF (Sciex) operating in micro-flow mode. Peptides were pre-loaded onto the trap column (ChromXP C18CL 10×0.3 mm 5 μm 120 Å) at a flow rate of 10 μL/min for 3 min and separated on the analytical column with a temperature of 30° C. (ChromXP C18CL 150×0.3 mm 3 μm 120 Å) and a flow rate of 5 μL/min. For DIA samples, the peptides were separated using a linear A-B gradient composed of 3-30% A for 38 min, 30-40% B for 5 min, 40-85% B for 2 min, an isocratic hold at 85% for 3 min, and re-equilibrating at 3% A for 8 min. Data was acquired using from 400-1250 m/z with an MS1 scan of 150 ms and 100 variable window MS2 scans of 25 ms. Source parameters were set to the following values: Gas 1=15, Gas 2=20, Curtain Gas=25, Source temp=100, and Voltage=5500V. DDA samples were run using a linear A-B gradient composed of 3-35% A for 60 min, 35-85% B for 2 min, then and isocratic hold at 85% for 5 min with re-equilibrating at 3% A for 7 min. For DDA acquisition MS1 scans were acquired using a dwell time of 250 ms in the mass range of 400-1250 m/z and the top 50 ions reaching a threshold of 100 counts per second were selected for fragmentation. MS2 scans were acquired in high-sensitivity mode with dynamic accumulation option turned on with a dwell time of 25 ms for ions ranging from +2 to +5 using rolling collision energy and a collision energy spread of 5. Ions were excluded for fragmentation after one occurrence for a duration of 15 seconds. DIA files were compared the DDA library using OpenSWATH as previously outlined. MS2 normalized transition level data was run through MAP DIA software to obtain normalized peptide and protein level data. In addition, differential protein analysis was performed by MAP DIA. To filter out any peptides that had high variance within triplicates, a CV filter was applied where peptides that had a CV above 20% within each technical replicate were excluded. Peptide level data was then summed to give protein level data. This data was then used for downstream analysis, including principal component analysis, GSEA and STRING. The mass spectrometry proteomics data have been deposited to the ProteomeXchange Consortium via the PRIDE partner repository with the dataset identifier PXD011326.

GSEA and STRING analysis: Gene set enrichment analysis (GSEA) was conducted as previously described 68. For matched analysis of mRNA-Seq and proteomic data, matching genes found in both data sets were analyzed independently in GSEA. Preranked PC1 gene weightings from each independent PCA analysis were run on Gene Ontology (GO) and KEGG databases using GSEA algorithm. Resulting ranked pathway lists from RNA-Seq and proteomic analysis were matched using R software and ranked by significance calculated by FDR. Predetermined differentially expressed protein list from MAP DIA was used with STRING protein:protein interaction online tool to give high confidence protein:protein interactions and enrichments against the whole genome.

MEA recordings: Cells were plated on 48-well microelectrode array (MEA) plates (Axion Biosystems) at day 15 of differentiation. Spontaneous activity was measured daily for 5 minutes on the Maestro MEA platform (Axion Biosystems). Wave form events were identified using adaptive spike threshold crossing with a standard deviation of electrode noise set at 6, and events were further sorted using Offline Sorter v.4 (Plexon). A minimum of 5 spikes per minute was used to include for analysis.

Patch clamp: Whole-cell patch clamp was performed on cultures around day 30 that had been plated on L-glass coverslips. Cells were placed in phenol red-free brain phys medium (STEMCELL Technologies, 5790) at room temperature and maintained for up to two hours during acquisition. Glass pipettes were pulled using a Sutter Instruments P-1000 with a tip resistance of 4-5 MΩ. Internal solution comprised (in mM): 112.5 K-gluconate, 4 NaCl, 17.5 KCl, 0.5 CaCl2, 1 MgCl2, 5 ATP, 1 NaGTP, 5 EGTA, 10 HEPES. Voltage- and current-clamp recordings were performed using a Multiclamp 700B amplifier, Digidata 1300 and PClamp 10 acquisition software (Molecular Devices). Neurons with an access resistance above 30 MΩ, or whose resistance changed more than 4 MΩ during recording, were excluded. The resting membrane potential (RMP) was measured during current clamp by averaging a continuous voltage recording a 0 pA. Voltage-gated sodium and potassium currents were measured from a holding voltage of −70 mV and then stepped from −120 mV to 40 mV in 10 mV increments over 100 ms. Induced action potentials were measured in current-clamp where the holding current was adjusted to maintain a constant −60 mV baseline voltage across cells, and then incrementing steps of 10 pA were applied over 500 ms.

In silico modeling of PKC-PEP005 protein complex: Putative binding of PEP005 to PKC was determined using homology modeling followed by docking studies. Briefly, the C1 domain of PKC complexed with 12-acetylphorbol was used as a template (PDB: 1PTR) 69. The model structure of PKC□ was developed by homology modeling using Rosetta 70. The top three-dimensional models (out of 5 predicted structures) of PKC were then used to assess the binding of PEP005 using Glide 71. The best binding orientation of PEP005 was selected based on Glide XP score. Other putative protein targets for PEP005 were explored using DALI 72 based on the three-dimensional structure of the C1 domain of PKC.

In vivo assessment of PEP005 activity: Wild-type C57BL/6 mice (Jackson labs) were used and all animal work was done in accordance with IACUC 6462 at Cedars-Sinai Medical Center. PEP005 was diluted to 10, 1, or 0.1 mM in 0.9% sterile saline solution. Vehicle (DMSO) was diluted to 10 mM in 0.9% sterile saline solution. Mice were given a single 2 μl injection into the left striatum at the following coordinates: 0.7 mm AP and 2.5 mm ML from bregma, and 3.5 mm DV from dura. Animals were sacrificed 3 days after injection. For immunohistochemistry (IHC) analysis, mice were perfused with 4% PFA/PBS and whole brains were extracted and post-fixed in 4% PFA overnight at 4° C. Brains were then rinsed with PBS and stored in 30% sucrose at 4° C. Brains were sectioned at 30 μm using a microtome and collected as free-floating sections. Striatal sections were washed with PBS three times for 5 min and quenched with 0.3% H2O2 for 30 min. Sections were washed with 0.005% TritonX-100 in PBS (PBS-T) three times for 5 min and blocked in a solution of 3% Normal Horse Serum (NETS) and 2% BSA in PBS-T for 1 hour at room temperature, followed by overnight incubation at room temperature in α-synuclein antibody (1:300, Abcam #ab212184) in blocking solution. The slides were washed with PBS-T three times for 5 min and incubated with biotinylated anti-rabbit IgG (Vector, BA-1000) in blocking solution. Sections were then washed with PBS-T three times for 10 min, incubated for 45 min with Avidin Biotin Complex (Vector, VECTASTAIN ABC Kits (HRP), #AK5000) and the signal was visualized using DAB (3,3'-Diaminobenzidine) (1:500, Vector SK4100). For western blot analysis, mice were perfused with PBS and the left and right striatum were dissected. Individual striatal hemispheres were immediately homogenized and lysed in 1×NETN buffer supplemented with phosphatase/protease inhibitor cocktail. Lysates were sonicated by sequential probe then bath sonication and centrifuged at 4° C. for 20 mins at 15000 RPM. Total protein (50 μg) from each lysate was run on 4-20% Mini-PROTEAN TGX Precast gels and transferred to PVDF membranes. Mouse specific α-synuclein (Abcam #ab212184) and β-actin antibodies were used. Proteins band were quantified by the LI-COR software to show relative synuclein levels (α-synuclein/β-actin) for the injected (L) relative to the contralateral side (R).

Example 10

Generation of iPSCs from Early Onset Sporadic Parkinson's Disease Patients

The Inventors initially collected peripheral blood mononuclear cells from three EOSPD patients (ages 30-39) with no known family history of PD (190iPD, 194iPD, 200iPD). These cells were reprogramed to iPSCs using established non-integrating episomal techniques. The iPSC lines expressed pluripotency markers and were karyotypically normal. Analysis with the NeuroX platform detected no causal monogenic mutations in the established PD genes— EIFG1, PARK2, LRRK2, GBA, SNCA, PINK1, PARK7, VSP35, ATP13A2—or multiplications of the SNCA locus in the patient lines (data not shown). Patient presentations included tremor-predominant, akinetic-rigidity, or a mixed phenotype, and all had asymmetrical onset with a corresponding asymmetrical deficiency in striatal DAT uptake to confirm PD diagnosis. Three control iPSC lines were also generated from the blood or fibroblasts of individuals with no neurological disease at time of collection (02iCTR, WP3iCTR, 00iCTR).

Example 11

Efficient Differentiation of iPSCs to mDA Cultures iPSC lines from both EOSPD and control patients were differentiated to midbrain dopaminergic (mDA) neural cultures using a modified 30 day protocol based on Kriks et al 31. Day 30 differentiated cultures expressed mature neural markers (PAX6, NEFH), neuronal markers (TUB3 and MAP2) and, importantly, dopaminergic neuron markers including tyrosine hydroxylase (TH), Nurr1, DAT, and GIRK231-33. Immunostaining confirmed TH production in all 6 lines. Flow cytometry quantification showed similar numbers of TH-expressing cells between control and EOSPD lines however, a comparison of individual lines revealed that one EOSPD line, 190iPD, yielded significantly fewer TH-positive neurons when compared to the 02iCTR line. No other inter-line differences were significant. To determine whether EOSPD altered dopamine content and/or release, extracts and effluents of mDA cultures were analyzed by HPLC. When normalized to the number of TH-expressing neurons, all lines produced and released dopamine at similar levels. To determine the electrophysiological function of EOSPD developing neurons, patch clamp and multi-electrode array (MEA) recordings were conducted over time in culture. Spontaneous activity from MEA recordings was observed at day 21 of differentiation and by day 30, both EOSPD and control cells produced coordinated bursts of activity. When activity was quantified across all lines, a similar number of spontaneous spikes were observed between disease and control mDA cultures. Neurons patched at day 30 exhibited spontaneous activity with large voltage-gated sodium and potassium currents, and elicited trains of action potentials upon current injection, indicative of mature neurons. Together, these data demonstrate that iPSCs derived from EOSPD patients differentiated efficiently into functional dopaminergic neurons and possessed similar neuronal profiles to control lines, suggesting that these phenotypic measures did not provide a disease-specific signature.

Example 12

α-Synuclein Accumulates Specifically in EOSPD mDA Cultures

In order to determine if α-synuclein was differentially expressed in EOSPD-derived mDA cultures, quantitative PCR was conducted. Relative to control cultures, SNCA gene expression was not significantly increased in EOSPD mDA cultures. The Inventors also sought to confirm whether α-synuclein protein accumulation was similar. Interestingly, western blot analysis showed that EOSPD mDA cultures had significantly increased α-synuclein protein levels compared to controls. A subsequent ELISA on cell lysates confirmed significantly increased levels of α-synuclein protein in diseased lines compared to controls. Protein lysates from the EOSPD lines at the iPSC stage did not exhibit increased α-synuclein, indicating accumulation was specific to the differentiated cultures. Collectively, these data indicate a phenotype of transcription-independent accumulation of α-synuclein protein in EOSPD patient-derived mDA cultures.

Example 13

Lysosomal Proteins are Dysregulated in EOSPD mDA Cultures

The Inventors next sought to determine what factors may have contributed to this α-synuclein increase through both RNA sequencing and proteomics on a paired sample set derived from the same culture wells. Whole transcriptomic RNA sequencing (RNA-Seq) detected 19004 unique transcripts between EOSPD and control mDA cultures while data independent acquisition mass spectrometry (SWATH) proteomic analysis identified 2478 unique proteins. Independent unsupervised principal component analyses (PCA) of both transcriptomic and proteomic data revealed a clear delineation between the EOSPD cells and controls along principal component 1 (PC1).

Given the similarity between transcriptomic and protein signatures, the Inventors compared the two datasets along PC1 to identify both concordant and discordant cellular pathways that could contribute to α-synuclein accumulation in EOSPD mDA cultures. To enable direct comparison of pathways, PCA was repeated on 2440 genes and corresponding proteins that were present in both data sets. PC1 ranked genes and proteins from this matched list were analyzed in separate gene set enrichment analyses (GSEA) and compared by term significance. GSEA run on the entire RNA-Seq data set yielded similar significant terms. α-synuclein and other synaptic vesicle genes related to dopamine release such as Synapsin (SYP), Synaptic vesicle 2A (SV2A), and SNAP25 were contained in the Go Presynapse term, which was significantly upregulated in both RNA and protein. Metabolic genes contained in KEGG Oxidative Phosphory-lation were also significantly upregulated in EOSPD lines in both mRNA and protein. In protein data, terms related to neurodegenerative disease such as Parkinson's, Alzheimer's and Huntington's Disease were significantly upregulated in EOSPD lines, suggesting that common aspects of neurodegeneration had been captured.

Both transcripts and proteins found in the Go Endoplasmic Reticulum Lumen term were significantly downregulated, suggesting deficiencies in genes related to proteogenesis. Interestingly, lysosomal proteins found in the Go Lysosomal Lumen term were significantly downregulated in protein, but not in mRNA data. To confirm that dysregulated pathways found in PC1 were specific to EOSPD lines, a separate analysis of differential expression between control and EOSPD lines was performed with proteomic data and entered into STRING pathway analysis. Again, lysosomal proteins were found to be significantly reduced in EOSPD lines. These data indicated that while EOSPD mDA cultures had normal transcription of lysosomal machinery, fewer resulting proteins were present compared to control mDA cultures.

The reduction in lysosomal proteins in EOSPD mDA cultures suggested that α-synuclein accumulation could be the result of impaired degradation. To test overall degradation rates, global transcriptional function was inhibited in culture for 48 hours via cycloheximide treatment and protein was assessed and quantified over time. Over the course of the 48-hour treatment, α-synuclein degraded in the 02iCTR control line with an observed half-life of approximately 10 hours, slightly longer than previously reported in PC12 cells. In stark contrast, α-synuclein accumulated in the most severe EOSPD line (190iPD) over the course of cycloheximide treatment. However, diseased and control lines displayed similar protein degradation rates for other proteins relevant to dopamine neurons, such as TH and synaptophysin, suggesting that the deficit in degradation was specific to α-synuclein protein degradation can be largely divided into proteosomal and autophagy/lysosomal degradation pathways. To determine if proteosomal degradation was responsible for α-synuclein proteolysis, mDA cultures were treated with the proteasome inhibitor MG132 for 24 hours. MG132 treatment resulted in accumulation of P53, a protein canonically degraded via proteosomal means. However, there was no significant increase in α-synuclein in either control or EOSPD cultures, indicating that degradation of α-synuclein was not mediated through the proteasome in this context. To determine potential lysosomal involvement in α-synuclein degradation 36,37, the Inventors next probed for lysosomal-associated membrane protein 1 (LAMP1). A significant reduction in the amount of LAMP1 was detected in all 3 EOSPD lines, which was consistent with the proteomics analysis. GCase is a lysosomal hydrolase reported to have reduced activity in peripheral blood of some PD patients. Using 1 mM 4-Methylumbelliferyl β-glu-cophyranoside to quantify relative GCase function, the Inventors found a significant reduction in activity in EOSPD mDA cultures compared to controls. In a previous study using non-early onset sporadic patient iPSC lines, reduced GCase activity in differentiated neural cultures was caused by an increase in oxidized dopamine at later culture time points (>60 days) 42. In contrast, at 30 days in culture, the Inventors did not observe any increase in oxidized dopamine. When grown for longer time periods (60 days), however, oxidized dopamine began to accumulate in the EOSPD cultures. These results suggest that in this model, increased α-synuclein and lysosomal deficiencies precede accumulation of oxidized dopamine. This provides further evidence of dysfunctional lysosomal degradation as the putative cause of α-synuclein accumulation in EOSPD mDA cultures.

Example 14

PEP005 Modulates EOSPD Phenotypes

The Inventors next tested the possibility of reducing α-synuclein levels through activation of lysosomal-specific pathways using three lysosomal agonists 43. The compounds selected were: PEP005, a PKC agonist and structural analog of the HEP14 drug, SMER28, a small molecule autophagy promoter shown to reduce Huntingtin and α-synuclein aggregates in a PC12 cell model, and Trehalose, another compound shown to promote clearance of α-synuclein in PC12 cells 46. mDA cultures from a control line, 02iCTR, and an EOSPD line, 190iPD, were treated with each agonist for three days starting at day 27 of differentiation. Interestingly, treatment with PEP005 and SMER28, but not Trehalose, reduced the amount of α-synuclein protein in control cultures. In PD mDA cultures PEP005 and Trehalose, but not SMER28, reduced α-synuclein levels. However, only the PKC agonist PEP005 reduced α-synuclein levels in both PD and control EOSPD mDA cultures. A surprising additional finding was that in control and EOSPD mDA cultures, PEP005 treatment also resulted in an increase in the amount of TH enzyme present. Immunostaining confirmed that individual PEP005-treated mDA cultures displayed enhanced TH and decreased α-synuclein. As the high density of immunostained mDA cultures precluded quantification, flow cytometry was instead used to quantify TH. PEP005-treated cultures did indeed contain neurons with significantly higher levels of TH expression, however PEP005 did not result in an increased number of TH neurons. These data show that PEP005 enhanced the levels of TH expression in neurons already producing the enzyme while at the same time reduced the expression of abnormally high levels of α-synuclein.

PEP005 has well-established activity against both PKC alpha (PKCa) and delta (PKC6). Though the two isoforms are antagonistic with each other, literature reports treatment with PEP005 results in a short burst of PKC phosphorylation followed by a strong reduction in phosphorylated PKC over longer times. The Inventors were surprised to find that at day-30, basal levels of phosphorylated PKC-α (p-PKCa) were higher in 190iPD mDA cultures compared to controls and that PEP005 treatment could completely ablate this signal in both control and EOSPD cultures. Assessment of all other lines used in this study confirmed that there were higher levels of p-PKCα in mDA cultures from all 3 EOSPD lines when compared to the control lines, although differences in total PKCα were not significant. The elevated p-PKCα was absent in the undifferentiated iPSCs and no clear pattern was evident in peripheral blood from the individual patients (data not shown), indicating specificity to the differentiated mDA cultures. In addition, this elevated p-PKCα was ablated by the addition of 1 μM PEP005 for 3 days in mDA cultures from all iPSC lines. This ablation was coupled with a decrease in α-synuclein levels and an increase in LAMP1.

In order to further evaluate the response to PEP005, a time-course of treatment in control and EOSPD mDA cultures was assessed and showed that both p-PKCα and α-synuclein were degraded in response to drug treatment within about 24 hours. Within the same time course, there was also a marked decrease in cleaved caspase 3 (CC3) in the EOSPD mDA cultures, indicating the absence of a toxic response to the drug. Gene expression data from paired samples showed that SNCA expression was downregulated 4 hours after PEP005 treatment and TH was upregulated roughly 8 hours after initial exposure, suggesting an antagonistic link between the two proteins 48-50.

Example 15

Confirmation of EOSPD Phenotypes in Additional Patients

The Inventors next wanted to confirm these findings in a wider range of control and EOSPD patients. The Inventors derived an additional 2 EOSPD lines (172iPD, 192iPD) as well as 3 control lines (0771iCTR, 1034iCTR, 1185iCTR) from the Lothian birth cohort, a group of individuals who have all reached 83 years of age with no signs of neurodegeneration or cognitive decline 51. The Inventors also evaluated a normal onset PD line (78iPD, symptom onset at age 67 and a family history of PD) to see if these phenotypes could be identified in the PD population at large. iPSCs from all new lines were differentiated to mDA cultures and probed for both α-synuclein accumulation and increased p-PKCα at day 30. Confirming the Inventors' earlier findings, cells from the Lothian controls did not accumulate α-synuclein or display increased p-PKCα while those from one (172iPD) of the two new EOSPD lines showed both phenotypes. Interestingly, mDA cultures from the normal onset PD line and one of the new EOSPD lines did not display either α-synuclein accumulation or increased p-PKCa. To compare all western data across the lines, expression values were normalized to 02iCTR in each blot. mDA cultures from control individuals revealed similar α-synuclein and p-PKCα expression, while most EOSPD patients resolved in a separate cluster. To determine the potential of α-synuclein and p-PKCα expression detection as a predictive tool for EOSPD, the Inventors plotted the normalized expression values on a receiver operating characteristic curve (ROC). The predictive accuracy of distinguishing EOSPD from controls, reflected in the area under the curve, was for 0.84 for α-synuclein (red), 0.93 for LAMP1 (blue), and 0.96 for p-PKCα (orange) indicating that these phenotypic markers can accurately segregate the patients in the Inventors' cohort.

Example 16

Additional Phorbol Esters Alter α-Synuclein and TH Levels in mDA Cultures

To further probe the mechanism of interaction between PEP005 and α-synuclein, the Inventors tested two additional PKC agonists with similar chemical structures to PEP005: Phorbol 12-myristate 13-acetate (PMA) and Prostratin (PRO). Both additional phorbol ester compounds, PMA and PRO, exhibited similar activity to PEP005; with treatment of mDA cultures resulting in a reduction of p-PKCα and α-synuclein with corresponding increases in TH.

Example 17

PEP005 Modulates α-Synuclein Independently of p-PKCα

To determine optimum potency, the Inventors conducted a set of dose response studies examining p-PKCα and α-synuclein expression in response to both PEP005 and PRO. Evaluating mDA cultures treated with PEP005 revealed a clear dose-response relationship of the drug's direct target p-PKCa. However, a robust reduction in α-synuclein was observed at low PEP005 doses that did not alter p-PKCα levels. This suggests that the mode of action for PEP005 in reducing α-synuclein may be independent from p-PKCa. PRO decreased both p-PKCα and α-synuclein in a dose-dependent manner but was not as efficient as PEP005 in decreasing α-synuclein levels, suggesting a lower affinity interaction with α-synuclein modulating pathways.

Given the differential response of α-synuclein and p-PKCα to PEP005 at low doses, and the fact that additional drugs had a similar effect to PEP005 treatment, the Inventors performed in silico modeling of potential PEP005 binding sites to identify new drug binding partners. As expected, the Inventors confirmed several similar affinity target sites for PEP005 binding to PKCa, but interestingly the Inventors also found binding sites on multiple additional proteins. One of the more interesting findings, based on a 3-dimensional model, was binding to the GTPase RAS with similar affinity to PKCα. RAS has a direct impact on cell proliferation (MAPK pathway) and lysosomal biogenesis through the mTORC pathway.

Example 18

PEP005 Reduces α-Synuclein Levels In Vivo

Finally, the Inventors wanted to assess if PEP005 could also reduce α-synuclein levels in vivo. To do this, adult wildtype C57BL/6 mice received unilateral striatal injections of PEP005 (2.15 ng, 21.5 ng or 215 ng). Both western blot and immunohistochemical assessment of the mouse striatum at 3 days post-treatment showed that the 215 ng dose of PEP005 significantly reduced α-synuclein levels relative to the contralateral side. These results demonstrate that PEP005 activity reduces α-synuclein levels in vivo.

Example 19

Discussion

The cause of PD is proposed as either genetic, environmental, or some combination of the two and in nearly all cases involves the abnormal accumulation of α-synuclein. The Inventors focused on early onset sporadic patients (3-10% of the United States PD population) and have now identified a reliable molecular signature in iPSC-derived mDA cultures from four out of five patients in this study. As iPSC conversion wipes out most epigenetic memory this molecular signature means that there must be a strong genetic contribution to EOSPD, presumably involving a number of as yet unknown pathogenic and modifying genes. Accumulation of α-synuclein was not observed in an adult onset patient in the current study, nor in previous adult onset sporadic PD studies. The failure of adult onset PD cells to reproduce EOSPD phenotypes indicates that either more time in culture may be necessary to manifest these in vitro phenotypes or, alternatively, that the accelerated nature of EOSPD provides a distinct subpopulation of PD with a deficiency in handling α-synuclein that can be readily reproduced in vitro.

Genome wide association studies (GWAS) on large cohorts of sporadic patients have identified allelic variants relating to protein degradation, implicating lysosomal degradation pathways in disease pathogenesis. The Inventors' results support this and many previous studies that point toward lysosome dysfunction as major contributor to PD. While the EOSPD patients did not carry lysosomal risk variants, or display altered lysosomal gene expression at the transcript level, lysosomal proteins were significantly downregulated. Downregulated lysosomal proteins coupled with downregulated pathways related to protein processing, as found in the endoplasmic reticulum lumen, suggest that lysosomal protein biogenesis and/or stability may contribute to EOSPD specific accumulation of α-synuclein. By directly stimulating lysosomal pathways the Inventors were able to effect a decrease in intracellular α-synuclein protein. However, treatment with phorbol ester compounds not only induced a reduction in α-synuclein levels but also resulted in an increase in the amount of TH present in mDA cultures of both control and PD origin. Other studies have suggested an antagonistic link between α-synuclein and TH expression however, as increased TH was specific to the PEP treatment, the interaction may be more complex than a simple direct link. Control mDA cultures treated with the SMER-28 small molecule and PD mDA cultures treated with Trehalose did show a reduction in the amount of α-synuclein protein but, unlike with the phorbol esters, neither reduction resulted in an increase of TH enzyme. These divergent results suggest that the two pathways may converge around a common target but are otherwise independent.

The dual effects of reducing intracellular α-synuclein levels and increasing TH observed here make PEP005 a very attractive candidate as a potential therapeutic agent. PEP005 is an FDA-approved drug for topical treatment of actinic keratosis that also has anti-leukemic activity and may play a role in reactivating latent HIV. It was selected in this study as a structural analogue derived from the same plant as the HEP14 compound that acts as a TFEB agonist, independent of the mTORC pathway. In control and PD cells treated with PEP005, the Inventors observed an increase in the lysosomal protein LAMP1 consistent with activation of the lysosomal master regulator TFEB. Network analysis of proteomic data also suggested TFEB to be central to the downregulation of lysosomal pathways in EOSPD mDA cultures. However, the rapid reduction of α-synuclein after PEP005 treatment both in vitro and in vivo would suggest that transcription of new lysosomal proteins is not initially responsible for the immediate decrease in α-synuclein.

Investigating the mechanism of action of the PEP005 small molecule revealed increased levels of p-PKCα that were specific to the EOSPD mDA cultures. While associated with certain cancers, this is a novel signal in the PD literature and the Inventors pursued this signal as a biomarker and potential cause of the accumulating α-synuclein observed in EOSPD mDA cultures. Three of the Inventors' tested PKC agonists (the three phorbol esters) all resulted in a decrease in p-PKCa, which was accompanied by reduced α-synuclein and increased TH levels. Additionally, the dose response studies indicate that PEP005 can alter α-synuclein levels without substantially affecting p-PKCa. These results would suggest that some interaction specific to the structure of the phorbol ester compounds is driving the decreased α-synuclein and not the reduction of p-PKCa.

The inherent patient specificity of this model presents the opportunity for EOSPD diagnostics and therapeutic development. More patient lines will be required to fully evaluate the predictive accuracy of this approach to aid in EOSPD diagnosis. While the model accurately distinguished most of the EOSPD patients, one patient was not correctly identified. This lack of phenotype in vitro coincided with a unique clinical feature, namely a non-tremor predominant presentation. This patient's divergent clinical features and in vitro results suggest a possible alternative etiology or unique set of modifying genes that could alter the timing or acquisition of EOSPD biomarkers.

This work is the first to identify a molecular signature of sporadic Parkinson's Disease in iPSCs from early onset patients. These cells accumulate α-synuclein, have dysregulated lysosomal biogenesis and function, and also display increases in p-PKCα, providing biomarkers that could allow us to predict whether a young patient presenting with motor symptoms has EOSPD and thus represents a new diagnostic tool for clinicians. This system also presents a platform to screen new therapeutic agents that may impact the underlying mechanisms in EOSPD. For example, the Inventors have already identified a novel set of drugs that target this signature and reduce intracellular α-synuclein in both control and PD cells. These phorbol ester drugs, in particular PEP005, may treat the underlying cause of EOSPD and could uncover shared principals with other neurodegenerative disorders.

Example 20

Treatment and Administration

The Inventors note that in vitro blood plasma binding studies in multiple animal models (rat, rabbit, mini pig, and human) show highly efficient plasma binding of PEP005 and an additional phorbol compound. This may complicate IV delivery.

In multiple IV bolus dose studies, the following was observed. Respiratory effects in Rat—no biologically relevant responses were observed at doses up to 10 ug/kg. Cardiovascular effects in mini-pig—Doses up to 5 ug/kg (highest tested) produced no adverse clinical or behavioral effects and produced no notable cardiovascular changes.

For dose ranging studies in rat and mini-pig. Repeated doses up to 15 ug/kg/day for 7 days were tolerated in rats, 5 ug/kg in pigs In a repeat dose tox study in rats—animals were given up to 10 ug/kg/day for 7 days by IV tail vein injection. All doses were well tolerated. In a repeat dose tox study in mini-pigs—animals were given up to 5 ug/kg/day IV approximately 1×/week. Treatment with the 5 ug/kg dose resulted in lower food intake the following day after which intake recovered.

In a study to determine PK profile of PEP in mice—10 and 50 ug/kg were administered by IV tail vein injection. Serum concentration was below detectable limits 1 hour after testing indicating very high clearance (>blood flow through the liver). Again potentially problematic for IV delivery.

Synthesizing the above results, the Inventors will directly test tail vein IV admin at the 10 ug/kg dose range to see if the Inventors can generate a measurable effect on brain synuclein levels. However, given the high binding and very fast clearance/metabolism rates I think IV admin is likely not an efficient route of delivery. The other route of delivery the Inventors would be looking at is direct infusion into the brain.

To determine a dosing scheme for our future animal studies the Inventors needed to know how long the effects of a single PEP dose last. This study shows the duration of activity for a single 24-hour dose of PEP005. Synuclein levels remained depressed for 168 hours and pPKCα levels were still depressed after 240 hours post dose. Therefore, the Inventors are looking at dosing animals roughly 1×/week.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without are the compositions and methods related to induced pluripotent stem cells (iPSCs), differentiated iPSCs including midbrain neurons, floorplate neurons, dopaminergic neurons, techniques and composition and use of solutions used therein, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment.

In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of treatment of a subject afflicted with early onset sporadic Parkinson's Disease (EOSPD) by modulating activities of α-synuclein and tyrosine hydroxylase (TH) such that activity of α-synuclein is downregulated and activity of tyrosine hydroxylase (TH) is upregulated in the subject, the method comprising:

administering a pharmaceutical composition comprising a therapeutically effective agent and a pharmaceutically acceptable carrier to the subject, thereby treating the subject, wherein the therapeutically effective agent comprises a phorbol ester compound, ingenol-3-angelate (PEP005), wherein the subject with symptom onset prior to 50 years of age with no reported familial history of Parkinson's Disease or no known Parkinson's Disease mutations has upregulation of phosphorylated PKC-α and accumulation of α-synuclein.

2. The method of claim 1, wherein ingenol-3-angelate (PEP005) is extracted from *Euphorbia peplus.*

3. The method of claim 1, wherein modulating activities comprises modulating transcript expression level.

4. The method of claim 1, wherein modulating activities comprises modulating protein expression level.

5. The method of claim 4, wherein the protein expression level comprises a decrease in α-synuclein protein.

6. The method of claim 4, wherein the protein expression level comprises an increase in TH protein.

7. The method of claim 1, wherein the therapeutically effective agent promotes lysosomal protein degradation in the subject.

8. The method of claim 1, wherein the therapeutically effective agent improves coordinated burst of electrical activity in the subject.

9. The method of claim 1, wherein the therapeutically effective agent improves one or more of: stepping, rotational asymmetry, and kinesia in the subject.

10. A method of reversing or retarding progression of Parkinson's Disease in a subject afflicted with early onset sporadic Parkinson's Disease (EOSPD) by modulating activities of α-synuclein and tyrosine hydroxylase (TH) such that α-synuclein protein level decreases and tyrosine hydroxylase (TH) level increases in dopaminergic neurons of the subject, the method comprising:

administering a pharmaceutical composition comprising a therapeutically effective agent and a pharmaceutically acceptable carrier to the subject, thereby reversing or retarding progression of Parkinson's Disease in the subject, wherein the therapeutically effective agent comprises a phorbol ester compound, ingenol-3-angelate (PEP005), wherein the subject with symptom onset prior to 50 years of age with no reported familial history of Parkinson's Disease or no known Parkinson's Disease mutations has upregulation of phosphorylated PKC-α and accumulation of α-synuclein.

11. The method of claim 10, wherein ingenol-3-angelate (PEP005) is extracted from *Euphorbia peplus.*

12. The method of claim 10, wherein the therapeutically effective agent reverses or retards degeneration of substantia nigra in the subject.

13. The method of claim 10, wherein the therapeutically effective agent maintains or promotes dopamine levels in the subject.

14. The method of claim 1, wherein ingenol-3-angelate (PEP005) is provided in the pharmaceutical composition at a dose that does not alter phosphorylated PKCα levels in the subject.

15. The method of claim 10, wherein ingenol-3-angelate (PEP005) is provided in the pharmaceutical composition at a dose that does not alter phosphorylated PKCα levels in the subject.

16. The method of claim 1, wherein the subject also has dysregulated lysosomal biogenesis and function.

17. The method of claim 16, further comprising identifying the subject afflicted with EOSPD by measuring biomarkers including upregulation of phosphorylated PKC-α, accumulation of α-synuclein, and dysregulated lysosomal biogenesis and function.

18. The method of claim 10, wherein the subject also has dysregulated lysosomal biogenesis and function.

19. The method of claim 18, further comprising identifying the subject afflicted with EOSPD by measuring biomarkers including upregulation of phosphorylated PKC-α, accumulation of α-synuclein, and dysregulated lysosomal biogenesis and function.

20. The method of claim 1, wherein the pharmaceutical composition is administered to the subject by direct infusion into the brain.

21. The method of claim 1, wherein the subject is between ages of 30-39.

* * * * *